(12) United States Patent
Klaus et al.

(10) Patent No.: US 8,318,703 B2
(45) Date of Patent: Nov. 27, 2012

(54) METHODS FOR IMPROVING KIDNEY FUNCTION

(75) Inventors: Stephen J. Klaus, Boston, MA (US); Qingjian Wang, Belmont, CA (US); Thomas B. Neff, Atherton, CA (US)

(73) Assignee: FibroGen, Inc., San Francisco, CA (US)

( * ) Notice: Subject to any disclaimer, the term of this patent is extended or adjusted under 35 U.S.C. 154(b) by 1543 days.

(21) Appl. No.: 11/446,417

(22) Filed: Jun. 1, 2006

(65) Prior Publication Data

US 2012/0149712 A1    Jun. 14, 2012

Related U.S. Application Data

(63) Continuation-in-part of application No. 10/313,551, filed on Dec. 6, 2002, now abandoned.

(60) Provisional application No. 60/386,488, filed on Jun. 5, 2002, provisional application No. 60/359,683, filed on Feb. 25, 2002, provisional application No. 60/349,659, filed on Jan. 16, 2002, provisional application No. 60/337,082, filed on Dec. 6, 2001.

(51) Int. Cl.
*A61K 31/472* (2006.01)
*A61K 31/665* (2006.01)

(52) U.S. Cl. ............... 514/100; 514/253.06; 514/300

(58) Field of Classification Search ............... 514/100, 514/253.06, 300
See application file for complete search history.

(56) References Cited

U.S. PATENT DOCUMENTS 5,916,898 A * 6/1999 Edwards et al. ............ 514/292
6,020,350 A   2/2000 Weidmann et al.
6,093,730 A   7/2000 Weidmann et al.

FOREIGN PATENT DOCUMENTS

| WO | WO-99/21860 A1 | 5/1999 |
| WO | WO-00/50390 A1 | 8/2000 |
| WO | WO-02/074981 A2 | 9/2002 |
| WO | WO-03/049686 A3 | 6/2003 |

OTHER PUBLICATIONS

Franklin et al. 2001. Inhibition of prolyl 4-hydroxylase in vitro and in vivo by members of a novel series of phenanthrolinones. Biochemical Journal, vol. 353, pp. 333-338.*
Newburger et al. 1939. Intercapillary Glomerulosclerosis a Syndrom of Diabetes, Hypertension and Albuminuria. Archives of Internal Medicine, vol. 64, No. 6, p. 1252-1264.*
Ivan, Mircea, et al., "HiFa Targeted for VHL-Mediated Destruction by Proline Hydroxylation: Implications for O2 Sensing," Science, vol. 292, Apr. 2001, pp. 464-468.
Guo, G., et al., "Improvement of Kidney Function in a Rat Model of Renal Ischemia-Reperfusion injury by Treatment with a Novel HIF Prolyl Hydroxylase Inhibitor," ASN Abstract, Oct. 2004.
Patel, Nimesh S.A., et al., "Pretreatment with EPO Reduces the Injury and Dysfunction Caused by Ischemia/Reperfusion in the Mouse Kidney in Vivo," Kidney Int., vol. 66, 2004, pp. 983-989.
Rosenberger, Christian, et al., "Expression of Hypoxia-Inducible Factor-1a and -2a in Hypoxic and Ischemic Rat Kidneys," J Am Soc Nephrol, vol. 13, 2002, pp. 1721-1732.
Seki, Teruya, et al., "Phenanthrolines," Chem Abstracts, vol. 81, No. 21, 1974, pp. 424.

* cited by examiner

*Primary Examiner* — Jon P Weber
*Assistant Examiner* — Kailash C Srivastava
(74) *Attorney, Agent, or Firm* — Leanne C. Price, Esq.

(57) ABSTRACT

The invention relates to methods for improving renal (kidney) function. Methods for decreasing blood urea nitrogen (BUN), for increasing glomerular filtration rate (GFR), and for decreasing serum creatinine are also provided.

10 Claims, 19 Drawing Sheets

METHODS FOR IMPROVING KIDNEY FUNCTION

This application is a continuation-in-part application of U.S. patent application Ser. No. 10/313,551, filed 6 Dec. 2002, now abandoned, which claimed the benefit of U.S. Provisional Application Ser. No. 60/337,082, filed on 6 Dec. 2001; U.S. Provisional Application Ser. No. 60/359,683, filed on 25 Feb. 2002; U.S. Provisional Application Ser. No. 60/349,659, filed on 16 Jan. 2002; and U.S. Provisional Application Ser. No. 60/386,488, filed on 5 Jun. 2002, each of which is incorporated by reference herein in its entirety.

FIELD OF THE INVENTION

The invention relates to methods for improving renal (kidney) function. Methods for decreasing blood urea nitrogen (BUN), for increasing glomerular filtration rate (GFR), and for decreasing serum creatinine are also provided.

BACKGROUND

The kidneys remove waste product from the body, and regulate and balance body levels of various fluids and metabolites. Impairment in kidney function can lead to serious health problems, and can be fatal. Decreased or weakened kidney function can be caused by a number of different factors and conditions, including, although not limited to, diabetes, hypertension, certain drugs or toxins, congenital disease, trauma (including dehydration, shock, etc.), injury, and surgery. These and other conditions can ultimately result in, not only weakened or impaired kidney function, but kidney failure. Subjects with acute or chronic kidney failure may be treated with hemodialysis, peritoneal dialysis or kidney transplantation. It is estimated that at least 20 million Americans suffer from chronic kidney disease, and another 20 million are at risk. (Source: National Kidney Foundation website.)

Improving kidney function in subjects with impaired kidney function would contribute greatly to quality of life by reducing the need for serious medical procedures and preventing progression to kidney failure. Therefore, there is a need in the art for methods for improving kidney function. The present invention meets this need by providing methods for improving kidney function and compounds for use in these methods. In particular, the present methods and compounds can be used to improve kidney function in a subject having or at risk for having impaired kidney function. The subject can be a subject having or at risk for having acute or chronic kidney failure, or any other impairment of the normal functioning of the kidney. The present methods and compounds can further be used to improve measurable parameters of kidney function, such as serum creatinine, glomerular filtration rate, and blood urea nitrogen (BUN).

SUMMARY OF THE INVENTION

The present invention relates to methods and compounds for improving kidney function in a subject in need thereof, e.g., a subject having or at risk for having reduced or impaired kidney function. In certain aspects, the improving comprises returning subjects to baseline renal function as indicated by serum creatinine levels and other measurable indicators of kidney function.

In one embodiment, the present invention provides a method for improving kidney function in a subject having or at risk for having impaired kidney function, the method comprising administering to the subject an effective amount of an agent that inhibits hypoxia inducible factor (HIF) hydroxylase activity.

The agent used in the present methods can be any agent that inhibits HIF hydroxylase activity, including, e.g., a polynucleotide, e.g. antisense sequence; a polypeptide; an antibody or fragment thereof, a small molecule, etc. A preferred agent of the present invention is a small molecule compound that inhibits HIF hydroxylase activity. In further embodiments, the agent is selected from the group consisting of 2-oxoglutarate mimetics, iron chelators, and proline analogs. Agents for use in the present methods include, but are not limited to, agents of Formulae I, II, III, and IV.

In a preferred embodiment, the agent is a 2-oxoglutarate mimetic. Such compounds may inhibit the target 2-oxoglutarate dioxygenase enzyme family member competitively with respect to 2-oxoglutarate. (Majamaa et al. (1984) Eur J Biochem 138:239-245; and Majamaa et al., supra.) In certain embodiments, the 2-oxoglutarate mimetic is selected from the group consisting of a compound of Formula I and Formula IV. In particular embodiments, the 2-oxoglutarate mimetic is a pyridine-2-carboxamide including, but not limited to, various compounds of Formula I. In particular embodiments, the 2-oxoglutarate mimetic is a quinoline-2-carboxamide including, but not limited to, those of Formula Ia. In particular embodiments, the 2-oxoglutarate is an isoquinoline-3-carboxamide including, but not limited to, those of Formula Ib.

In further embodiments, an agent for use in the present methods is selected from the group consisting of: 4-oxo-1,4-dihydro-[1,10]phenanthroline-3-carboxylic acid, N-((1-chloro-4-hydroxy-isoquinoline-3-carbonyl)-amino)-acetic acid, 3-{[4-(3,3-dibenzyl-ureido)-benzenesulfonyl]-[2-(4-methoxy-phenyl)-ethyl]-amino}-N-hydroxy-propionamide, 7-(4-methyl-piperazin-1-ylmethyl)-5-phenylsulfanylm-ethyl-quinolin-8-ol, 4-nitro-quinolin-8-ol, 5-butoxymethyl-quinolin-8-ol, [(3-hydroxy-pyridine-2-carbonyl)-amino]-acetic acid, N-((3-hydroxy-6-isopropoxy-quinoline-2-carbonyl)-amino)-acetic acid, [(3-hydroxy-6-trifluoromethoxy-quinoline-2-carbonyl)-amino]-acetic acid, N-((6-benzyloxy-1-chloro-4-hydroxy-isoquinoline-3-carbonyl)-amino)-acetic acid, ((7-benzyloxy-1-chloro-4-hydroxy-isoquinoline-3-carbonyl)-amino)-acetic acid methyl ester, N-((7-benzyloxy-1-chloro-4-hydroxy-isoquinoline-3-carbonyl)-amino)-acetic acid, N-((7-butoxy-4-hydroxy-isoquinoline-3-carbonyl)-amino)-acetic acid, 6-cyclohexyl-1-hydroxy-4-methyl-1H-pyridin-2-one, [(6-chloro-3-hydroxy-quinoline-2-carbonyl)-amino]-acetic acid, [(3-methoxy-pyridine-2-carbonyl)-amino]-acetic acid, 5-methoxy-4-oxo-1,4-dihydro-[1,10]phenanthroline-3-carboxylic acid, [(1,7-dichloro-4-hydroxy-isoquinoline-3-carbonyl)-amino]-acetic acid, [(4-hydroxy-7-phenoxy-isoquinoline-3-carbonyl)-amino]-acetic acid, {[4-hydroxy-7-(4-methoxy-phenoxy)-isoquinoline-3-carbonyl]-amino}-acetic acid, and [(4-hydroxy-1-methyl-7-phenoxy-isoquinoline-3-carbonyl)-amino]-acetic acid.

While, as discussed herein, a preferred agent of the present invention is a small molecule compound, it is contemplated herein that inhibiting HIF hydroxylase activity can be accomplished by any of the methods available to and known by those of skill in the art, and can involve use of any agent that interacts with, binds to, or modifies HIFα or factors that interact with HIFα, including, e.g., enzymes for which HIFα is a substrate. In certain aspects, the present invention contemplates providing a constitutively stable HIFα variant, e.g., stable HIF muteins, etc, or a polynucleotide encoding such a variant. In further aspects, HIFα is HIF1α, HIF2α, or HIF3α. In a preferred aspect, inhibiting HIF hydroxylase activity comprises administering to the subject an effective amount of an agent that inhibits HIF prolyl hydroxylase activity.

Pharmaceutical compositions or medicaments effective for improving kidney function are also provided herein. In various embodiments, the compositions comprise an effective amount of an agent that inhibits HIF hydroxylase activity and a carrier. A pharmaceutical composition effective for improving kidney function, the composition comprising an effective amount of an agent that inhibits HIF hydroxylase activity is specifically contemplated.

In various embodiments, the agent is administered orally, systemically, by injection, and intravenously.

The invention further provides methods for increasing glomerular filtration rate (GFR) in a subject in need, e.g., a subject having or at risk for having a decreased GFR, the method comprising administering to the subject a therapeutically effective amount of an agent that inhibits HIF hydroxylase activity.

Glomerular filtration rate (GFR) is the best estimate of kidney function. (Source: National Kidney Foundation website.) Therefore, in one embodiment, the subject is a subject having a decreased GFR, i.e., a GFR lower than normal GFR. In one aspect, the subject is a human subject. In further aspects, the subject is a human subject having or at risk for having a GFR selected from the group consisting of: below about 116 ml/min/1.73 m$^2$; below about 107 ml/min/1.73 m$^2$; below about 99 ml/min/1.73 m$^2$; below about 93 ml/min/1.73 m$^2$; below about 85 ml/min/1.73 m$^2$; and below about 75 ml/min/1.73 m$^2$.

In one aspect, the subject has a GFR below normal GFR, e.g., below about 90 ml/min/1.73 m$^2$. Therefore, it is contemplated that a subject having a GFR below about 90 ml/min/1.73 m$^2$, below about 60 ml/min/1.73 m$^2$, below about 30 ml/min/1.73 m$^2$, or below about 15 ml/min/1.73 m$^2$ is a suitable subject for treatment with the methods or use of medicaments provided by the present invention.

In certain aspects, the subject is a human subject, and the present invention provides methods for increasing GFR in a subject to a GFR greater than or equal to a GFR selected from the group consisting of: greater than or equal to 90 ml/min/1.73 m$^2$; 60-89 ml/min/1.73 m$^2$; 30-59 ml/min/1.73 m$^2$; 15-29 ml/min/1.73 m$^2$; and less than 15 ml/min/1.73 m$^2$.

It is further contemplated, in various embodiments, that the methods for increasing GFR be applied to increase GFR to a level above about 15 ml/min/1.73 m$^2$. In another aspect, GFR or eGFR is increased to a level above about 30 ml/min/1.73 m$^2$. In yet another aspect, GFR is increased to a level above about 60 ml/min/1.73 m$^2$. In yet another aspect, GFR is increased to a level above about 90 ml/min/1.73 m$^2$.

A method for decreasing serum creatinine in a subject in need thereof, the method comprising administering to the subject a therapeutically effective amount of an agent that inhibits HIF hydroxylase activity, is also contemplated. It is contemplated that the subject is a subject having or at risk for having increased serum creatinine or having or at risk for having impaired kidney function.

In one embodiment, the present invention provides methods for improving serum creatinine levels in a subject having or at risk for having increased creatinine levels, wherein the subject is a human subject. Normal serum creatinine levels are in the range of about 0.8-1.4 mg/dl (70.4-123.2 micromoles per liter) for adult men and about 0.6-1.0 mg/dl (52.8-88 micromoles per liter) for adult women. Therefore, in various aspects, the subject is a male human subject having a serum creatinine level of above about 1.4 mg/dl, above about 1.0 mg/dl, or above about 0.8 mg/dl. In another aspect, the subject is a female human subject having a serum creatinine level of above about 1.0 mg/dl, above about 0.8 mg/dl, or above about 0.6 mg/dl. In various aspects, the decreasing serum creatinine levels can encompass decreasing serum creatinine levels to below about 1.4, 1.0, 0.8, and 0.6 mg/dl, respectively.

Methods for decreasing blood urea nitrogen (BUN) in a subject having or at risk for having increased, i.e., higher than normal, BUN, the method comprising administering to the subject a therapeutically effective amount of an agent that inhibits HIF hydroxylase activity, are also encompassed herein. In humans, normal BUN levels typically range from 7-20 mg/dL. Therefore, in one aspect, subject is a human subject, and the decreasing BUN comprises decreasing BUN to a value at or below 20 mg/dL. In certain aspects, the subject is a human subject, and the increased BUN is a BUN selected from the group consisting of: above 20 mg/dL, above 30 mg/dL, above 40 mg/dL, above 50 mg/dL, above 60 mg/dL, above 70 mg/dL, and above 80 mg/dL.

In one embodiment, the present invention provides a method for reducing cholesterol in a subject having or at risk for having elevated cholesterol, the method comprising administering to the subject an effective amount of an agent that inhibits HIF hydroxylase activity. In a further embodiment, the subject is human, and the reducing cholesterol comprises reducing blood cholesterol levels to a level selected from the group consisting of: below 200 mg/dL, below 180 mg/dL, below 160 mg/dL, and below 150 mg/dL. In another embodiment, the subject is human and the elevated cholesterol is selected from the group consisting of a blood cholesterol level above 200 mg/dL above 220 mg/dL, and above 240 mg/dL.

In certain embodiments, the subject is a mammalian subject, including, e.g., a cat, a dog, etc. In preferred embodiments, the subject is a human subject.

In various embodiments of the present invention, the subject having or at risk for having impaired kidney function is a subject having or at risk for having any nephropathy or kidney disease. In certain embodiments, the subject has or is at risk for having diabetic nephropathy.

In one embodiment, the subject having or at risk for having impaired kidney function is a subject having or at risk for having acute kidney failure. In another embodiment, the subject is a subject having or at risk for having chronic kidney failure. In other embodiments, the subject has or is at risk for having a disorder selected from the group consisting of diabetes and hypertension.

In further embodiments of the methods described herein, the present agents are administered in combination with another therapeutic agent having a different mode of action, e.g., an ACE inhibitor (ACEI), angiotensin-II receptor blocker (ARB), statin, diuretic, digoxin, carnitine, etc.

These and other embodiments of the subject invention will readily occur to those of skill in the art in light of the disclosure herein, and all such embodiments are specifically contemplated.

BRIEF DESCRIPTION OF THE DRAWINGS

FIG. 19A shows lower blood urea nitrogen levels in treated animals relative to untreated controls at 3 and 7 days after inducing ischemia-reperfusion injury. FIG. 19B shows lower blood cholesterol levels in treated animals relative to untreated controls at 3, 7, and 14 days after inducing ischemia-reperfusion injury.

DESCRIPTION OF THE INVENTION

Figure 1A:
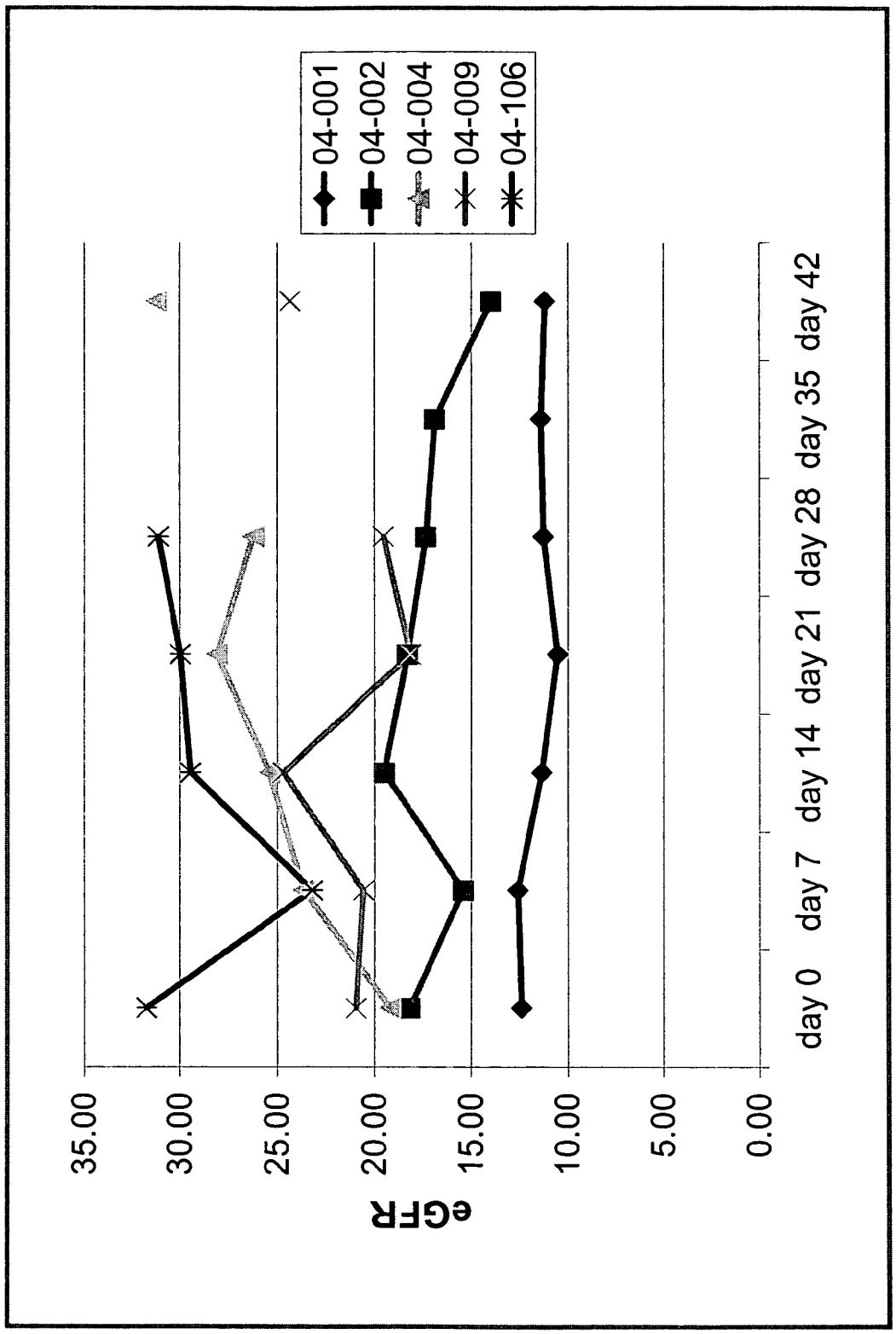
FIGS. 1A and 1B set forth data showing the methods and compounds of the present invention increased glomerular filtration rate in subjects with chronic kidney disease.

Before the present compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a fragment" includes a plurality of such fragments; a reference to an "antibody" is a reference to one or more antibodies and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) *Remington's Pharmaceutical Sciences*, 18$^{th}$ ed., Mack Publishing Co.; Hardman, J. G., Limbird, L. E., and Gilman, A. G., eds. (2001) *The Pharmacological Basis of Therapeutics*, 10$^{th}$ ed., McGraw-Hill Co.; Colowick, S. et al., eds., *Methods In Enzymolog*, Academic Press, Inc.; Weir, D. M., and Blackwell, C. C., eds. (1986) *Handbook of Experimental Immunology*, Vols. I-IV, Blackwell Scientific Publications; Maniatis, T. et al., eds. (1989) *Molecular Cloning: A Laboratory Manual*, 2$^{nd}$ edition, Vols. I-III, Cold Spring Harbor Laboratory Press; Ausubel, F. M. et al., eds. (1999) *Short Protocols in Molecular Biology*, 4$^{th}$ edition, John Wiley & Sons; Ream et al., eds. (1998) *Molecular Biology Techniques: An Intensive Laboratory Course*, Academic Press; Newton, C. R., and Graham, A., eds. (1997) *PCR* (Introduction to Biotechniques Series), 2$^{nd}$ ed., Springer Verlag.

The term "HIFα" refers to the alpha subunit of hypoxia inducible factor protein. HIFα may be any human or other mammalian protein, or fragment thereof, including, but not limited to, human HIF-1α (Genbank Accession No. Q16665), HIF-2α (Genbank Accession No. AAB41495), and HIF-3α (Genbank Accession No. AAD22668); murine HIF-1α (Genbank Accession No. Q61221), HIF-2α (Genbank Accession No. BAA20130 and AAB41496), and HIF-3α (Genbank Accession No. AAC72734); rat HIF-1α (Genbank Accession No. CAA70701), HIF-2α (Genbank Accession No. CAB96612), and HIF-3α (Genbank Accession No. CAB96611); and cow HIF-1α (Genbank Accession No. BAA78675). HIFα may also be any non-mammalian protein or fragment thereof, including *Xenopus laevis* HIF-1α (Genbank Accession No. CAB96628), *Drosophila melanogaster* HIF-1α (Genbank Accession No. JC4851), and chicken HIF-1α (Genbank Accession No. BAA34234). HIFα gene sequences may also be obtained by routine cloning techniques, for example, by using all or part of a HIFα gene sequence described above as a probe to recover and determine the sequence of a HIFα gene in another species.

Fragments of HIFα include the regions defined by human HIF-1α from amino acid 401 to 603 (Huang et al., supra), amino acid 531 to 575 (Jiang et al. (1997) J Biol Chem 272:19253-19260), amino acid 556 to 575 (Tanimoto et al., supra), amino acid 557 to 571 (Srinivas et al. (1999) Biochem Biophys Res Commun 260:557-561), and amino acid 556 to 575 (Ivan and Kaelin (2001) Science 292:464-468). Further, a fragment of HIFα includes any fragment containing at least one occurrence of the motif LXXLAP, e.g., as occurs in the HIF-1α native sequence at $L_{397}$TLLAP and $L_{559}$EMLAP. Additionally, a fragment of HIFα includes any fragment retaining at least one functional or structural characteristic of HIFα.

The terms "HIF prolyl hydroxylase" and "HIF PH" refer to any enzyme capable of hydroxylating a proline residue in the HIF protein. Preferably, the proline residue hydroxylated by HIF PH includes the proline found within the motif LXXLAP, e.g., as occurs in the human HIF-1α native sequence at $L_{397}$TLLAP and $L_{559}$EMLAP. HIF PH includes members of the Egl-Nine (EGLN) gene family described by Taylor (2001, Gene 275:125-132), and characterized by Aravind and Koonin (2001, Genome Biol 2:RESEARCH0007), Epstein et al. (2001, Cell 107:43-54), and Bruick and McKnight (2001, Science 294:1337-1340). Examples of HIF PH enzymes include human SM-20 (EGLN1) (GenBank Accession No. AAG33965; Dupuy et al. (2000) Genomics 69:348-54), EGLN2 isoform 1 (GenBank Accession No. CAC42510; Taylor, supra), EGLN2 isoform 2 (GenBank Accession No. NP_060025), and EGLN3 (GenBank Accession No. CAC42511; Taylor, supra); mouse EGLN1 (GenBank Accession No. CAC42515), EGLN2 (GenBank Accession No. CAC42511), and EGLN3 (SM-20) (GenBank Accession No. CAC42517); and rat SM-20 (GenBank Accession No. AAA19321). Additionally, HIF PH may include *Caenorhabditis elegans* EGL-9 (GenBank Accession No. AAD56365) and *Drosophila melanogaster* CG1114 gene product (GenBank Accession No. AAF52050). HIF PH also includes any fragment retaining at least one stuctural or function feature of the foregoing full-length proteins, including a fragment having hydroxylase activity.

The terms "amino acid sequence" or "polypeptide" as used herein, e.g., to refer to HIFα and fragments thereof, or HIF PH and fragments thereof, contemplate an oligopeptide, peptide, or protein sequence, or to a fragment of any of these, and to naturally occurring or synthetic molecules. "Fragments" can refer to any portion of a sequence that retains at least one structural or functional characteristic of the protein. Immunogenic fragments or antigenic fragments are fragments of polypeptides, preferably, fragments of about five to fifteen amino acids in length, that retain at least one biological or immunological activity. Where "amino acid sequence" is used to refer to the polypeptide sequence of a naturally occurring protein molecule, "amino acid sequence" and like terms are not meant to limit the amino acid sequence to the complete native sequence associated with the recited protein molecule.

The term "related proteins" as used herein, for example, to refer to proteins related to HIFα prolyl hydroxylase, encompasses other 2-oxoglutarate dioxygenase enzymes, especially those family members that similarly require $Fe^{2+}$, 2-oxoglutarate, and oxygen to maintain hydroxylase activity. Such enzymes include, but are not limited to, e.g., procollagen lysyl hydroxylase, procollagen prolyl 4-hydroxylase, and Factor Inhibiting HIF (FIH), an asparaginyl hydroxylase responsible for regulating transactivation of HIFα. (GenBank Accession No. AAL27308; Mahon et al. (2001) Genes Dev 15:2675-2686; Lando et al. (2002) Science 295:858-861; and Lando et al. (2002) Genes Dev 16:1466-1471. See, also, Elkins et al. (2002) J Biol Chem C200644200.)

The term "agonist" refers to a molecule that increases or prolongs the duration of the effect of a particular molecule, e.g., an enzyme or protein, or a particular environment, e.g., hypoxia. Agonists may include proteins, nucleic acids, carbohydrates, or any other molecules that modulate the effects of the target molecule.

The term "antagonist" refers to a molecule which decreases the extent or duration of the effect of the biological or immunological activity of a particular molecule. Antagonists may include proteins, nucleic acids, carbohydrates, antibodies, or any other molecules that decrease the effect of the target molecule.

The term "microarray" refers to any arrangement of nucleic acids, amino acids, antibodies, etc., on a substrate. The substrate can be any suitable support, e.g., beads, glass, paper, nitrocellulose, nylon, or any appropriate membrane, etc. A substrate can be any rigid or semi-rigid support including, but not limited to, membranes, filters, wafers, chips, slides, fibers, beads, including magnetic or nonmagnetic beads, gels, tubing, plates, polymers, microparticles, capillaries, etc. The substrate can provide a surface for coating and/or can have a variety of surface forms, such as wells, pins, trenches, channels, and pores, to which the nucleic acids, amino acids, etc., may be bound.

The term "excipient" as used herein means an inert or inactive substance used in the production of pharmaceutical products or other tablets, including without limitation any substance used as a binder, disintegrant, coating, compression/encapsulation aid, cream or lotion, lubricant, parenteral, sweetener or flavoring, suspending/gelling agent, or wet granulation agent. Binders include, e.g., carbopol, povidone, xanthan gum, etc.; coatings include, e.g., cellulose acetate phthalate, ethylcellulose, gellan gum, maltodextrin, etc.; compression/encapsulation aids include, e.g., calcium carbonate, dextrose, fructose dc, honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams and lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; parenterals include, e.g., mannitol, povidone, etc.; plasticizers include, e.g., dibutyl sebacate, polyvinylacetate phthalate, etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

The term "sample" is used herein in its broadest sense. Samples may be derived from any source, for example, from bodily fluids, secretions, tissues, cells, or cells in culture including, but not limited to, saliva, blood, urine, serum, plasma, vitreous, synovial fluid, cerebral spinal fluid, amniotic fluid, and organ tissue (e.g., biopsied tissue); from chromosomes, organelles, or other membranes isolated from a cell; from genomic DNA, cDNA, RNA, mRNA, etc.; and from cleared cells or tissues, or blots or imprints from such cells or tissues. Samples may be derived from any source, such as, for example, a human subject, or a non-human mammalian subject, etc. Also contemplated are samples derived from any animal model of disease. A sample can be in solution or can be, for example, fixed or bound to a substrate. A sample can refer to any material suitable for testing for the presence of HIFα or of fragments of HIFα or suitable for screening for molecules that bind to HIFα or to fragments thereof. Methods for obtaining such samples are within the level of skill in the art.

The term "subject" is used herein in its broadest sense. Subjects may include isolated cells, either prokaryotic or eukaryotic, or tissues grown in culture. Preferably, subjects include animals, particularly a mammalian species including rat, rabbit, bovine, ovine, porcine, murine, equine, and primate, particularly human.

Invention

The present invention relates to the discovery that administration of agents that inhibit HIF hydroxylase activity to subjects having or at risk for having impaired kidney function effectively improved kidney function in these subjects, as demonstrated by improvement in a series of measurable parameters of kidney function, including GFR, serum creatinine levels, BUN, and cholesterol levels.

Measurement of GFR in human subjects is the best overall index of kidney function in health and disease. (Smith, Diseases of the kidney and urinary tract, In: Structure and Function in Health and Disease, New York; Oxford Univ. Press, 1951:836-887.) GFR can be determined by measuring the urinary clearance of a filtration marker, such as inulin, iothalamate, or iohexol. It is noted that, in a clinical setting, the term "GFR" often refers to estimated GFR (eGFR), which is a GFR value estimated by determining creatinine clearance. For the purposes of the present invention, the term "GFR" is used herein in reference to the present methods and compounds specifically contemplates both GFR obtained through direct measurement and estimated GFR obtained through any of the various standard formulas used to estimate GFR. Thus, the present methods for "increasing GFR" are methods for increasing GFR obtained through direct meaurement and for increasing eGFR, estimated using various formulas.

Creatinine clearance (often expressed as ml/min) can be determined by comparing the level of creatinine in urine with the creatinine level in blood, usually based on assessments of a 24-hour urine sample and a blood sample drawn at the end of the 24-hour period, and is used to estimate GFR. In clinical practice, creatinine clearance is most often estimated from the serum creatinine concentration. Creatinine clearance is related directly to the urine creatinine excretion and inversely to serum creatinine concentration. Various formulas that provide estimates of creatinine clearance, and therefore estimates of GFR, using parameters such as serum creatinine concentration, age, sex, and body size, have been developed and are standard in the art. (See, e.g., Cockcroft and Gault (1976) Nephron 16:31-41; Levey et al (1999) Annals of Internal Medicine 130:462-470; Rule et al (2004) Ann Intern Med 141:929-937.)

Normal GFR or eGFR varies according to age, gender, and body weight. In young adults, GFR is approximately 120-130 ml/min/1.73 m$^2$. This value declines with age. A persistently reduced GFR is an indication of renal impairment, such as chronic kidney disease, and often precedes the onset of kidney failure. The average values of estimated GFR by decade in the general population are as follows: 20-29 years of age, average estimated GFR of 116 ml/min/1.73 m$^2$; 30-39 years of age, average estimated GFR of 107 ml/min/1.73 m$^2$; 40-49 years of age, average estimated GFR of 99 ml/min/1.73 m$^2$; 50-59 years of age, average estimated GFR of 93 ml/min/1.73 m$^2$; 60-69 years of age, average estimated GFR of 85 ml/min/1.73 m$^2$; and 70 years of age and over, average estimated GFR of 75 ml/min/1.73 m$^2$. Although age-related decline in GFR (or eGFR) has been considered part of normal aging, decreased GFR (or eGFR) in the elderly is an independent predictor of various adverse outcomes, such as, for example, cardiovascular disease and death, and there is thus an outstanding need for methods for increasing GFR or eGFR in such subjects.

Kidney or renal disorders can lead to reduced or impaired kidney function, which is associated with alterations in various measurable parameters, including, e.g., a change or decline in GFR or eGFR. Various stages of chronic kidney disease are associated with GFR or eGFR levels as follows: stage 1 (kidney damage with normal or increased GFR), GFR or eGFR greater than or equal to 90 ml/min/1.73 m$^2$; stage 2 (kidney damage with mild decrease in GFR), GFR or eGFR of 60-89 ml/min/1.73 m$^2$; stage 3 (kidney damage with moderate decrease in GFR), GFR or eGFR of 30-59 ml/min/1.73 m$^2$; stage 4 (kidney damage with severe decrease in GFR), GFR or eGFR of 15-29 ml/min/1.73 m$^2$; and stage 5 (kidney failure), GFR or eGFR less than 15 ml/min/1.73 m$^2$.

It is contemplated that the present methods can be applied to improving renal function, increasing GFR or eGFR in a subject with any clinically accepted standard of measurement indicative of nephropathy or renal disease, or a subject at risk for developing such a renal disorder. In certain embodiments, the subject has chronic kidney disease. In various embodiments, the subject has stage I kidney disease, stage 2 kidney disease, stage 3 kidney disease, stage 4 kidney disease, or stage 5 kidney disease. It is specifically contemplated that the subject has severe impairment of renal function or late-stage kidney disease.

In one aspect, the subject has a GFR or eGFR below normal GFR or eGFR, e.g., below about 90 ml/min/1.73 m$^2$. Therefore, it is contemplated that a subject having a GFR or eGFR below about 90 ml/min/1.73 m$^2$, below about 60 ml/min/1.73 m$^2$, below about 30 ml/min/1.73 m$^2$, or below about 15 ml/min/1.73 m$^2$ is a suitable subject for treatment with the methods or use of medicaments provided by the present invention.

It is further contemplated, in various embodiments, that the methods for increasing GFR or eGFR be applied to increase GFR or eGFR to a level above about 15 ml/min/1.73 m$^2$. In another aspect, GFR or eGFR is increased to a level above about 30 ml/min/1.73 m$^2$. In yet another aspect, GFR or eGFR is increased to a level above about 60 ml/min/1.73 m$^2$. In yet another aspect, GFR or eGFR is increased to a level above about 90 ml/min/1.73 m$^2$.

Serum creatinine levels are an established indicator of impaired kidney function and chronic kidney disease. Serum creatinine levels are determined by the rate at which serum creatinine is being removed, and can serve as a measure of kidney function. As kidney function is impaired, serum creatinine levels increase. Serum creatinine levels can be expressed as milligrams per deciliter (mg/dl) or as micromoles per liter (μmol/l). For example, a serum creatinine level of 1 mg/dl is the same as a serum creatinine level of 88 μmol/l. Normal serum creatinine levels are in the range of about 0.8-1.4 mg/dl (70.4-123.2 micromoles per liter) for adult men and about 0.6-1.0 mg/dl (52.8-88 micromoles per liter) for adult women. Therefore, in various aspects, the invention provides methods for decreasing, or methods for manufacture of a medicament suitable for use in decreasing, serum creatinine levels in a subject in need thereof. In one aspect, the subject is a male human subject having a serum creatinine level of above about 1.4 mg/dl, above about 1.0 mg/dl, or above about 0.8 mg/dl. In another aspect, the subject is a female human subject having a serum creatinine level of above about 1.0 mg/dl, above about 0.8 mg/dl, or above about 0.6 mg/dl. In various aspects, the decreasing serum creatinine levels can encompass decreasing serum creatinine levels to below about 1.4, 1.0, 0.8, and 0.6 mg/dl, respectively.

Elevated blood urea nitrogen (BUN) is an indicator of poor or compromised kidney function. Normal BUN levels for adult humans range from 7-20 mg/dl. Therefore, in certain embodiments, the invention provides methods for reducing BUN levels to below 20 mg/dl are provided herein. A greatly elevated BUN (>60 mg/dl) generally indicates a moderate-to-severe degree of renal failure, and methods and compounds for decreasing BUN to levels below 60 mg/dl are specifically contemplated herein.

High cholesterol levels have been linked to kidney disease and kidney failure. Increased cholesterol levels can be indicative of loss or impairment of renal function. As shown in Example 7 and in FIGS. 19A and 19B, methods and compounds of the present invention effectively reduced cholesterol levels in an in vivo model of impaired kidney function/renal disease. Accordingly, the present invention provides in one aspect methods for reducing elevated cholesterol in a subject having or at risk for having elevated cholesterol, the methods comprising administering to the subject an effective amount of an agent that inhibits HIF hydroxylase activity.

In adult human subjects, blood cholesterol levels are preferably below 200 mg/dL. Methods for decreasing cholesterol levels to levels of below 200 mg/dL, 180 mg/dL, 160 mg/dL, and 150 mg/dL are specifically provided herein. Blood cholesterol levels of about 200-239 mg/dL represent an increased risk for heart disease and may be associated with kidney disease, including progressive chronic kidney failure. Levels above 240 mg/dL represent a substantial risk for cardiac disease, and may present an elevated risk of impaired kidney function and chronic kidney disease. Cholesterol levels can be measured by various methods standard in the art (e.g., fasting blood cholesterol, etc.).

While, as discussed herein, a preferred agent of the present invention is a small molecule compound, it is contemplated herein that inhibiting HIF hydroxylase activity can be accomplished by any of the methods available to and known by those of skill in the art, and can involve use of any agent that interacts with, binds to, or modifies HIFα or factors that interact with HIFα, including, e.g., enzymes for which HIFα is a substrate. In certain aspects, the present invention contemplates providing a constitutively stable HIFα variant, e.g., stable HIF muteins, etc, or a polynucleotide encoding such a variant. In further aspects, HIFα is HIF1α, HIF2α, or HIF3α. In a preferred aspect, inhibiting HIF hydroxylase activity comprises administering to the subject an effective amount.

The agent used in the present methods can be any agent that inhibits HIF hydroxylase activity, including, e.g., a polynucleotide, e.g. antisense sequence; a polypeptide; an antibody or fragment thereof, a small molecule, etc. A preferred agent of the present invention is a small molecule compound that inhibits HIF hydroxylase activity. In further embodiments, the agent is selected from the group consisting of 2-oxoglutarate mimetics, iron chelators, and proline analogs. Agents for use in the present methods include, but are not limited to, agents of Formulae I, II, III, and IV.

In a preferred embodiment, the agent is a 2-oxoglutarate mimetic. Such compounds may inhibit the target 2-oxoglutarate dioxygenase enzyme family member competitively with respect to 2-oxoglutarate. (Majamaa et al. (1984) Eur J Biochem 138:239-245; and Majamaa et al., supra.) In certain embodiments, the 2-oxoglutarate mimetic is selected from the group consisting of a compound of Formula I and Formula IV. In particular embodiments, the 2-oxoglutarate mimetic is a pyridine-2-carboxamide including, but not limited to, various compounds of Formula I. In particular embodiments, the 2-oxoglutarate mimetic is a quinoline-2-carboxamide including, but not limited to, those of Formula Ia. In particular embodiments, the 2-oxoglutarate mimetic is an isoquinoline-3-carboxamide including, but not limited to, those of Formula Ib. In particular embodiments, the 2-oxoglutarate mimetic is a cinnoline-3-carboxamide including, but not limited to, those of Formula Ic. In particular embodiments, the 2-oxoglutarate mimetic is a beta-carboline-3-carboxamide including, but not limited to, various compounds of Formula Id.

As stated above, in certain embodiments, compounds used in the methods of the invention are selected from a compound of the Formula I

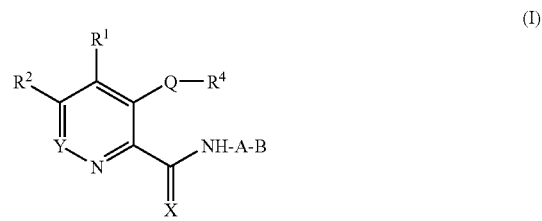

(I)

wherein

A is 1,2-arylidene, 1,3-arylidene, 1,4-arylidene; or ($C_1$-$C_4$)-alkylene, optionally substituted by one or two halogen, cyano, nitro, trifluoromethyl, ($C_1$-$C_6$)-alkyl, ($C_1$-$C_6$)-hydroxyalkyl, ($C_1$-$C_6$)-alkoxy, —O—$[CH_2]_x$—$C_fH_{(2f+1-g)}Hal_g$, ($C_1$-$C_6$)-fluoroalkoxy, ($C_1$-$C_8$)-fluoroalkenyloxy, ($C_1$-$C_8$)-fluoroalkynyloxy, —$OCF_2Cl$, —O—$CF_2$—CHFCl; ($C_1$-$C_6$)-alkylmercapto, ($C_1$-$C_6$)-alkylsulfinyl, ($C_1$-$C_6$)-alkylsulfonyl, ($C_1$-$C_6$)-alkylcarbonyl, ($C_1$-$C_6$)-alkoxycarbonyl, carbamoyl, N—($C_1$-$C_4$)-alkylcarbamoyl, N,N-di-($C_1$-$C_4$)-alkylcarbamoyl, ($C_1$-$C_6$)-alkylcarbonyloxy, ($C_3$-$C_8$)-cycloalkyl, phenyl, benzyl, phenoxy, benzyloxy, anilino, N-methylanilino, phenylmercapto, phenylsulfonyl, phenylsulfinyl, sulfamoyl, N—($C_1$-$C_4$)-alkylsulfamoyl, N,N-di-($C_1$-$C_4$)-alkylsulfamoyl; or by a substituted ($C_6$-$C_{12}$)-aryloxy, ($C_7$-$C_{11}$)-aralkyloxy, ($C_6$-$C_{12}$)-aryl, ($C_7$-$C_{11}$)-aralkyl radical, which carries in the aryl moiety one to five identical or different substituents selected from halogen, cyano, nitro, trifluoromethyl, ($C_1$-$C_6$)-alkyl, ($C_1$-$C_6$)-alkoxy, —O—$[CH_2]_x$-$C_fH_{(2f+1-g)}Hal_g$, —$OCF_2Cl$, —O—$CF_2$—CHFCl, ($C_1$-$C_6$)-alkylmercapto, ($C_1$-$C_6$)-alkylsulfinyl, ($C_1$-$C_6$)-alkylsulfonyl, ($C_1$-$C_6$)-alkylcarbonyl, ($C_1$-$C_6$)-alkoxycarbonyl, carbamoyl, N—($C_1$-$C_4$)-alkylcarbamoyl, N,N-di-($C_1$-$C_4$)-alkylcarbamoyl, ($C_1$-$C_6$)-alkylcarbonyloxy, ($C_3$-$C_8$)-cycloalkyl, sulfamoyl, N—($C_1$-$C_4$)-alkylsulfamoyl, N,N-di-($C_1$-$C_4$)-alkylsulfamoyl; or wherein A is —$CR^5R^6$ and $R^5$ and $R^6$ are each independently selected from hydrogen, ($C_1$-$C_6$)-alkyl, ($C_3$-$C_7$)-cycloalkyl, aryl, or a substituent of the α-carbon atom of an α-amino acid, wherein the amino acid is a natural L-amino acid or its D-isomer;

B is —$CO_2H$, —$NH_2$, —$NHSO_2CF_3$, tetrazolyl, imidazolyl, 3-hydroxyisoxazolyl, —CONHCOR''', —CONHSOR''', CONHSO$_2$R''', where R''' is aryl, heteroaryl, ($C_3$-$C_7$)-cycloalkyl, or ($C_1$-$C_4$)-alkyl, optionally monosubstituted by ($C_6$-$C_{12}$)-aryl, heteroaryl, OH, SH, ($C_1$-$C_4$)-alkyl, ($C_1$-$C_4$)-alkoxy, ($C_1$-$C_4$)-thioalkyl, ($C_1$-$C_4$)-sulfinyl, ($C_1$-$C_4$)-sulfonyl, $CF_3$, Cl, Br, F, I, NO2, —COOH, ($C_2$-$C_5$)-alkoxycarbonyl, $NH_2$, mono-($C_1$-$C_4$-alkyl)-amino, di-($C_1$-$C_4$-alkyl)-amino, or ($C_1$-$C_4$)-perfluoroalkyl;

or wherein B is a $CO_2$-G carboxyl radical, where G is a radical of an alcohol G-OH in which G is selected from $(C_1-C_{20})$-alkyl radical, $(C_3-C_8)$ cycloalkyl radical, $(C_2-C_{20})$-alkenyl radical, $(C_3-C_8)$-cycloalkenyl radical, retinyl radical, $(C_2-C_{20})$-alkynyl radical, $(C_4-C_{20})$-alkenynyl radical, where the alkenyl, cycloalkenyl, alkynyl, and alkenynyl radicals contain one or more multiple bonds; $(C_6-C_{16})$-carbocyclic aryl radical, $(C_7-C_{16})$-carbocyclic aralkyl radical, heteroaryl radical, or heteroaralkyl radical, wherein a heteroaryl radical or heteroaryl moiety of a heteroaralkyl radical contains 5 or 6 ring atoms; and wherein radicals defined for G are substituted by one or more hydroxyl, halogen, cyano, trifluoromethyl, nitro, carboxyl, $(C_1-C_{12})$-alkyl, $(C_3-C_8)$-cycloalkyl, $(C_5-C_8)$-cycloalkenyl, $(C_6-C_{12})$-aryl, $(C_7-C_{16})$-aralkyl, $(C_2-C_{12})$-alkenyl, $(C_2-C_{12})$-alkynyl, $(C_1-C_{12})$-alkoxy, $(C_1-C_{12})$-alkoxy-$(C_1-C_{12})$-alkyl, $(C_1-C_{12})$-alkoxy-$(C_1-C_{12})$-alkoxy, $(C_6-C_{12})$-aryloxy, $(C_7-C_{16})$-aralkyloxy, $(C_1-C_8)$-hydroxyalkyl, —O—$[CH_2]_x$—$C_fH_{(2f+1-g)}$—$F_g$, —$OCF_2Cl$, —$OCF_2$—CHFCl, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_2-C_{12})$-alkenylcarbonyl, $(C_2-C_{12})$-alkynylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{12})$-alkenyloxycarbonyl, $(C_2-C_{12})$-alkynyloxycarbonyl, acyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$ aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy, carbamoyl, N—$(C_1-C_{12})$-alkylcarbamoyl, N.N-di$(C_1-C_{12})$-alkylcarbamoyl, N—$(C_3-C_8)$-cycloalkyl-carbamoyl, N—$(C_6-C_{16})$-arylcarbamoyl, N—$(C_7-C_{16})$-aralkylcarbamoyl, N—$(C_1-C_{10})$-alkyl-N—$(C_6-C_{16})$-arylcarbamoyl, N—$(C_1-C_{10})$-alkyl-N—$(C_7-C_{16})$-aralkylcarbamoyl, N-(($C_1-C_{10})$-alkoxy-$(C_1-C_{10})$-alkyl)-carbamoyl, N-(($C_6-C_{12})$-aryloxy-$(C_1-C_{10})$alkyl)-carbamoyl, N-(($C_7-C_{16})$-aralkyloxy-$(C_1-C_{10})$-alkyl)-carbamoyl, N—$(C_1-C_{10})$-alkyl-N-(($C_1-C_{10})$-alkoxy-$(C_1-C_{10})$-alkyl)-carbamoyl, N—$(C_1-C_{10})$-alkyl-N-(($C_6-C_{16})$-aryloxy-$(C_1-C_{10})$-alkyl)-carbamoyl, N—$(C_1-C_{10})$-alkyl-N-(($C_7-C_{16})$-aralkyloxy-$(C_1-C_{10})$-alkyl)-carbamoyl, carbamoyloxy, N—$(C_1-C_{12})$-alkylcarbamoyloxy, N.N-di-$(C_1-C_{12})$-alkylcarbamoyloxy, N—$(C_3-C_8)$-cycloalkylcarbamoyloxy, N—$(C_6-C_{12})$-arylcarbamoyloxy, N—$(C_7-C_{16})$-aralkylcarbamoyloxy, N—$(C_1-C_{10})$-alkyl-N—$(C_6-C_{12})$-arylcarbamoyloxy, N$(C_1-C_{10})$-alkyl-N—$(C_7-C_{16})$-aralkylcarbamoyloxy, N-(($C_1-C_{10})$-alkyl)-carbamoyloxy, N-(($C_6-C_{12})$-aryloxy-$(C_1-C_{10})$-alkyl)-carbamoyloxy, N-(($C_7-C_{16})$-aralkyloxy-$(C_1-C_{10})$-alkyl)-carbamoyloxy, N—$(C_1-C_{10})$-alkyl-N-(($C_1-C_{10})$-alkoxy-$(C_1-C_{10})$-alkyl)-carbamoyloxy, N—$(C_1-C_{10})$-alkyl-N-(($C_6-C_{12})$-aryloxy-$(C_1-C_{10})$-alkyl)-carbamoyloxy, N—$(C_1-C_{10})$-alkyl-N-(($C_7-C_{16})$-aralkyloxy-$(C_1-C_{10})$-alkyl)-carbamoyloxy, amino, $(C_1-C_{12})$-alkylamino, di-$(C_1-C_{12})$-alkylamino, $(C_3-C_8)$-cycloalkylamino, $(C_2-C_{12})$-alkenylamino, $(C_2-C_{12})$-alkynylamino, N—$(C_6-C_{12})$-arylamino, N—$(C—C_{11})$-aralkylamino, N-alkyl-aralkylamino, N-alkyl-arylamino, $(C_1-C_{12})$-alkoxyamino, $(C_1-C_{12})$-alkoxy-N—$(C_1-C_{10})$-alkylamino, $(C_1-C_{12})$-alkylcarbonylamino, $(C_3-C_8)$-cycloalkylcarbonylamino, $(C_6-C_{12})$arylcarbonylamino, $(C_7-C_{16})$-aralkylcarbonylamino, $(C_1-C_{12})$-alkylcarbonyl-N—$(C_1-C_{10})$-alkylamino, $(C_3-C_8)$-cycloalkylcarbonyl-N—$(C_1-C_{10})$-alkylamino, $(C_6-C_{12})$-arylcarbonyl-N—$(C_1-C_{10})$alkylamino, $(C_7-C_{11})$-aralkylcarbonyl-N—$(C_1-C_{10})$-alkylamino, $(C_1-C_{12})$-alkylcarbonylamino-$(C_1-C_8)$-alkyl, $(C_3-C_8)$-cycloalkylcarbonylamino-$(C_1-C_8)$alkyl, $(C_6-C_{12})$-arylcarbonylamino-$(C_1-C_8)$-alkyl, $(C_7-C_{16})$-aralkylcarbonylamino$(C_1-C_8)$-alkyl, amino-$(C_1-C_{10})$-alkyl, N—$(C_1-C_{10})$ alkylamino-$(C_1-C_{10})$-alkyl, N.N-di-$(C_1-C_{10})$-alkylamino-$(C_1-C_{10})$-alkyl, $(C_3-C_8)$ cycloalkylamino-$(C_1-C_{10})$-alkyl, $(C_1-C_{12})$-alkylmercapto, $(C_1-C_{12})$-alkylsulfinyl, $(C_1-C_{12})$-alkylsulfonyl, $(C_6-C_{16})$-arylmercapto, $(C_6-C_{16})$-arylsulfinyl, $(C_6-C_{12})$-arylsulfonyl, $(C_7-C_{16})$-aralkylmercapto, $(C_7-C_{16})$-aralkylsulfinyl, $(C_7-C_{16})$-aralkylsulfonyl, sulfamoyl, N—$(C_1-C_{10})$-alkylsulfamoyl, N.N-di$(C_1-C_{10})$-alkylsulfamoyl, $(C_3-C_8)$-cycloalkylsulfamoyl, N—$(C_6-C_{12})$-alkylsulfamoyl, N—$(C_7-C_{16})$-aralkylsulfamoyl, N—$(C_1-C_{10})$-alkyl-N—$(C_6-C_{12})$-arylsulfamoyl, N—$(C_1-C_{10})$-alkyl-N—$(C_7-C_{16})$-aralkylsulfamoyl, $(C_1-C_{10})$-alkylsulfonamido, N-(($C_1-C_{10})$-alkyl)-$(C_1-C_{10})$-alkylsulfonamido, $(C_7-C_{16})$-aralkylsulfonamido, or N-(($C_1-C_{10})$-alkyl-$(C_7-C_{16})$-aralkylsulfonamido; wherein radicals which are aryl or contain an aryl moiety, may be substituted on the aryl by one to five identical or different hydroxyl, halogen, cyano, trifluoromethyl, nitro, carboxyl, $(C_1-C_{12})$-alkyl, $(C_3-C_8)$-cycloalkyl, $(C_6-C_{12})$-aryl, $(C_7-C_{16})$-aralkyl, $(C_1-C_{12})$-alkoxy, $(C_1-C_{12})$-alkoxy-$(C_1-C_{12})$alkyl, $(C_1-C_{12})$-alkoxy-$(C_1-C_{12})$ alkoxy, $(C_6-C_{12})$-aryloxy, $(C_7-C_{16})$-aralkyloxy, $(C_1-C_8)$-hydroxyalkyl, $(C_1-C_{12})$-alkylcarbonyl, $(C_3-C_8)$-cycloalkyl-carbonyl, $(C_6-C_{12})$-arylcarbonyl, $(C_7-C_{16})$ aralkylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{12})$-alkenyloxycarbonyl, $(C_2-C_{12})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy, carbamoyl, N—$(C_1-C_{12})$-alkylcarbamoyl, N.N-di-$(C_1-C_{12})$-alkylcarbamoyl, N—$(C_3-C_8)$-cycloalkylcarbamoyl, N—$(C_6-C_{12})$-arylcarbamoyl, N—$(C_7-C_{16})$-aralkylcarbamoyl, N—$(C_1-C_{10})$-alkyl-N—$(C_6-C_{12})$-arylcarbamoyl, N—$(C_1-C_{10})$-alkyl-N—$(C_7-C_{16})$-aralkylcarbamoyl, N-(($C_1-C_{10})$-alkoxy-$(C_1-C_{10})$-alkyl)-carbamoyl, N-(($C_6-C_{12})$-aryloxy-$(C_1-C_{10})$-alkyl)-carbamoyl, N-(($C_7-C_{16})$-aralkyloxy-$(C_1-C_{10})$-alkyl)-carbamoyl, N—$(C_1-C_{10})$-alkyl-N-(($C_1-C_{10})$-alkoxy-$(C_1-C_{10})$-alkyl)-carbamoyl, N—$(C_1-C_{10})$-alkyl-N-(($C_6-C_{12})$-aryloxy-$(C_1-C_{10})$-alkyl)-carbamoyl, N—$(C_1-C_{10})$-alkyl-N-(($C_7-C_{16})$-aralkyloxy-$(C_1-C_{10})$-alkyl)-carbamoyl, carbamoyloxy, N—$(C_1-C_{12})$-alkylcarbamoyloxy, N,N-di-$(C_1-C_{12})$-alkylcarbamoyloxy, N—$(C_3-C_8)$-cycloalkylcarbamoyloxy, N—$(C_6-C_{12})$-arylcarbamoyloxy, N—$(C_7-C_{16})$-aralkylcarbamoyloxy, N—$(C_1-C_{10})$-alkyl-N—$(C_6-C_{12})$-arylcarbamoyloxy, N$(C_1-C_{10})$-alkyl-N—$(C_7-C_{16})$-aralkylcarbamoyloxy, N-(($C_1-C_{10})$-alkyl)-carbamoyloxy, N-(($C_6-C_{12})$-aryloxy-$(C_1-C_{10})$-alkyl)-carbamoyloxy, N-(($C_7-C_{16})$-aralkyloxy-$(C_1-C_{10})$-alkyl)-carbamoyloxy, N—$(C_1-C_{10})$-alkyl-N-(($C_1-

$C_{10}$)-alkoxy-($C_1$-$C_{10}$)-alkyl)-carbamoyloxy, N—($C_1$-$C_{10}$)-alkyl-N—(($C_6$-$C_{12}$)-aryloxy-($C_1$-$C_{10}$)-alkyl)-carbamoyloxy, N—($C_1$-$C_{10}$)-alkyl-N—(($C_7$-$C_{16}$)-aralkyloxy-($C_1$-$C_{10}$)-alkyl)-carbamoyloxy, amino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkylaralkylamino, N-alkylarylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkylcarbonylamino, ($C_3$-$C_8$)-cycloalkylcarbonylamino, ($C_6$-$C_{12}$)-arylcarbonylamino, ($C_7$-$C_{16}$)-alkylcarbonylamino, ($C_1$-$C_{12}$)-alkylcarbonyl-N—($C_1$-$C_{10}$)-alkylamino, ($C_3$-$C_8$)-cycloalkylcarbonyl-N—($C_1$-$C_{10}$)-alkylamino, ($C_6$-$C_{12}$)-arylcarbonyl-N—($C_1$-$C_{10}$)-alkylamino, ($C_7$-$C_{11}$)-aralkylcarbonyl-N—($C_1$-$C_{10}$)-alkylamino, ($C_1$-$C_{12}$)-alkylcarbonylamino-($C_1$-$C_8$)-alkyl, ($C_3$-$C_8$)-cycloalkylcarbonylamino-($C_1$-$C_8$)-alkyl, ($C_6$-$C_{12}$)-arylcarbonylamino-($C_1$-$C_8$)-alkyl, ($C_7$-$C_{16}$)-aralkylcarbonylamino-($C_1$-$C_8$)-alkyl, amino-($C_1$-$C_{10}$)-alkyl, N—($C_1$-$C_{10}$)-alkylamino-($C_1$-$C_{10}$)alkyl, N,N-di-($C_1$-$C_{10}$)-alkylamino-($C_1$-$C_{10}$)-alkyl, ($C_3$-$C_8$)-cycloalkylamino-($C_1$-$C_{10}$)-alkyl, ($C_1$-$C_{12}$)-alkylmercapto, ($C_1$-$C_{12}$)-alkylsulfinyl, ($C_1$-$C_{12}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, or ($C_7$-$C_{16}$)-aralkylsulfonyl;

X is O or S;

Q is O, S, NR', or a bond;

where, if Q is a bond, $R^4$ is halogen, nitrile, or trifluoromethyl;

or where, if Q is O, S, or NR', $R^4$ is hydrogen, ($C_1$-$C_{10}$)-alkyl radical, ($C_2$-$C_{10}$)-alkenyl radical, ($C_2$-$C_{10}$)-alkynyl radical, wherein alkenyl or alkynyl radical contains one or two C—C multiple bonds; unsubstituted fluoroalkyl radical of the formula —$[CH_2]_x$-$C_fH_{(2f+1-g)}$—$F_g$, ($C_1$-$C_8$)-alkoxy-($C_1$-$C_6$)-alkyl radical, ($C_1$-$C_6$)-alkoxy-($C_1$-$C_4$)-alkoxy-($C_1$-$C_4$)-alkyl radical, aryl radical, heteroaryl radical, ($C_7$-$C_{11}$)-aralkyl radical, or a radical of the formula Z $$—[CH_2]_v—[O]_w—[CH_2]_t—E \quad (Z)$$

where

E is a heteroaryl radical, a ($C_3$-$C_8$)-cycloalkyl radical, or a phenyl radical of the formula F

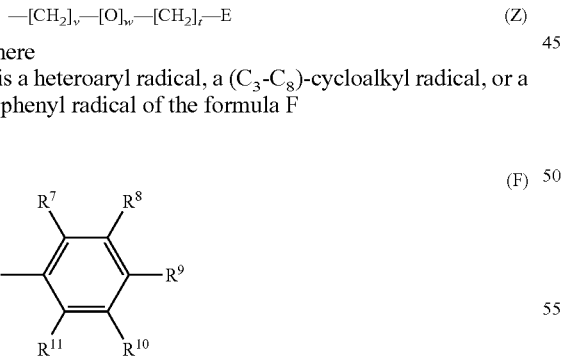

(F)

v is 0-6,
w is 0 or 1,
t is 0-3, and
$R^7$, $R^8$, $R^9$, $R^{10}$, and $R^{11}$ are identical or different and are hydrogen, halogen, cyano, nitro, trifluoromethyl, ($C_1$-$C_6$)-alkyl, ($C_3$-$C_8$)-cycloalkyl, ($C_1$-$C_6$)-alkoxy, —O—$[CH_2]_x$—$C_fH_{(2f+1-g)}$—$F_g$, —$OCF_2$—Cl, —O—$CF_2$—CHFCl, ($C_1$-$C_6$)-alkylmercapto, ($C_1$-$C_6$)-hydroxyalkyl, ($C_1$-$C_6$)-alkoxy-($C_1$-$C_6$)-alkoxy, ($C_1$-$C_6$)-alkoxy-($C_1$-$C_6$)-alkyl, ($C_1$-$C_6$)-alkylsulfinyl, ($C_1$-$C_6$)-alkylsulfonyl, ($C_1$-$C_6$)-alkylcarbonyl, ($C_1$-$C_8$)-alkoxycarbonyl, carbamoyl, N—($C_1$-$C_8$)-alkylcarbamoyl, N,N-di-($C_1$-$C_8$)-alkylcarbamoyl, or ($C_7$-$C_{11}$)-aralkylcarbamoyl, optionally substituted by fluorine, chlorine, bromine, trifluoromethyl, ($C_1$-$C_6$)-alkoxy, N—($C_3$-$C_8$)-cycloalkylcarbamoyl, N—($C_3$-$C_8$)-cycloalkyl-($C_1$-$C_4$)-alkylcarbamoyl, ($C_1$-$C_6$)-alkylcarbonyloxy, phenyl, benzyl, phenoxy, benzyloxy, $NR^yR^z$ wherein $R^y$ and $R^z$ are independently selected from hydrogen, ($C_1$-$C_{12}$)-alkyl, ($C_1$-$C_8$)-alkoxy-($C_1$-$C_8$)-alkyl, ($C_7$-$C_{12}$)-aralkoxy-($C_1$-$C_8$)-alkyl, ($C_6$-$C_{12}$)-aryloxy-($C_1$-$C_8$)-alkyl, ($C_3$-$C_{10}$)-cycloalkyl, ($C_3$-$C_{12}$)-alkenyl, ($C_3$-$C_{12}$)-alkynyl, ($C_6$-$C_{12}$)-aryl, ($C_7$-$C_{11}$)-aralkyl, ($C_1$-$C_{12}$)-alkoxy, ($C_7$-$C_{12}$)aralkoxy, ($C_1$-$C_{12}$)-alkylcarbonyl, ($C_3$-$C_8$)-cycloalkylcarbonyl, ($C_6$-$C_{12}$)arylcarbonyl, ($C_7$-$C_{16}$)-aralkylcarbonyl; or further wherein $R^y$ and $R^z$ together are —$[CH2]_h$, in which a $CH_2$ group can be replaced by O, S, N—($C_1$-$C_4$)-alkylcarbonylimino, or N—($C_1$-$C_4$)-alkoxycarbonylimino; phenylmercapto, phenylsulfonyl, phenylsulfinyl, sulfamoyl, N—($C_1$-$C_8$)-alkylsulfamoyl, or N,N-di-($C_1$-$C_8$)-alkylsulfamoyl; or alternatively $R^7$ and $R^8$, $R^8$ and $R^9$, $R^9$ and $R^{10}$, or $R^{10}$ and $R^{11}$, together are a chain selected from —$[CH_2]_n$— or —CH═CH—CH═CH—, where a $CH_2$ group of the chain is optionally replaced by O, S, SO, $SO_2$, or $NR^Y$; and n is 3, 4, or 5; and if E is a heteroaryl radical, said radical can carry 1-3 substituents selected from those defined for $R^7$—$R^{11}$, or if E is a cycloalkyl radical, the radical can carry one substituent selected from those defined for $R^7$—$R^{11}$;

or where, if Q is NR', $R^4$ is alternatively R", where R' and R" are identical or different and are hydrogen, ($C_6$-$C_{12}$)-aryl, ($C_7$-$C_{11}$)-aralkyl, ($C_1$-$C_8$)-alkyl, ($C_1$-$C_8$)-alkoxy-($C_1$-$C_8$)-alkyl, ($C_7$-$C_{12}$)-aralkoxy-($C_1$-$C_8$)-alkyl, ($C_6$-$C_{12}$)-aryloxy-($C_1$-$C_8$)-alkyl, ($C_1$-$C_{10}$)-alkylcarbonyl, optionally substituted ($C_7$-$C_{16}$)-aralkylcarbonyl, or optionally substituted $C_6$-$C_{12}$)-arylcarbonyl; or R' and R" together are —$[CH_2]_h$, in which a $CH_2$ group can be replaced by O, S, N-acylimino, or N—($C_1$-$C_{10}$)-alkoxycarbonylimino, and h is 3 to 7.

Y is N or $CR^3$;

$R^1$, $R^2$ and $R^3$ are identical or different and are hydrogen, hydroxyl, halogen, cyano, trifluoromethyl, nitro, carboxyl, ($C_1$-$C_{20}$)-alkyl, ($C_3$-$C_8$)-cycloalkyl, ($C_3$-$C_8$)cycloalkyl-($C_1$-$C_{12}$)-alkyl, ($C_3$-$C_8$)-cycloalkoxy, ($C_3$-$C_8$)-Cycloalkyl-($C_1$-$C_{12}$)-alkoxy, ($C_3$-$C_8$)-cycloalkoxy-($C_1$-$C_{12}$)-alkyl, ($C_3$-$C_8$)-cycloalkyloxy-($C_1$-$C_{12}$)-alkoxy, ($C_3$-$C_8$)-cycloalkyl-($C_1$-$C_8$)-alkyl-($C_1$-$C_6$)-alkoxy, ($C_3$-$C_8$)-cycloalkyl-($C_1$-$C_8$)-alkoxy-($C_1$-$C_6$)-alkyl, ($C_3$-$C_8$)-cycloalkyloxy-($C_1$-$C_8$)-alkoxy-($C_1$-$C_6$)-alkyl, ($C_3$-$C_8$)-cycloalkoxy-($C_1$-$C_8$)-alkoxy-($C_1$-$C_8$)-alkoxy, ($C_6$-$C_{12}$)-aryl, ($C_7$-$C_{16}$)-aralkyl, ($C_7$-$C_{16}$)-aralkenyl, ($C_7$-$C_{16}$)-aralkynyl, ($C_2$-$C_{20}$)-alkenyl, ($C_2$-$C_{20}$)-alkynyl, ($C_1$-$C_{20}$)-alkoxy, ($C_2$-$C_{20}$)-alkenyloxy, ($C_2$-$C_{20}$)-alkynyloxy, retinyloxy, ($C_1$-$C_{20}$)-alkoxy-($C_1$-$C_{12}$)-alkyl, ($C_1$-$C_{12}$)-alkoxy-($C_1$-$C_{12}$)-alkoxy, ($C_1$-$C_{12}$)-alkoxy-($C_1$-$C_8$)-alkoxy-($C_1$-$C_8$)-alkyl, ($C_6$-$C_{12}$)-aryloxy, ($C_7$-$C_{16}$)-aralkyloxy, ($C_6$-$C_{12}$)-aryloxy-($C_1$-$C_6$)-alkoxy, ($C_7$-$C_{16}$)-aralkoxy-($C_1$-$C_6$)-alkoxy, ($C_1$-$C_{16}$)-hydroxyalkyl, ($C_6$-$C_{16}$)-aryloxy-($C_1$-$C_8$)-alkyl, ($C_7$-$C_{16}$)-aralkoxy-($C_1$-$C_8$)-alkyl, ($C_6$-$C_{12}$)-aryloxy-($C_1$-$C_8$)-alkoxy-($C_1$-$C_6$)-alkyl, ($C_7$-$C_{12}$)-aralkyloxy-($C_1$-$C_8$)-alkoxy-($C_1$-$C_6$)-alkyl, ($C_2$-$C_{20}$)-alkenyloxy-($C_1$-$C_6$)-alkyl, ($C_2$-$C_{20}$)-alkynyloxy-($C_1$-$C_6$)-alkyl, retinyloxy-($C_1$-$C_6$)-alkyl, —O—$[CH_2]_x$$C_fH_{(2f+1-g)}F_g$, —$OCF_2Cl$, —$OCF_2$—CHFCl, ($C_1$-$C_{20}$)-alkylcarbonyl, ($C_3$-$C_8$)-cycloalkylcarbonyl, ($C_6$-$C_{12}$)-arylcarbonyl, ($C_7$-$C_{16}$)- aralkylcarbonyl, cinnamoyl, ($C_2$-$C_{20}$)-alkenylcarbonyl, ($C_2$-$C_{20}$)-alkynylcarbonyl, ($C_1$-$C_{20}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{20}$)-alkenyloxycarbonyl, retinyloxycarbonyl, ($C_2$-$C_{20}$)-alkynyloxycarbonyl, ($C_6$-$C_{12}$)-aryloxy-($C_1$-$C_6$)-alkoxycarbonyl, ($C_7$-$C_{16}$)-aralkoxy-($C_1$-$C_6$)-alkoxycarbonyl, ($C_3$-$C_8$)-cycloalkyl-($C_1$-$C_6$)-alkoxycarbonyl, ($C_3$-$C_8$)-cycloalkoxy-($C_1$-$C_6$)-alkoxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_1$-$C_{12}$)-alkoxy-($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di-($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—(($C_3$-$C_8$)-cycloalkyl-($C_1$-$C_6$)-alkyl)-carbamoyl, N—($C_1$-$C_6$)-alkyl-N—(($C_3$-$C_8$)-cycloalkyl-($C_1$-$C_6$)-alkyl)-carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, N—(($C_1$-$C_{18}$)-alkoxy-($C_1$-$C_{10}$)-alkyl)-carbamoyl, N-(($C_6$-$C_{16}$)-aryloxy-($C_1$-$C_{10}$)-alkyl)-carbamoyl, N-(($C_7$-$C_{16}$)-aralkyloxy-($C_1$-$C_{10}$)-alkyl)-carbamoyl, N—($C_1$-$C_{10}$)-alkyl-N—(($C_1$-$C_{10}$)-alkoxy-($C_1$-$C_{10}$)-alkyl)-carbamoyl, N—($C_1$-$C_{10}$)-alkyl-N—(($C_6$-$C_{12}$)-aryloxy-($C_1$-$C_{10}$)-alkyl)-carbamoyl, N—($C_1$-$C_{10}$)-alkyl-N-(($C_7$-$C_{16}$)-aralkyloxy-($C_1$-$C_{10}$)-alkyl)-carbamoyl; $CON(CH_2)_h$, in which a $CH_2$ group can be replaced by O, S, N—($C_1$-$C_8$)-alkylimino, N—($C_3$-$C_8$)-cycloalkylimino, N—($C_3$-$C_8$)-cycloalkyl-($C_1$-$C_4$)-alkylimino, N—($C_6$-$C_{12}$)-arylimino, N—($C_7$-$C_{16}$)-aralkylimino, N—($C_1$-$C_4$)-alkoxy-($C_1$-$C_6$)-alkylimino, and h is from 3 to 7; a carbamoyl radical of the formula R

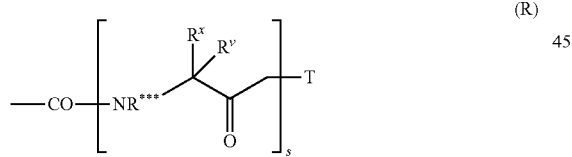

(R)

in which
$R^x$ and $R^y$ are each independently selected from hydrogen, ($C_1$-$C_6$)-alkyl, ($C_3$-$C_7$)-cycloalkyl, aryl, or the substituent of an α-carbon of an α-amino acid, to which the L- and D-amino acids belong,
s is 1-5,
T is OH, or NR*R**, and R*, R and R* are identical or different and are selected from hydrogen, ($C_6$-$C_{12}$)-aryl, ($C_7$-$C_{11}$)-aralkyl, ($C_1$-$C_8$)-alkyl, ($C_3$-$C_8$)-cycloalkyl, (+)-dehydroabietyl, ($C_1$-$C_8$)-alkoxy-($C_1$-$C_8$)-alkyl, ($C_7$-$C_{12}$)-aralkoxy-($C_1$-$C_8$)-alkyl, ($C_6$-$C_{12}$)-aryloxy-($C_1$-$C_8$)-alkyl, ($C_1$-$C_{10}$)-alkanoyl, optionally substituted ($C_7$-$C_{16}$)-aralkanoyl, optionally substituted ($C_6$-$C_{12}$)-aroyl; or R* and R** together are —$[CH_2]_h$, in which a $CH_2$ group can be replaced by O, S, SO, $SO_2$, N-acylamino, N—($C_1$-$C_{10}$)-alkoxycarbonylimino, N—($C_1$-$C_8$)-alkylimino, N—($C_3$-$C_8$)-cycloalkylimino, N—($C_3$-$C_8$)-cycloalkyl-($C_1$-$C_4$)-alkylimino, N—($C_6$-$C_{12}$)-arylimino, N—($C_7$-$C_{16}$)-aralkylimino, N—($C_1$-$C_4$)-alkoxy-($C_1$-$C_6$)-alkylimino, and h is from 3 to 7;
carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)-carbamoyloxy, N—(($C_6$-$C_{12}$)-aryloxy-($C_1$-$C_{10}$)-alkyl)-carbamoyloxy, N—(($C_7$-$C_{16}$)-aralkyloxy-($C_1$-$C_{10}$)-alkyl)-carbamoyloxy, N—($C_1$-$C_{10}$)-alkyl-N—(($C_1$-$C_{10}$)-alkoxy-($C_1$-$C_{10}$)-alkyl)-carbamoyloxy, N—($C_1$-$C_{10}$)-alkyl-N-(($C_6$-$C_{12}$)-aryloxy-($C_1$-$C_{10}$)-alkyl)-carbamoyloxy, N—($C_1$-$C_{10}$)-alkyl-N—(($C_7$-$C_{16}$)-aralkyloxy-($C_1$-$C_{10}$)-alkyl)-carbamoyloxyamino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, ($C_1$-$C_{12}$)-alkanoylamino-($C_1$-$C_8$)-alkyl, ($C_3$-$C_8$)-cycloalkanoylamino-($C_1$-$C_8$)-alkyl, ($C_6$-$C_{12}$)-aroylamino-($C_1$-$C_8$)-alkyl, ($C_7$-$C_{16}$)-aralkanoylamino-($C_1$-$C_8$)-alkyl, amino-($C_1$-$C_{10}$)-alkyl, N—($C_1$-$C_{10}$)-alkylamino-($C_1$-$C_{10}$)-alkyl, N,N-di($C_1$-$C_{10}$)-alkylamino-($C_1$-$C_{10}$)-alkyl, ($C_3$-$C_8$)-cycloalkylamino($C_1$-$C_{10}$)-alkyl, ($C_1$-$C_{20}$)-alkylmercapto, ($C_1$-$C_{20}$)-alkylsulfinyl, ($C_1$-$C_{20}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{12}$)-aralkylsulfonyl, ($C_1$-$C_{12}$)-alkylmercapto-($C_1$-$C_6$)-alkyl, ($C_1$-$C_{12}$)-alkylsulfinyl-($C_1$-$C_6$)-alkyl, ($C_1$-$C_{12}$)-alkylsulfonyl-($C_1$-$C_6$)-alkyl, ($C_6$-$C_{12}$)-arylmercapto-($C_1$-$C_6$)-alkyl, ($C_6$-$C_{12}$)-arylsulfinyl-($C_1$-$C_6$)-alkyl, ($C_6$-$C_{12}$)-arylsulfonyl-($C_1$-$C_6$)-alkyl, ($C_7$-$C_{16}$)-aralkylmercapto-($C_1$-$C_6$)-alkyl, ($C_7$-$C_{16}$)-aralkylsulfinyl-($C_1$-$C_6$)-alkyl, ($C_7$-$C_{16}$)-aralkylsulfonyl-($C_1$-$C_6$)-alkyl, sulfamoyl, N—($C_1$-$C_{10}$)-alkylsulfamoyl, N,N-di-($C_1$-$C_{10}$)-alkylsulfamoyl, ($C_3$-$C_8$)-cycloalkylsulfamoyl, N—($C_6$-$C_{12}$)-arylsulfamoyl, N—($C_7$-$C_{16}$)-aralkylsulfamoyl, N—($C_1$-$C_{10}$)-alkyl-N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, N-(($C_1$-$C_{10}$)-alkyl)-($C_1$-$C_{10}$)-alkylsulfonamido, ($C_7$-$C_{16}$)-aralkylsulfonamido, and N—(($C_1$-$C_{10}$)-alkyl-($C_7$-$C_{16}$)-aralkylsulfonamido;
where an aryl radical may be substituted by 1 to 5 substituents selected from hydroxyl, halogen, cyano, trifluoromethyl, nitro, carboxyl, ($C_2$-$C_{16}$)-alkyl, ($C_3$-$C_8$)-cycloalkyl, ($C_3$-$C_8$)-cycloalkyl-($C_1$-$C_{12}$)-alkyl, ($C_3$-$C_8$)-cycloalkoxy, ($C_3$-$C_8$)-cycloalkyl-($C_1$-$C_{12}$)-alkoxy, ($C_3$-$C_8$)-cycloalkyloxy-($C_1$-$C_{12}$)-alkyl, ($C_3$-$C_8$)-Cycloalkyloxy-($C_1$-$C_{12}$)-alkoxy, ($C_3$-$C_8$)-cycloalkyl-($C_1$-$C_8$)-alkyl-($C_1$-$C_6$)-alkoxy, ($C_3$-$C_8$)-cycloalkyl($C_1$-$C_8$)-alkoxy-($C_1$-$C_6$)-alkyl, ($C_3$-$C_8$)-cycloalkyloxy-($C_1$-$C_8$)-alkoxy-($C_1$-$C_6$)-alkyl, ($C_3$-$C_8$)-cycloalkoxy-($C_1$-$C_8$)-alkoxy-($C_1$-$C_8$)-alkoxy, ($C_6$-$C_{12}$)-aryl, ($C_7$-$C_{16}$)-aralkyl, ($C_2$-$C_{16}$)-alkenyl, ($C_2$-$C_{12}$)-alkynyl, ($C_1$-$C_{16}$)-alkoxy, ($C_1$-$C_{16}$)-alkenyloxy, ($C_1$-$C_{12}$)-alkoxy-($C_1$-$C_{12}$)-alkyl, ($C_1$-$C_{12}$)-alkoxy-($C_1$-$C_{12}$)-alkoxy, ($C_1$-

$C_{12}$)-alkoxy($C_1$-$C_8$)-alkoxy-($C_1$-$C_8$)-alkyl, ($C_6$-$C_{12}$)-aryloxy, ($C_7$-$C_{16}$)-aralkyloxy, ($C_6$-$C_{12}$)-aryloxy-($C_1$-$C_6$)-alkoxy, ($C_7$-$C_{16}$)-aralkoxy-($C_1$-$C_6$)-alkoxy, ($C_1$-$C_8$)-hydroxyalkyl, ($C_6$-$C_{16}$)-aryloxy-($C_1$-$C_8$)-alkyl, ($C_7$-$C_{16}$)-aralkoxy-($C_1$-$C_8$)-alkyl, ($C_6$-$C_{12}$)-aryloxy-($C_1$-$C_8$)-alkoxy-($C_1$-$C_6$)-alkyl, ($C_7$-$C_{12}$)-aralkyloxy-($C_1$-$C_8$)-alkoxy-($C_1$-$C_6$)-alkyl, —O—[$CH_2$]$_x$$C_f$$H_{(2f+1-g)}$$F_g$, —OCF$_2$Cl, —OCF$_2$—CHFCl, ($C_1$-$C_{12}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, ($C_1$-$C_{12}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{12}$)-alkenyloxycarbonyl, ($C_2$-$C_{12}$)-alkynyloxycarbonyl, ($C_6$-$C_{12}$)-aryloxy-($C_1$-$C_6$)-alkoxycarbonyl, ($C_7$-$C_{16}$)-aralkoxy-($C_1$-$C_6$)-alkoxycarbonyl, ($C_3$-$C_8$)-cycloalkyl-($C_1$-$C_6$)-alkoxycarbonyl, ($C_3$-$C_8$)-cycloalkoxy-($C_1$-$C_6$)-alkoxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_1$-$C_{12}$)-alkoxy-($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—(($C_3$-$C_8$)-cycloalkyl-($C_1$-$C_6$)-alkyl)carbamoyl, N—($C_1$-$C_6$)-alkyl-N—(($C_3$-$C_8$)-cycloalkyl-($C_1$-$C_6$)-alkyl)carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, N—(($C_1$-$C_{16}$)-alkoxy-($C_1$-$C_{10}$)-alkyl)carbamoyl, N—(($C_6$-$C_{16}$)-aryloxy-($C_1$-$C_{10}$)-alkyl)carbamoyl, N—(($C_7$-$C_{16}$)-aralkyloxy-($C_1$-$C_{10}$)-alkyl)carbamoyl, N—($C_1$-$C_{10}$)-alkyl-N-(($C_1$-$C_{10}$)-alkoxy-($C_1$-$C_{10}$)-alkyl)carbamoyl, N—($C_1$-$C_{10}$)-alkyl-N-(($C_6$-$C_{12}$)-aryloxy-($C_1$-$C_{10}$)-alkyl)carbamoyl, N—($C_1$-$C_{10}$)-alkyl-N-(($C_7$-$C_{16}$)-aralkyloxy-($C_1$-$C_{10}$)-alkyl)-carbamoyl, CON(CH$_2$)$_h$, in which a CH$_2$ group can be replaced by, O, S, N—($C_1$-$C_8$)-alkylimino, N—($C_3$-$C_8$)-cycloalkylimino, N—($C_3$-$C_8$)-cycloalkyl-($C_1$-$C_4$)-alkylimino, N—($C_6$-$C_{12}$)-arylimino, N—($C_7$-$C_{16}$)-aralkylimino, N—($C_1$-$C_4$)-alkoxy-($C_1$-$C_6$)-alkylimino, and h is from 3 to 7; carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{16}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)carbamoyloxy, N—(($C_6$-$C_{12}$)-aryloxy-($C_1$-$C_{10}$)-alkyl)carbamoyloxy, N—(($C_7$-$C_{16}$)-aralkyloxy-($C_1$-$C_{10}$)-alkyl)carbamoyloxy, N—($C_1$-$C_{10}$)-alkyl-N-(($C_1$-$C_{10}$)-alkoxy-($C_1$-$C_{10}$)-alkyl)carbamoyloxy, N—($C_1$-$C_{10}$)-alkyl-N-(($C_6$-$C_{12}$)-aryloxy-($C_1$-$C_{10}$)-alkyl)carbamoyloxy, N—($C_1$-$C_{10}$)-alkyl-N-(($C_7$-$C_{16}$)-aralkyloxy-($C_1$-$C_{10}$)-alkyl)carbamoyloxy, amino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N-$C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, ($C_1$-$C_{12}$)-alkanoylamino-($C_1$-$C_8$)-alkyl, ($C_3$-$C_8$)-cycloalkanoylamino-($C_1$-$C_8$)-alkyl, ($C_6$-$C_{12}$)-aroylamino-($C_1$-$C_8$)-alkyl, ($C_7$-$C_{16}$)-aralkanoylamino-($C_1$-$C_8$)-alkyl, amino-($C_1$-$C_{10}$)-alkyl, N—($C_1$-$C_{10}$)-alkylamino-($C_1$-$C_{10}$)-alkyl, N,N-di-($C_1$-$C_{10}$)-alkylamino-($C_1$-$C_{10}$)-alkyl, ($C_3$-$C_8$)-cycloalkylamino-($C_1$-$C_{10}$)-alkyl, ($C_1$-$C_{12}$)-alkylmercapto, ($C_1$-$C_{12}$)-alkylsulfinyl, ($C_1$-$C_{12}$)-alkylsulfonyl, ($C_6$-$C_{16}$)-arylmercapto, ($C_6$-$C_{16}$)-arylsulfinyl, ($C_6$-$C_{16}$)-arylsulfonyl, ($C_7$-$C_{16}$)-aralkylmercapto, ($C_7$-$C_{16}$)-aralkylsulfinyl, or ($C_7$-$C_{16}$)-aralkylsulfonyl;

or wherein $R^1$ and $R^2$, or $R^2$ and $R^3$ form a chain [CH$_2$]$_o$, which is saturated or unsaturated by a C=C double bond, in which 1 or 2 CH$_2$ groups are optionally replaced by O, S, SO, SO$_2$, or NR', and R' is hydrogen, ($C_6$-$C_{12}$)-aryl, ($C_1$-$C_8$)-alkyl, ($C_1$-$C_8$)-alkoxy-($C_1$-$C_8$)-alkyl, ($C_7$-$C_{12}$)-aralkoxy-($C_1$-$C_8$)-alkyl, ($C_6$-$C_{12}$)-aryloxy-($C_1$-$C_8$)-alkyl, ($C_1$-$C_{10}$)-alkanoyl, optionally substituted ($C_7$-$C_{16}$)-aralkanoyl, or optionally substituted ($C_6$-$C_{12}$)-aroyl; and o is 3, 4 or 5;

or wherein the radicals $R^1$ and $R^2$, or $R^2$ and $R^3$, together with the pyridine or pyridazine carrying them, form a 5,6,7,8-tetrahydroisoquinoline ring, a 5,6,7,8-tetrahydroquinoline ring, or a 5,6,7,8-tetrahydrocinnoline ring;

or wherein $R^1$ and $R^2$, or $R^2$ and $R^3$ form a carbocyclic or heterocyclic 5- or 6-membered aromatic ring;

or where $R^1$ and $R^2$, or $R^2$ and $R^3$, together with the pyridine or pyridazine carrying them, form an optionally substituted heterocyclic ring systems selected from thienopyridines, furanopyridines, pyridopyridines, pyrimidinopyridines, imidazopyridines, thiazolopyridines, oxazolopyridines, quinoline, isoquinoline, and cinnoline; where quinoline, isoquinoline or cinnoline preferably satisfy the formulae Ia, Ib and Ic:

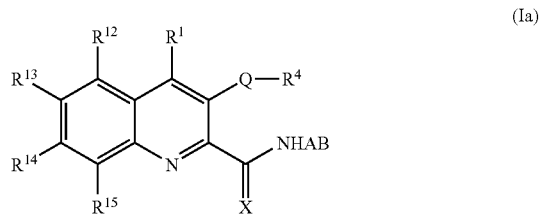

(Ia)

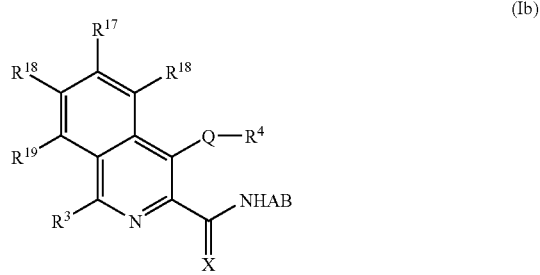

(Ib)

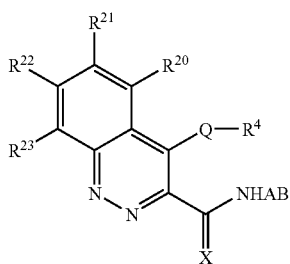
(Ic)

and the substituents $R^{12}$ to $R^{23}$ in each case independently of each other have the meaning of $R^1$, $R^2$ and $R^3$; or wherein the radicals $R^1$ and $R^2$, together with the pyridine carrying them, form a compound of Formula Id:

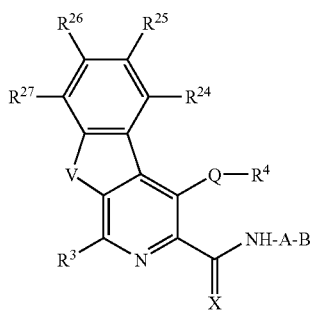
(Id)

where

V is S, O, or $NR^k$, and $R^k$ is selected from hydrogen, $(C_1\text{-}C_6)$-alkyl, aryl, or benzyl; where an aryl radical may be optionally substituted by 1 to 5 substituents as defined above; and $R^{24}$, $R^{25}$, $R^{26}$, and $R^{27}$ in each case independently of each other have the meaning of $R^1$, $R^2$ and $R^3$;

f is 1 to 8;

g is 0 or 1 to (2f+1);

x is 0 to 3; and h is 3 to 7;

including the physiologically active salts and prodrugs derived therefrom.

Exemplary compounds according to Formula I are described in European Patent Nos. EP0650960 and EP0650961. All compounds listed in EP0650960 and EP0650961, in particular, those listed in the compound claims and the final products of the working examples, are hereby incorporated into the present application by reference herein. Additionally, exemplary compounds according to Formula I are described in U.S. Pat. No. 5,658,933. All compounds listed in U.S. Pat. No. 5,658,933, in particular, those listed in the compound claims and the final products of the working examples, are hereby incorporated into the present application by reference herein.

Additional compounds according to Formula I are substituted heterocyclic carboxyamides described in U.S. Pat. No. 5,620,995; 3-hydroxypyridine-2-carboxamidoesters described in U.S. Pat. No. 6,020,350; sulfonamidocarbonylpyridine-2-carboxamides described in U.S. Pat. No. 5,607,954; and sulfonamidocarbonyl-pyridine-2-carboxamides and sulfonamidocarbonyl-pyridine-2-carboxamide esters described in U.S. Pat. Nos. 5,610,172 and 5,620,996. All compounds listed in these patents, in particular, those compounds listed in the compound claims and the final products of the working examples, are hereby incorporated into the present application by reference herein.

Exemplary compounds according to Formula Ia are described in U.S. Pat. Nos. 5,719,164 and 5,726,305. All compounds listed in the foregoing patents, in particular, those listed in the compound claims and the final products of the working examples, are hereby incorporated into the present application by reference herein. Exemplary compounds according to Formula Ib are described in U.S. Pat. No. 6,093,730. All compounds listed in U.S. Pat. No. 6,093,730, in particular, those listed in the compound claims and the final products of the working examples, are hereby incorporated into the present application by reference herein Additionally, compounds related to Formula I that can also be used in the methods of the invention include, but are not limited to, 6-cyclohexyl-1-hydroxy-4-methyl-1H-pyridin-2-one (Compound N), 7-(4-methyl-piperazin-1-ylmethyl)-5-phenylsulfanylmethyl-quinolin-8-ol (Compound D), 4-nitro-quinolin-8-ol (Compound E), and 5-butoxymethyl-quinolin-8-ol (Compound F). Further, the invention provides additional exemplary compounds wherein, e.g., position A and B together may be, e.g., hexanoic acid, cyanomethyl, 2-aminoethyl, benzoic acid, 1H-benzoimidazol-2-ylmethyl, etc.

In certain embodiments, compounds used in the methods of the invention are pyridine-2-carboxamides. In one embodiment, the compound is selected from a compound of the Formula I wherein A is —$CR^5R^6$—, and $R^5$ and $R^6$ are each independently selected from the group consisting of hydrogen, $(C_1\text{-}C_6)$-alkyl, $(C_3\text{-}C_7)$-cycloalkyl, aryl, or a substituent of the α-carbon atom of an α-amino acid, wherein the amino acid is a natural L-amino acid or its D-isomer;

B is —$CO_2H$ or a $CO_2$-G carboxyl radical, where G is a radical of an alcohol G-OH in which G is selected from the group consisting of $(C_1\text{-}C_{20})$-alkyl radical, $(C_3\text{-}C_8)$ cycloalkyl radical, $(C_2\text{-}C_{20})$-alkenyl radical, $(C_3\text{-}C_8)$-cycloalkenyl radical, retinyl radical, $(C_2\text{-}C_{20})$-alkynyl radical, $(C_4\text{-}C_{20})$-alkenynyl radical;

X is O;

Q is O;

$R^4$ is selected from the group consisting of hydrogen, $(C_1\text{-}C_{10})$-alkyl, $(C_2\text{-}C_{10})$-alkenyl, $(C_2\text{-}C_{10})$-alkynyl, wherein alkenyl or alkynyl contains one or two C—C multiple bonds; unsubstituted fluoroalkyl radical of the formula —$[CH_2]_x$—$C_fH_{(2f+1-g)}$—$F_g$, aryl, heteroaryl, and $(C_7\text{-}C_{11})$-aralkyl;

Y is $CR^3$;

$R^1$, $R^2$ and $R^3$ are identical or different and are selected from the group consisting of hydrogen, hydroxyl, halogen, cyano, trifluoromethyl, nitro, carboxyl; $(C_1\text{-}C_{20})$-alkyl, $(C_3\text{-}C_8)$-cycloalkyl, $(C_3\text{-}C_8)$-cycloalkoxy, $(C_6\text{-}C_{12})$-aryl, $(C_7\text{-}C_{16})$-aralkyl, $(C_7\text{-}C_{16})$-aralkenyl, $(C_7\text{-}C_{16})$-aralkynyl, $(C_2\text{-}C_{20})$-alkenyl, $(C_2\text{-}C_{20})$-alkynyl, $(C_1\text{-}C_{20})$-alkoxy, $(C_2\text{-}C_{20})$-alkenyloxy, $(C_2\text{-}C_{20})$-alkynyloxy, retinyloxy, $(C_6\text{-}C_{12})$-aryloxy, $(C_7\text{-}C_{16})$-aralkyloxy, $(C_1\text{-}C_{16})$-hydroxyalkyl, —O—$[CH_2]_xC_fH_{(2f+1-g)}F_g$, —$OCF_2Cl$, —$OCF_2$—$CHFCl$, $(C_1\text{-}C_{20})$-alkylcarbonyl, $(C_3\text{-}C_8)$-cycloalkylcarbonyl, $(C_6\text{-}C_{12})$-arylcarbonyl, $(C_7\text{-}C_{16})$-aralkylcarbonyl, cinnamoyl, $(C_2\text{-}C_{20})$-alkenylcarbonyl, $(C_2\text{-}C_{20})$-alkynylcarbonyl, $(C_1\text{-}C_{20})$-alkoxycarbonyl, $(C_6\text{-}C_{12})$-aryloxycarbonyl, $(C_7\text{-}C_{16})$-aralkoxycarbonyl, $(C_3\text{-}C_8)$-cycloalkoxycarbonyl, $(C_2\text{-}C_{20})$-alkenyloxycarbonyl, retinyloxycarbonyl, $(C_2\text{-}C_{20})$-alkynyloxycarbonyl, $(C_1\text{-}C_{12})$-alkylcarbonyloxy, $(C_3\text{-}C_8)$-cycloalkylcarbonyloxy, $(C_6\text{-}C_{12})$- arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy, $(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy, carbamoyl, N—$(C_1-C_{12})$-alkylcarbamoyl, N,N-di-$(C_1-C_{12})$-alkylcarbamoyl, N—$(C_3-C_8)$-cycloalkylcarbamoyl, N,N-dicyclo-$(C_3-C_8)$-alkylcarbamoyl, N—$(C_1-C_{10})$-alkyl-N—$(C_3-C_8)$-cycloalkylcarbamoyl, N—$((C_3-C_8)$-cycloalkyl-$(C_1-C_6)$-alkyl)carbamoyl, N—$(C_1-C_6)$-alkyl-N-$((C_3-C_8)$-cycloalkyl-$(C_1-C_6)$-alkyl)carbamoyl, N-(+)-dehydroabietylcarbamoyl, N—$(C_1-C_6)$-alkyl-N-(+)-dehydroabietylcarbamoyl, N—$(C_6-C_{12})$-arylcarbamoyl, N—$(C_7-C_{16})$-aralkylcarbamoyl, N—$(C_1-C_{10})$-alkyl-N—$(C_6-C_{16})$-arylcarbamoyl, N—$(C_1-C_{10})$-alkyl-N—$(C_7-C_{16})$-aralkylcarbamoyl, N—$((C_1-C_{16})$-alkoxy-$(C_1-C_{10})$-alkyl)carbamoyl, N—$((C_6-C_{16})$-aryloxy-$(C_1-C(C_{10}))$-alkyl)carbamoyl, N-$((C_7-C_{16})$-aralkyloxy-$(C_1-C_{10})$-alkyl)carbamoyl, N—$(C_1-C_{10})$-alkyl-N-$((C_1-C_1)$-alkoxy-$(C_1-C_{10})$-alkyl)carbamoyl, N—$(C_1-C_{10})$-alkyl-N-$((C_6-C_{12})$-aryloxy-$(C_1-C_{10})$-alkyl)carbamoyl, N—$(C_1-C_{10})$-alkyl-N—$((C_7-C_{16})$-aralkyloxy-$(C_1-C_{10})$-alkyl)-carbamoyl, carbamoyloxy, N—$(C_1-C_{12})$-alkylcarbamoyloxy, N,N-di-$(C_1-C_{12})$-alkylcarbamoyloxy, N—$(C_3-C_8)$-cycloalkylcarbamoyloxy, N—$(C_6-C_{12})$-arylcarbamoyloxy, N—$(C_7-C_{16})$-aralkylcarbamoyloxy, N—$(C_1-C_{10})$-alkyl-N—$(C_6-C_{12})$-arylcarbamoyloxy, N—$(C_1-C_{10})$-alkyl-N—$(C_7-C_{16})$-aralkylcarbamoyloxy, N—$((C_1-C_{10})$-alkyl)-carbamoyloxy, N—$(C_1-C_{10})$-alkyl-N—$((C_7-C_{16})$-aralkyloxy-$(C_1-C_{10})$-alkyl)-carbamoyloxyamino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N—$(C_6-C_{12})$-arylamino, N—$(C_7-C_{11})$-aralkylamino, N-alkyl-aralkylamino, N-alkyl-arylamino, $(C_1-C_{12})$-alkoxyamino, $(C_1-C_{12})$-alkoxy-N—$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N—$(C_1-C_{10})$-alkylamino, $(C_3-C_8)$-cycloalkanoyl-N—$(C_1-C_{10})$-alkylamino, $(C_6-C_{12})$-aroyl-N—$(C_1-C_{10})$-alkylamino, $(C_7-C_{11})$-aralkanoyl-N—$(C_1-C_{10})$-alkylamino, amino-$(C_1-C_{10})$-alkyl, $(C_1-C_{20})$-alkylmercapto, $(C_1-C_{20})$-alkylsulfinyl, $(C_1-C_{20})$-alkylsulfonyl, $(C_6-C_{12})$-arylmercapto, $(C_6-C_{12})$-arylsulfinyl, $(C_6-C_{12})$-arylsulfonyl, $(C_7-C_{16})$-aralkylmercapto, $(C_7-C_{16})$-aralkylsulfinyl, $(C_7-C_{16})$-aralkylsulfonyl, sulfamoyl, N—$(C_1-C_{10})$-alkylsulfamoyl, N,N-di-$(C_1-C_{10})$-alkylsulfamoyl, $(C_3-C_8)$-cycloalkylsulfamoyl, N—$(C_6-C_{12})$-arylsulfamoyl, N—$(C_7-C_{16})$-aralkylsulfamoyl, N—$(C_1-C_{10})$-alkyl-N—$(C_6-C_{12})$-arylsulfamoyl, N—$(C_1-C_{10})$-alkyl-N—$(C_7-C_{16})$-aralkylsulfamoyl, $(C_1-C_{10})$-alkylsulfonamido, $(C_7-C_{16})$-aralkylsulfonamido, and N-$((C_1-C_{10})$-alkyl-$(C_7-C_{16})$-aralkylsulfonamido; where an aryl radical may be substituted by 1 to 5 substituents selected from hydroxyl, halogen, cyano, trifluoromethyl, nitro, carboxyl, $(C_2-C_{16})$-alkyl, $(C_3-C_8)$-cycloalkyl, $(C_3-C_8)$-cycloalkoxy, $(C_6-C_{12})$-aryl, $(C_7-C_{16})$-aralkyl, $(C_2-C_{16})$-alkenyl, $(C_2-C_{12})$-alkynyl, $(C_1-C_{16})$-alkoxy, $(C_1-C_{16})$-alkylamino, $(C_6-C_{12})$-aryloxy, $(C_7-C_{16})$-aralkyloxy, $(C_1-C_8)$-hydroxyalkyl, —O—$[CH_2]_xC_fH_{(2f+1-g)}F_g$, —OCF$_2$Cl, and —OCF$_2$—CHFCl;

x is 0 to 3;

f is 1 to 8; and g is 0 or 1 to (2f+1);

including the physiologically active salts and prodrugs derived therefrom.

Pyridine-2-carboxamides of Formula I include, but are not limited to, [(3-methoxy-pyridine-2-carbonyl)-amino]-acetic acid, 3-methoxypyridine-2-carboxylic acid N-(((hexadecyloxy)-carbonyl)-methyl)-amide hydrochloride, 3-methoxypyridine-2-carboxylic acid N-(((1-octyloxy)-carbonyl)-methyl)-amide, 3-methoxypyridine-2-carboxylic acid N-(((hexyloxy)-carbonyl)-methyl)-amide, 3-methoxypyridine-2-carboxylic acid N-(((butyloxy)-carbonyl)-methyl)-amide, 3-methoxypyridine-2-carboxylic acid N-(((2-nonyloxy)-carbonyl)-methyl)-amide racemate, 3-methoxypyridine-2-carboxylic acid N-(((heptyloxy)-carbonyl)-methyl)-amide, 3-benzyloxypyridine-2-carboxylic acid N-(((octyloxy)-carbonyl)-methyl)-amide, 3-benzyloxypyridine-2-carboxylic acid N-(((butyloxy)-carbonyl)-methyl)-amide, 5-(((3-(1-butyloxy)-propyl)-amino)-carbonyl)-3-methoxypyridine-2-carboxylic acid N-((benzyloxycarbonyl)-methyl)-amide, 5-(((3-(1-butyloxy)-propyl)-amino)-carbonyl)-3-methoxypyridine-2-carboxylic acid N-(((1-butyloxy)-carbonyl)-methyl)-amide, 5-(((3-lauryloxy)-propyl)amino)-carbonyl)-3-methoxypyridine-2-carboxylic acid N-(((benzyloxy)-carbonyl)-methyl)-amide, [(3-hydroxy-pyridine-2-carbonyl)-amino]-acetic acid (Compound G), and [(3-methoxy-pyridine-2-carbonyl)-amino]-acetic acid (Compound P).

In certain embodiments, compounds used in the methods of the invention are quinoline-2-carboxamides. In one embodiment, the compound is selected from a compound of the Formula Ia wherein A is —CR$^5$R$^6$—, and R$^5$ and R$^6$ are each independently selected from the group consisting of hydrogen, $(C_1-C_6)$-alkyl, $(C_3-C_7)$-cycloalkyl, aryl, or a substituent of the α-carbon atom of an α-amino acid, wherein the amino acid is a natural L-amino acid or its D-isomer;

B is —CO$_2$H or a CO$_2$-G carboxyl radical, where G is a radical of an alcohol G-OH in which G is selected from the group consisting of $(C_1-C_{20})$-alkyl radical, $(C_3-C_8)$ cycloalkyl radical, $(C_2-C_{20})$-alkenyl radical, $(C_3-C_8)$-cycloalkenyl radical, retinyl radical, $(C_2-C_{20})$-alkynyl radical, $(C_4-C_{20})$-alkynyl radical;

X is O;

Q is O;

R$^4$ is selected from the group consisting of hydrogen, $(C_1-C_{10})$-alkyl, $(C_2-C_{10})$-alkenyl, $(C_2-C_{10})$-alkynyl, wherein alkenyl or alkynyl contains one or two C—C multiple bonds; unsubstituted fluoroalkyl radical of the formula —$[CH_2]_x$—$C_fH_{(2f+1-g)}$—$F_g$, aryl, heteroaryl, and $(C_7-C_{11})$-aralkyl;

R$^1$, R$^{12}$, R$^{13}$, R$^{14}$ and R$^{15}$ are identical or different and are selected from the group consisting of hydrogen, hydroxyl, halogen, cyano, trifluoromethyl, nitro, carboxyl; $(C_1-C_{20})$-alkyl, $(C_3-C_8)$-cycloalkyl, $(C_3-C_8)$-cycloalkoxy, $(C_6-C_{12})$-aryl, $(C_7-C_{16})$-aralkyl, $(C_7-C_{16})$-aralkenyl, $(C_7-C_{16})$-aralkynyl, $(C_2-C_{20})$-alkenyl, $(C_2-C_{20})$-alkynyl, $(C_1-C_{20})$-alkoxy, $(C_2-C_{20})$-alkenyloxy, $(C_2-C_{20})$-alkynyloxy, retinyloxy, $(C_6-C_{12})$-aryloxy, $(C_7-C_{16})$-aralkyloxy, $(C_1-C_{16})$-hydroxyalkyl, —O—$[CH_2]_xCfH_{(2f+1-g)}F_g$, —OCF$_2$Cl, —OCF$_2$—CHFCl, $(C_1-C_{20})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_2-C_{20})$-alkenylcarbonyl, $(C_2-C_{20})$-alkynylcarbonyl, $(C_1-C_{20})$-alkoxycarbonyl, $(C_6-C_{12})$-aryloxycarbonyl, $(C_7-C_{16})$-aralkoxycarbonyl, $(C_3-C_8)$- cycloalkoxycarbonyl, $(C_2-C_{20})$-alkenyloxycarbonyl, retinyloxycarbonyl, $(C_2-C_{20})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy, $(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy, carbamoyl, N—$(C_1-C_{12})$-alkylcarbamoyl, N,N-di-$(C_1-C_{12})$-alkylcarbamoyl, N—$(C_3-C_8)$-cycloalkylcarbamoyl, N,N-dicyclo-$(C_3-C_8)$-alkylcarbamoyl, N—$(C_1-C_{10})$-alkyl-N—$(C_3-C_8)$-cycloalkylcarbamoyl, N—$((C_3-C_8)$-cycloalkyl-$(C_1-C_6)$-alkyl)-carbamoyl, N-(+)-dehydroabietylcarbamoyl, N—$(C_1-C_6)$-alkyl-N-(+)-dehydroabietylcarbamoyl, N—$(C_6-C_{12})$-arylcarbamoyl, N—$(C_7-C_{16})$-aralkylcarbamoyl, N—$(C_1-C_{10})$-alkyl-N—$(C_6-C_{16})$-arylcarbamoyl, N—$(C_1-C_{10})$-alkyl-N—$(C_7-C_{16})$-aralkylcarbamoyl, carbamoyloxy, N—$(C_1-C_{12})$-alkylcarbamoyloxy, N,N-di-$(C_1-C_{12})$-alkylcarbamoyloxy, N—$(C_3-C_8)$-cycloalkylcarbamoyloxy, N—$(C_6-C_{12})$-arylcarbamoyloxy, N—$(C_7-C_{16})$-aralkylcarbamoyloxy, N—$(C_1-C_{10})$-alkyl-N—$(C_6-C_{12})$-arylcarbamoyloxy, N—$(C_1-C_{10})$-alkyl-N—$(C_7-C_{16})$-aralkylcarbamoyloxy, N—$((C_1-C_{10})$-alkyl)-carbamoyloxy, N—$(C_1-C_{10})$-alkyl-N—$((C_7-C_{16})$-aralkyloxy-$(C_1-C_{10})$-alkyl)-carbamoyloxyamino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N—$(C_6-C_{12})$-arylamino, N—$(C_7-C_{11})$-aralkylamino, N-alkyl-aralkylamino, N-alkyl-arylamino, $(C_1-C_{12})$-alkoxyamino, $(C_1-C_{12})$-alkoxy-N—$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N—$(C_1-C_{10})$-alkylamino, $(C_3-C_8)$-cycloalkanoyl-N—$(C_1-C_{10})$-alkylamino, $(C_6-C_{12})$-aroyl-N—$(C_1-C_{10})$-alkylamino, $(C_7-C_{11})$-aralkanoyl-N—$(C_1-C_{10})$-alkylamino, amino-$(C_1-C_{10})$-alkyl, $(C_1-C_{20})$-alkylmercapto, $(C_1-C_{20})$-alkylsulfinyl, $(C_1-C_{20})$-alkylsulfonyl, $(C_6-C_{12})$-arylmercapto, $(C_6-C_{12})$-arylsulfinyl, $(C_6-C_{12})$-arylsulfonyl, $(C_7-C_{16})$-aralkylmercapto, $(C_7-C_{16})$-aralkylsulfinyl, $(C_7-C_{16})$-aralkylsulfonyl, sulfamoyl, N—$(C_1-C_{10})$-alkylsulfamoyl, N,N-di-$(C_1-C_{10})$-alkylsulfamoyl, $(C_3-C_8)$-cycloalkylsulfamoyl, N—$(C_6-C_{12})$-arylsulfamoyl, N—$(C_7-C_{16})$-aralkylsulfamoyl, N—$(C_1-C_{10})$-alkyl-N—$(C_6-C_{12})$-arylsulfamoyl, N—$(C_1-C_{10})$-alkyl-N—$(C_7-C_{16})$-aralkylsulfamoyl, $(C_1-C_{10})$-alkylsulfonamido, $(C_7-C_{16})$-aralkylsulfonamido, and N-$((C_1-C_{10})$-alkyl-$(C_7-C_{16})$-aralkylsulfonamido; where an aryl radical may be substituted by 1 to 5 substituents selected from hydroxyl, halogen, cyano, trifluoromethyl, nitro, carboxyl, $(C_2-C_{16})$-alkyl, $(C_3-C_8)$-cycloalkyl, $(C_3-C_8)$-cycloalkoxy, $(C_6-C_{12})$-aryl, $(C_7-C_{16})$-aralkyl, $(C_2-C_{16})$-alkenyl, $(C_2-C_{12})$-alkynyl, $(C_1-C_{16})$-alkoxy, $(C_1-C_{16})$-alkenyloxy, $(C_6-C_{12})$-aryloxy, $(C_7-C_{16})$-aralkyloxy, $(C_1-C_8)$-hydroxyalkyl, —O—$[CH_2]_xC_fH_{(2f+1-g)}F_g$, —$OCF_2Cl$, and —$OCF_2$—$CHFCl$;

x is 0 to 3;

f is 1 to 8; and g is 0 or 1 to (2f+1);

including the physiologically active salts and prodrugs derived therefrom.

Quinoline-2-carboxamides of Formula Ia include, but are not limited to, N-((3-Hydroxy-6-isopropoxy-quinoline-2-carbonyl)-amino)-acetic acid (Compound H), N-((6-(1-butyloxy)-3-hydroxyquinolin-2-yl)-carbonyl)-glycine, [(3-hydroxy-6-trifluoromethoxy-quinoline-2-carbonyl)-amino]-acetic acid (Compound I), N-((7-chloro-3-hydroxyquinolin-2-yl)-carbonyl)-glycine, and [(6-chloro-3-hydroxy-quinoline-2-carbonyl)-amino]-acetic acid (Compound O).

In certain embodiments, compounds used in the methods of the invention are isoquinoline-3-carboxamides. In one embodiment, the compound is selected from a compound of the Formula Ib wherein A is —$CR^5R^6$—, and $R^5$ and $R^6$ are each independently selected from the group consisting of hydrogen, $(C_1-C_6)$-alkyl, $(C_3-C_7)$-cycloalkyl, aryl, or a substituent of the α-carbon atom of an α-amino acid, wherein the amino acid is a natural L-amino acid or its D-isomer;

B is —$CO_2H$ or a $CO_2$-G carboxyl radical, where G is a radical of an alcohol G-OH in which G is selected from the group consisting of $(C_1-C_{20})$-alkyl radical, $(C_3-C_8)$ cycloalkyl radical, $(C_2-C_{20})$-alkenyl radical, $(C_3-C_8)$-cycloalkenyl radical, retinyl radical, $(C_2-C_{20})$-alkynyl radical, $(C_4-C_{20})$-alkenynyl radical;

X is O;

Q is O;

$R^4$ is selected from the group consisting of hydrogen, $(C_1-C_{10})$-alkyl, $(C_2-C_{10})$-alkenyl, $(C_2-C_{10})$-alkynyl, wherein alkenyl or alkynyl contains one or two C—C multiple bonds; unsubstituted fluoroalkyl radical of the formula —$[CH_2]_x$—$C_fH_{(2f+1-g)}$—$F_g$, aryl, heteroaryl, and $(C_7-C_{11})$-aralkyl;

$R^3$, $R^{16}$, $R^{17}$, $R^{18}$ and $R^{19}$ are identical or different and are selected from the group consisting of hydrogen, hydroxyl, halogen, cyano, trifluoromethyl, nitro, carboxyl; $(C_1-C_{20})$-alkyl, $(C_3-C_8)$-cycloalkyl, $(C_3-C_8)$-cycloalkoxy, $(C_6-C_{12})$-aryl, $(C_7-C_{16})$-aralkyl, $(C_7-C_{16})$-aralkenyl, $(C_7-C_{16})$-aralkynyl, $(C_2-C_{20})$-alkenyl, $(C_2-C_{20})$-alkynyl, $(C_1-C_{20})$-alkoxy, $(C_2-C_{20})$-alkenyloxy, $(C_2-C_{20})$-alkynyloxy, retinyloxy, $(C_6-C_{12})$-aryloxy, $(C_7-C_{16})$-aralkyloxy, $(C_1-C_{16})$-hydroxyalkyl, —O—$[CH_2]_xCfH_{(2f+1-g)}F_g$, —$OCF_2Cl$, —$OCF_2$—$CHFCl$, $(C_1-C_{20})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_2-C_{20})$-alkenylcarbonyl, $(C_2-C_{20})$-alkynylcarbonyl, $(C_1-C_{20})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{20})$-alkenyloxycarbonyl, retinyloxycarbonyl, $(C_2-C_{20})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy, $(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy, carbamoyl, N—$(C_1-C_{12})$-alkylcarbamoyl, N,N-di-$(C_1-C_{12})$-alkylcarbamoyl, N—$(C_3-C_8)$-cycloalkylcarbamoyl, N,N-dicyclo-$(C_3-C_8)$-alkylcarbamoyl, N—$(C_1-C_{10})$-alkyl-N—$(C_3-C_8)$-cycloalkylcarbamoyl, N—$((C_3-C_8)$-cycloalkyl-$(C_1-C_6)$-alkyl)-carbamoyl, N-(+)-dehydroabietylcarbamoyl, N—$(C_1-C_6)$-alkyl-N-(+)-dehydroabietylcarbamoyl, N—$(C_6-C_{12})$-arylcarbamoyl, N—$(C_7-C_{16})$-aralkylcarbamoyl, N—$(C_1-C_{10})$-alkyl-N—$(C_6-C_{16})$-arylcarbamoyl, N—$(C_1-C_{10})$-alkyl-N—$(C_7-C_{16})$-aralkylcarbamoyl, carbamoyloxy, N—$(C_1-C_{12})$-alkylcarbamoyloxy, N,N-di-$(C_1-C_{12})$-alkylcarbamoyloxy, N—$(C_3-C_8)$-cycloalkylcarbamoyloxy, N—$(C_6-C_{12})$-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N-(($C_1$-$C_{10}$)-alkyl)-carbamoyloxy, N—($C_1$-$C_{10}$)-alkyl-N-(($C_7$-$C_{16}$)-aralkyloxy-($C_1$-$C_{10}$)-alkyl)-carbamoyloxyamino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, amino-($C_1$-$C_{10}$)-alkyl, ($C_1$-$C_{20}$)-alkylmercapto, ($C_1$-$C_{20}$)-alkylsulfinyl, ($C_1$-$C_{20}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{16}$)-aralkylsulfonyl, sulfamoyl, N—($C_1$-$C_{10}$)-alkylsulfamoyl, N,N-di-($C_1$-$C_{10}$)-alkylsulfamoyl, ($C_3$-$C_8$)-cycloalkylsulfamoyl, N—($C_6$-$C_{12}$)-arylsulfamoyl, N—($C_7$-$C_{16}$)-aralkylsulfamoyl, N—($C_1$-$C_{10}$)-alkyl-N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, ($C_7$-$C_{16}$)-aralkylsulfonamido, and N-(($C_1$-$C_{10}$)-alkyl-($C_7$-$C_{16}$)-aralkylsulfonamido; where an aryl radical may be substituted by 1 to 5 substituents selected from hydroxyl, halogen, cyano, trifluoromethyl, nitro, carboxyl, ($C_2$-$C_{16}$)-alkyl, ($C_3$-$C_8$)-cycloalkyl, ($C_3$-$C_8$)-cycloalkoxy, ($C_6$-$C_{12}$)-aryl, ($C_7$-$C_{16}$)-aralkyl, ($C_2$-$C_{16}$)-alkenyl, ($C_2$-$C_{12}$)-alkynyl, ($C_1$-$C_{16}$)-alkoxy, ($C_1$-$C_{16}$)-alkenyloxy, ($C_6$-$C_{12}$)-aryloxy, ($C_7$-$C_{16}$)-aralkyloxy, ($C_1$-$C_8$)-hydroxyalkyl, —O—[$CH_2$]$_x$$C_f$$H_{(2f+1-g)}$$F_g$, —$OCF_2Cl$, and —$OCF_2$—CHFCl;

x is 0 to 3;

f is 1 to 8; and g is 0 or 1 to (2f+1);

including the physiologically active salts and prodrugs derived therefrom.

Isoquinoline-3-carboxamides of Formula Ib include, but are not limited to, N-((1-chloro-4-hydroxy-7-(2-propyloxy) isoquinolin-3-yl)-carbonyl)-glycine, N-((1-chloro-4-hydroxy-6-(2-propyloxy)isoquinolin-3-yl)-carbonyl)-glycine, N-((1-chloro-4-hydroxy-isoquinoline-3-carbonyl)-amino)-acetic acid (Compound B), N-((1-chloro-4-hydroxy-7-methoxyisoquinolin-3-yl)-carbonyl)-glycine, N-((1-chloro-4-hydroxy-6-methoxyisoquinolin-3-yl)-carbonyl)-glycine, N-((7-butyloxy)-1-chloro-4-hydroxyisoquinolin-3-yl)-carbonyl)-glycine, N-((6-benzyloxy-1-chloro-4-hydroxy-isoquinoline-3-carbonyl)-amino)-acetic acid (Compound J), ((7-benzyloxy-1-chloro-4-hydroxy-isoquinoline-3-carbonyl)-amino)-acetic acid methyl ester (Compound K), N-((7-benzyloxy-1-chloro-4-hydroxy-isoquinoline-3-carbonyl)-amino)-acetic acid (Compound L), N-((8-chloro-4-hydroxyisoquinolin-3-yl)-carbonyl)-glycine, N-((7-butoxy-4-hydroxy-isoquinoline-3-carbonyl)-amino)-acetic acid (M), [(1,7-dichloro-4-hydroxy-isoquinoline-3-carbonyl)-amino]-acetic acid (Compound R), {[4-hydroxy-1-(naphthalen-2-yloxy)-isoquinoline-3-carbonyl]-amino}-acetic acid, {[4-hydroxy-1-(4-methoxy-phenoxy)-isoquinoline-3-carbonyl]-amino}-acetic acid, {[4-hydroxy-1-(3-methoxy-phenoxy)-isoquinoline-3-carbonyl]-amino}-acetic acid, {[1-(3-fluoro-phenoxy)-4-hydroxy-isoquinoline-3-carbonyl]-amino}-acetic acid, {[1-(4-fluoro-phenoxy)-4-hydroxy-isoquinoline-3-carbonyl]-amino}-acetic acid, {[1-(2-fluoro-phenoxy)-4-hydroxy-isoquinoline-3-carbonyl]-amino}-acetic acid, {[4-hydroxy-1-(2-methoxy-phenoxy)-isoquinoline-3-carbonyl]-amino}-acetic acid, [(4-hydroxy-1-phenylamino-isoquinoline-3-carbonyl)-amino]-acetic acid, [(1-chloro-4-methoxy-isoquinoline-3-carbonyl)-amino]-acetic acid, [(1-chloro-4-ethoxy-isoquinoline-3-carbonyl)-amino]-acetic acid, [(4-hydroxy-1-methoxy-isoquinoline-3-carbonyl)-amino]-acetic acid, [(1-ethoxy-4-hydroxy-isoquinoline-3-carbonyl)-amino]-acetic acid, [(4-hydroxy-1-phenyl-isoquinoline-3-carbonyl)-amino]-acetic acid, [(4-hydroxy-1-methyl-isoquinoline-3-carbonyl)-amino]-acetic acid, [(4-hydroxy-1-methoxymethyl-isoquinoline-3-carbonyl)-amino]-acetic acid, [(1-dimethylcarbamoyl-4-hydroxy-isoquinoline-3-carbonyl)-amino]-acetic acid, [(4-hydroxy-1-methyl-6-phenoxy-isoquinoline-3-carbonyl)-amino]-acetic acid, [(4-hydroxy-1-methyl-7-phenoxy-isoquinoline-3-carbonyl)-amino]-acetic acid (Compound U), [(4-benzyloxy-1-methyl-7-phenoxy-isoquinoline-3-carbonyl)-amino]-acetic acid, [(4-ethoxy-1-methyl-7-phenoxy-isoquinoline-3-carbonyl)-amino]-acetic acid, [(1-dimethylcarbamoyl-4-hydroxy-7-phenoxy-isoquinoline-3-carbonyl)-amino]-acetic acid, [(4-hydroxy-1-methoxymethyl-7-phenoxy-isoquinoline-3-carbonyl)-amino]-acetic acid, [(4-hydroxy-1-p-tolyl-isoquinoline-3-carbonyl)-amino]-acetic acid, {[7-(4-fluoro-phenoxy)-4-hydroxy-1-methyl-isoquinoline-3-carbonyl]-amino}-acetic acid, {[1-chloro-4-hydroxy-7-(4-methoxy-phenoxy)-isoquinoline-3-carbonyl]-amino}-acetic acid, {[4-hydroxy-7-(4-methoxy-phenoxy)-isoquinoline-3-carbonyl]-amino}-acetic acid (Compound T), {[1-chloro-4-hydroxy-6-(4-methoxy-phenoxy)-isoquinoline-3-carbonyl]-amino}-acetic acid, {[4-hydroxy-6-(4-methoxy-phenoxy)-isoquinoline-3-carbonyl]-amino}-acetic acid, {[1-chloro-4-hydroxy-7-(4-trifluoromethyl-phenoxy)-isoquinoline-3-carbonyl]-amino}-acetic acid, {[4-hydroxy-7-(4-trifluoromethyl-phenoxy)-isoquinoline-3-carbonyl]-amino}-acetic acid, {[1-chloro-4-hydroxy-6-(4-trifluoromethyl-phenoxy)-isoquinoline-3-carbonyl]-amino}-acetic acid, {[4-hydroxy-6-(4-trifluoromethyl-phenoxy)-isoquinoline-3-carbonyl]-amino}-acetic acid, {[1-chloro-7-(4-fluoro-phenoxy)-4-hydroxy-isoquinoline-3-carbonyl]-amino}-acetic acid, {[7-(4-fluoro-phenoxy)4-hydroxy-isoquinoline-3-carbonyl]-amino}-acetic acid, {[1-chloro-6-(4-fluoro-phenoxy)4-hydroxy-isoquinoline-3-carbonyl]-amino}-acetic acid, {[6-(4-fluoro-phenoxy)-4-hydroxy-isoquinoline-3-carbonyl]-amino}-acetic acid, [(7-benzenesulfinyl-4-hydroxy-isoquinoline-3-carbonyl)-amino]-acetic acid, [(7-benzenesulfonyl-4-hydroxy-isoquinoline-3-carbonyl)-amino]-acetic acid, [(6-benzenesulfinyl-4-hydroxy-isoquinoline-3-carbonyl)-amino]-acetic acid, [(6-benzenesulfonyl-4-hydroxy-isoquinoline-3-carbonyl)-amino]-acetic acid, {[4-hydroxy-7-(4-methoxy-benzenesulfonylamino)-isoquinoline-3-carbonyl]-amino}-acetic acid, [(4-hydroxy-1-phenylsulfanyl-isoquinoline-3-carbonyl)-amino]-acetic acid, {[1-(4-chloro-phenylsulfanyl)-4-hydroxy-isoquinoline-3-carbonyl]-amino}-acetic acid, [(4-1-p-tolylsulfanyl-isoquinoline-3-carbonyl)-amino]-acetic acid, {[4-hydroxy-1-(3-methoxy-phenylsulfanyl)-isoquinoline-3-carbonyl]-amino}-acetic acid, {[4-hydroxy-1-(2-methoxy-phenylsulfanyl)-isoquinoline-3-carbonyl]-amino}-acetic acid, {[4-hydroxy-1-(naphthalen-2-ylsulfanyl)-isoquinoline-3-carbonyl]-amino}-acetic acid, [(1-benzenesulfinyl-4-hydroxy-isoquinoline-3-carbonyl)-amino]-acetic acid, [(1-benzenesulfonyl-4-hydroxy-isoquinoline-3-carbonyl)-amino]-acetic acid, [(1-chloro-4-hydroxy-6,7-diphenoxy-isoquinoline-3-carbonyl)-amino]-acetic acid, [(4-hydroxy-6,7-diphenoxyisoquinoline-3-carbonyl)-amino]-acetic acid, {[4-hydroxy-7-(4-nitro-phenoxy)-isoquinoline-3-carbonyl]-amino}-acetic acid, [(4-mercapto-7-phenoxy-isoquinoline-3-carbonyl)-amino]-acetic acid, [(4-mercapto-7-trifluoromethyl-isoquinoline-3-carbonyl)-amino]-acetic acid, {[7-(4-chloro-phenoxy)-4-hydroxy-isoquinoline-3-carbonyl]-amino}-acetic acid, {[6-(4-chloro-phenoxy)-4-hydroxy-isoquinoline-3-carbonyl]-amino}-acetic acid, {[6-(3-fluoro-5-methoxy-phenoxy)-4-hydroxy-isoquinoline-3-carbonyl]-amino}-acetic acid, {[7-(3-fluoro-5-methoxy-phenoxy)4-hydroxy-isoquinoline-3-carbonyl]-amino}-acetic acid, {[7-(3,4-difluoro-phenoxy)4-hydroxy-isoquinoline-3-carbonyl]-amino}-acetic acid, {[6-(3,4-difluoro-phenoxy)-4-hydroxy-isoquinoline-3-carbonyl]-amino}-acetic acid, {[4-hydroxy-7-(4-trifluoromethoxy-phenoxy)-isoquinoline-3-carbonyl]-amino}-acetic acid, {[4-hydroxy-6-(4-trifluoromethoxy-phenoxy)-isoquinoline-3-carbonyl]-amino}-acetic acid, 2-(s)-{[7-(4-chloro-phenoxy)-4-hydroxy-isoquinoline-3-carbonyl]-amino}-propionic acid, 2-(s)-{[6-(4-chloro-phenoxy)4-hydroxy-isoquinoline-3-carbonyl]-amino}-propionic acid, 2-{[7-(3,4-difluoro-phenoxy)-4-hydroxy-isoquinoline-3-carbonyl]-amino}-propionic acid, 2-(s)-[(4-hydroxy-7-phenylsulfanyl-isoquinoline-3-carbonyl)-amino]-propionic acid., 2-(r)-[(4-hydroxy-7-phenylsulfanyl-isoquinoline-3-carbonyl)-amino]-propionic acid, 2-(r)-[(4-hydroxy-7-phenoxy-isoquinoline-3-carbonyl)-amino]-propionic acid, 2-(s)-{[4-hydroxy-7-(4-methoxy-phenoxy)-isoquinoline-3-carbonyl]-amino}-propionic acid, 2-(s)-[(7-benzenesulfonyl-4-hydroxy-isoquinoline-3-carbonyl)-amino]-propionic acid, (r)-2-[(4-hydroxy-1-methoxymethyl-7-phenoxy-isoquinoline-3-carbonyl)-amino]-propionic acid, (s)-2-[(4-hydroxy-1-methoxymethyl-7-phenoxy-isoquinoline-3-carbonyl)-amino]-propionic acid, (s)-2-[(4-mercapto-7-phenoxy-isoquinoline-3-carbonyl)-amino]-propionic acid, (s)-2-{[1-(4-chloro-phenylsulfanyl)-4-hydroxy-isoquinoline-3-carbonyl]-amino}-propionic acid, (r)-2-{[1-(4-chloro-phenylsulfanyl)-4-hydroxy-isoquinoline-3-carbonyl]-amino}-propionic acid, [(4-hydroxy-7-phenylsulfanyl-isoquinoline-3-carbonyl)-amino]-acetic acid, [(4-hydroxy-6-phenylsulfanyl-isoquinoline-3-carbonyl)-amino]-acetic acid, [(1-chloro-4-hydroxy-7-phenylsulfanyl-isoquinoline-3-carbonyl)-amino]-acetic acid, [(1-chloro-4-hydroxy-6-phenylsulfanyl-isoquinoline-3-carbonyl)-amino]-acetic acid, [(1-bromo-4-hydroxy-7-phenylsulfanyl-isoquinoline-3-carbonyl)-amino]-acetic acid, [(1-bromo-4-hydroxy-6-phenylsulfanyl-isoquinoline-3-carbonyl)-amino]-acetic acid, [(4-hydroxy-7-phenoxy-isoquinoline-3-carbonyl)-amino]-acetic acid (Compound S), [(4-hydroxy-6-phenoxy-isoquinoline-3-carbonyl)-amino]-acetic acid, [(1-chloro-4-hydroxy-7-phenoxy-isoquinoline-3-carbonyl)-amino]-acetic acid, [(1-chloro-4-hydroxy-6-phenoxy-isoquinoline-3-carbonyl)-amino]-acetic acid, [(1-bromo-4-hydroxy-7-phenoxy-isoquinoline-3-carbonyl)-amino]-acetic acid, [(1-bromo-4-hydroxy-6-phenoxy-isoquinoline-3-carbonyl)-amino]-acetic acid, {[7-(2,6-dimethyl-phenoxy)-4-hydroxy-isoquinoline-3-carbonyl]-amino}-acetic acid, {[1-chloro-7-(2,6-dimethyl-phenoxy)-4-hydroxy-isoquinoline-3-carbonyl]-amino}-acetic acid, {[1-bromo-7-(2,6-dimethyl-phenoxy)-4-hydroxy-isoquinoline-3-carbonyl]-amino}-acetic acid, [(1-bromo-7-chloro-4-hydroxy-isoquinoline-3-carbonyl)-amino]-acetic acid, [(1-bromo-6-chloro-4-hydroxy-isoquinoline-3-carbonyl)-amino]-acetic acid, [(1-bromo-4-hydroxy-7-trifluoromethyl-isoquinoline-3-carbonyl)-amino]-acetic acid, [(1-bromo-4-hydroxy-6-trifluoromethyl-isoquinoline-3-carbonyl)-amino]-acetic acid, [(4-hydroxy-1-phenoxy-isoquinoline-3-carbonyl)-amino]-acetic acid, [(1,7-dibromo-4-hydroxy-isoquinoline-3-carbonyl)-amino]-acetic acid, [(7-bromo-1-chloro-4-hydroxy-isoquinoline-3-carbonyl)-amino]-acetic acid, [(6-bromo-4-hydroxy-isoquinoline-3-carbonyl)-amino]-acetic acid, [(1-bromo-7-fluoro-4-hydroxy-isoquinoline-3-carbonyl)-amino]-acetic acid, [(7-fluoro-4-hydroxy-isoquinoline-3-carbonyl)-amino]-acetic acid, [(1-chloro-7-fluoro-4-hydroxy-isoquinoline-3-carbonyl)-amino]-acetic acid, [(1-bromo-4-hydroxy-isoquinoline-3-carbonyl)-amino]-acetic acid, [(4-hydroxy-6-phenyl-isoquinoline-3-carbonyl)-amino]-acetic acid, [(4-hydroxy-7-phenyl-isoquinoline-3-carbonyl)-amino]-acetic acid, [(1-chloro-4-hydroxy-6-phenyl-isoquinoline-3-carbonyl)-amino]-acetic acid, [(1-chloro-4-hydroxy-7-phenyl-isoquinoline-3-carbonyl)-amino]-acetic acid, [(1-bromo-4-hydroxy-6-phenyl-isoquinoline-3-carbonyl)-amino]-acetic acid, [(1-bromo-4-hydroxy-7-phenyl-isoquinoline-3-carbonyl)-amino]-acetic acid, [(4-hydroxy-5-phenyl-isoquinoline-3-carbonyl)-amino]-acetic acid, [(4-hydroxy-8-phenyl-isoquinoline-3-carbonyl)-amino]-acetic acid , [(1-chloro-4-hydroxy-5-phenyl-isoquinoline-3-carbonyl)-amino]-acetic acid, [(1-chloro-4-hydroxy-8-phenyl-isoquinoline-3-carbonyl)-amino]-acetic acid, [(1-bromo-4-hydroxy-5-phenyl-isoquinoline-3-carbonyl)-amino]-acetic acid, [(1-bromo-4-hydroxy-8-phenyl-isoquinoline-3-carbonyl)-amino]-acetic acid, [(1-ethylsulfanyl-4-hydroxy-isoquinoline-3-carbonyl)-amino]-acetic acid, {[4-hydroxy-1-(4-methoxy-phenylsulfanyl)-isoquinoline-3-carbonyl]-amino}-acetic acid, [(1-chloro-4-hydroxy-7-iodo-isoquinoline-3-carbonyl)-amino]-acetic acid, [(1-chloro-4-hydroxy-6-iodo-isoquinoline-3-carbonyl)-amino]-acetic acid, [(4-hydroxy-7-iodo-isoquinoline-3-carbonyl)-amino]-acetic acid, [(1-bromo-4-hydroxy-7-methyl-isoquinoline-3-carbonyl)-amino]-acetic acid, [(1-bromo-7-butoxy-4-hydroxy-isoquinoline-3-carbonyl)-amino]-acetic acid, [(1-bromo-6-butoxy-4-hydroxy-isoquinoline-3-carbonyl)-amino]-acetic acid, (r)-2-[(1-chloro-4-hydroxy-isoquinoline-3-carbonyl)-amino]-3-hydroxy-propionic acid, (s)-2-[(1-chloro-4-hydroxy-isoquinoline-3-carbonyl)-amino]-3-hydroxy-propionic acid, (r)-2-[(1-chloro-4-hydroxy-6-isopropoxy-isoquinoline-3-carbonyl)-amino]-3-hydroxy-propionic acid, (s)-2-[(1-chloro-4-hydroxy-6-isopropoxy-isoquinoline-3-carbonyl)-amino]-3-hydroxy-propionic acid, (r)-2-[(1-chloro-4-hydroxy-7-isopropoxy-isoquinoline-3-carbonyl)-amino]-3-hydroxy-propionic acid, (s)-2-[(1-chloro-4-hydroxy-7-isopropoxy-isoquinoline-3-carbonyl)-amino]-3-hydroxy-propionic acid, 2-[(1-chloro-4-hydroxy-isoquinoline-3-carbonyl)-amino]-2-methyl-propionic acid, 2-[(1-chloro-4-hydroxy-6-isopropoxy-isoquinoline-3-carbonyl)-amino]-2-methyl-propionic acid, (r)-2-[(1-chloro-4-hydroxy-isoquinoline-3-carbonyl)-amino]-3-(1h-imidazol-4-yl)-propionic acid (trifluoro-acetic acid salt), (s)-2-[(1-chloro-4-hydroxy-isoquinoline-3-carbonyl)-amino]-3-(1h-imidazol-4-yl)-propionic acid (trifluoro-acetic acid salt), (r)-2-[(1-chloro-4-hydroxy-isoquinoline-3-carbonyl)-amino]-3-methyl-butyric acid, (s)-2-[(1-chloro-4-hydroxy-isoquinoline-3-carbonyl)-amino]-3-methyl-butyric acid, (r)-2-[(1-chloro-4-hydroxy-6-isopropoxy-isoquinoline-3-carbonyl)-amino]-3-methyl-butyric acid, (s)-2-[(1-chloro-4-hydroxy-6-isopropoxy-isoquinoline-3-carbonyl)-amino]-3-methyl-butyric acid, (r)-2-[(1-chloro-4-hydroxy-7-isopropoxy-isoquinoline-3-carbonyl)-amino]-3-methyl-butyric acid, (s)-2-[(1-chloro-4-hydroxy-7-isopropoxy-isoquinoline-3-carbonyl)-amino]-3-methyl-butyric acid, (s)-2-[(6-benzyloxy-1-chloro-4-hydroxy-isoquinoline-3-carbonyl)-amino]-3-methyl-butyric acid, (r)-2-[(1-chloro-4-hydroxy-isoquinoline-3-carbonyl)-amino]-3-phenyl-propionic acid, (s)-2-[(1-chloro-4-hydroxy-isoquinoline-3-carbonyl)-amino]-3-phenyl-propionic acid, (r)-2-[(1-chloro- 4-hydroxy-6-isopropoxy-isoquinoline-3-carbonyl)-amino]-3-phenyl-propionic acid, (s)-2-[(1-chloro-4-hydroxy-6-isopropoxy-isoquinoline-3-carbonyl)-amino]-3-phenyl-propionic acid, (r)-2-[(1-chloro-4-hydroxy-7-isopropoxy-isoquinoline-3-carbonyl)-amino]-3-phenyl-propionic acid, (s)-2-[(1-chloro-4-hydroxy-7-isopropoxy-isoquinoline-3-carbonyl)-amino]-3-phenyl-propionic acid, (r)-2-[(1-chloro-4-hydroxy-isoquinoline-3-carbonyl)-amino]-3-(4-hydroxy-phenyl)-propionic acid, (s)-2-[(1-chloro-4-hydroxy-isoquinoline-3-carbonyl)-amino]-3-(4-hydroxy-phenyl)-propionic acid, (r)-2-[(1-chloro-4-hydroxy-6-isopropoxy-isoquinoline-3-carbonyl)-amino}-3-(4-hydroxy-phenyl)-propionic acid, (s)-2-[(1-chloro-4-hydroxy-6-isopropoxy-isoquinolie-3-carbonyl)-amino]-3-(4-hydroxy-phenyl)-propionic acid, (r)-2-[(1-chloro-4-hydroxy-7-isopropoxy-isoquinoline-3-carbonyl)-amino]-3-(4-hydroxy-phenyl)-propionic acid, (s)-2-[(1-chloro-4-hydroxy-7-isopropoxy-isoquinoline-3-carbonyl)-amino]-3-(4-hydroxy-phenyl)-propionic acid, (r)-2-[(1-chloro-4-hydroxy-6-isopropoxy-isoquinoline-3-carbonyl)-amino]-pentanoic acid, (s)-2-[(1-chloro-4-hydroxy-6-isopropoxy-isoquinoline-3-carbonyl)-amino]-pentanoic acid, (r)-1-(1-chloro-4-hydroxy-isoquinoline-3-carbonyl)-pyrrolidine-2-carboxylic acid, (s)-1-(1-chloro-4-hydroxy-isoquinoline-3-carbonyl)-pyrrolidine-2-carboxylic acid, (r)-1-(1-chloro-4-hydroxy-6-isopropoxy-isoquinoline-3-carbonyl)-pyrrolidine-2-carboxylic acid, (s)-1-(1-chloro-4-hydroxy-6-isopropoxy-isoquinoline-3-carbonyl)-pyrrolidine-2-carboxylic acid, (r)-6-amino-2-[(1-chloro-4-hydroxy-isoquinoline-3-carbonyl)-amino]-hexanoic acid (trifluoro-acetic acid salt), (s)-6-amino-2-[(1-chloro-4-hydroxy-isoquinoline-3-carbonyl)-amino]-hexanoic acid (trifluoro-acetic acid salt), (r)-6-amino-2-[(1-chloro-4-hydroxy-6-isopropoxy-isoquinoline-3-carbonyl)-amino]-hexanoic acid, trifluoroacetic acid salt, (s)-6-amino-2-[(1-chloro-4-hydroxy-6-isopropoxy-isoquinoline-3-carbonyl)-amino]-hexanoic acid (trifluoro-acetic acid salt), (r)-6-amino-2-[(1-chloro-4-hydroxy-7-isopropoxy-isoquinoline-3-carbonyl)-amino]-hexanoic acid, trifluoroacetic acid salt, (s)-6-amino-2-[(1-chloro-4-hydroxy-7-isopropoxy-isoquinoline-3-carbonyl)-amino]-hexanoic acid (trifluoro-acetic acid salt), (r)-2-[(1-chloro-4-hydroxy-isoquinoline-3-carbonyl)-amino]-succinic acid, (s)-2-[(1-chloro-4-hydroxy-isoquinoline-3-carbonyl)-amino]-succinic acid, (r)-2-[(1-chloro-4-hydroxy-6-isopropoxy-isoquinoline-3-carbonyl)-amino]-succinic acid, (s)-2-[(1-chloro-4-hydroxy-6-isopropoxy-isoquinoline-3-carbonyl)-amino]-succinic acid, (r)-2-[(1-chloro-4-hydroxy-7-isopropoxy-isoquinoline-3-carbonyl)-amino]-succinic acid, (r)-2-[(6-benzyloxy-1-chloro-4-hydroxy-isoquinoline-3-carbonyl)-amino]-propionic acid, (s)-2-[(7-benzyloxy-1-chloro-4-hydroxy-isoquinoline-3-carbonyl)-amino]-propionic acid, (r)-2-[(7-benzyloxy-1-chloro-4-hydroxy-isoquinoline-3-carbonyl)-amino]-propionic acid, (s)-2-[(1-chloro-4-hydroxy-isoquinoline-3-carbonyl)-amino]-propionic acid, (r)-2-[(1-chloro-4-hydroxy-isoquinoline-3-carbonyl)-amino]-propionic acid, (s)-2-[(6-isopropoxy-1-chloro-4-hydroxy-isoquinoline-3-carbonyl)-amino]-propionic acid, (r)-2-[6-isopropoxy-1-chloro-4-hydroxy-isoquinoline-3-carbonyl)-amino]-propionic acid, (s)-2-[(7-isopropoxy-1-chloro-4-hydroxy-isoquinoline-3-carbonyl)-amino-propionic acid, (r)-2-[(7-isopropoxy-1-chloro-4-hydroxy-isoquinoline-3 -carbonyl)-amino]propionic acid, {[7-(3,5-difluoro-phenoxy)-4-hydroxy-isoquinoline-3 -carbonyl]-amino}-acetic acid, {[6-(3,5-difluoro-phenoxy)-4-hydroxy-isoquinoline-3-carbonyl]-amino}-acetic acid, ({7-[4-(4-fluoro-phenoxy)-phenoxy]4-hydroxy-isoquinoline-3-carbonyl}-amino)-acetic acid, ({6-[4-(4-fluoro-phenoxy)-phenoxy]-4-hydroxy-isoquinoline-3-carbonyl}-amino)-acetic acid, {[7-(3-chloro-4-fluoro-phenoxy)-4-hydroxy-isoquinoline-3-carbonyl]-amino}-acetic acid, {[6-(3-chloro-4-fluoro-phenoxy)-4-hydroxy-isoquinoline-3-carbonyl]-amino}-acetic acid, (s)-2-{[7-(3-fluoro-5-methoxy-phenoxy)-4-hydroxy-isoquinoline-3-carbonyl]-amino}-propionic acid, 2-(s)-[(7-cyclohexyloxy-4-hydroxy-isoquinoline-3-carbonyl)-amino]-propionic acid, 2-(s)-{[7-(4-fluoro-phenoxy)-4-hydroxy-1-methyl-isoquinoline-3-carbonyl]-amino}-propionic acid, 2-(s)-{[7-(4-fluoro-phenoxy)-4-hydroxy-isoquinoline-3-carbonyl]-amino}-propionic acid, 2-(s)-[(4-hydroxy-1-methyl-7-phenoxy-isoquinoline-3-carbonyl)-amino]-propionic acid, 2-(s)-[(4-hydroxy-1-methyl-7-phenylsulfanyl-isoquinoline-3-carbonyl)-amino]-propionic acid, 2-(s)-{[4-hydroxy-7-(4-trifluoromethyl-phenoxy)-isoquinoline-3-carbonyl]-amino}-propionic acid, {[7-(4-chloro-phenoxy)-4-hydroxy-1-methyl-isoquinoline-3-carbonyl]-amino}-acetic acid, {[6-(4-chloro-phenoxy)-4-hydroxy-1-methyl-isoquinoline-3-carbonyl]-amino}-acetic acid, {[7-(3,5-difluoro-phenoxy)-4-hydroxy-1-methyl-isoquinoline-3-carbonyl]-amino}-acetic acid, {[4-hydroxy-7-(4-methoxy-phenoxy)-1-methyl-isoquinoline-3-carbonyl]-amino}-acetic acid, {[4-hydroxy-6-(4-methoxy-phenoxy)-1-methyl-isoquinoline-3-carbonyl]-amino}-acetic acid, [(6-cyclohexyloxy-4-hydr6xy-isoquinoline-3-carbonyl)-amino]-acetic acid, [(7-cyclohexyloxy-4-hydroxy-isoquinoline-3-carbonyl)-amino]-acetic acid, [(7-cyclohexyloxy-4-hydroxy-1-methyl-isoquinoline-3-carbonyl)-amino]-acetic acid, [(7-cyclohexylsulfanyl-4-hydroxy-isoquinoline-3-carbonyl)-amino]-acetic acid, [(7-cyclohexanesulfonyl-4-hydroxy-isoquinoline-3-carbonyl)-amino]-acetic acid, [(4-hydroxy-1-isobutyl-isoquinoline-3-carbonyl)-amino]-acetic acid, [(1-ethyl-4-hydroxy-7-phenoxy-isoquinoline-3-carbonyl)-amino]-acetic acid, [(1-dimethylaminomethyl-4-hydroxy-7-phenylsulfanyl-isoquinoline-3-carbonyl)-amino]-acetic acid, [(4-hydroxy-1-methyl-7-phenylsulfanyl-isoquinoline-3-carbonyl)-amino]-acetic acid, {[4-hydroxy-1-methyl-7-(4-trifluoromethyl-phenoxy)-isoquinoline-3-carbonyl]-amino}-acetic acid.

In other embodiments, compounds used in the methods of the invention are selected from a compound of the Formula II

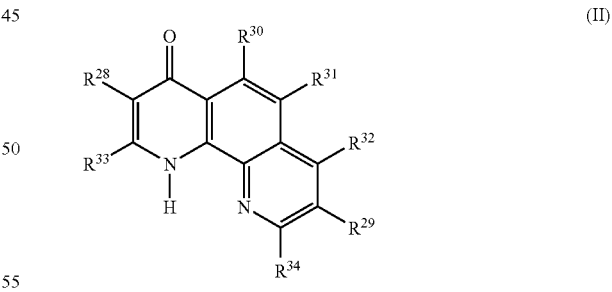

(II)

where $R^{28}$ is hydrogen, nitro, amino, cyano, halogen, $(C_1-C_4)$-alkyl, carboxy or a metabolically labile ester derivative thereof; $(C_1-C_4)$-alkylamino, di-$(C_1-C_4)$-alkylamino, $(C_1-C_6)$-alkoxycarbonyl, $(C_2-C_4)$-alkanoyl, hydroxy-$(C_1-C_4)$-alkyl, carbamoyl, N—$(C_1-C_4)$-alkylcarbamoyl, $(C_1-C_4)$-alkylthio, $(C_1-C_4)$-alkylsulfinyl, $(C_1-C_4)$-alkylsulfonyl, phenylthio, phenylsulfinyl, phenylsulfonyl, said phenyl or phenyl groups being optionally substituted with 1 to 4 identical or different halogen, $(C_1-C_4)$-alkyoxy, $(C_1-C_4)$-alkyl, cyano, hydroxy, trifluoromethyl, fluoro-($C_1$-$C_4$)-alkylthio, fluoro-($C_1$-$C_4$)-alkylsulfinyl, fluoro-($C_1$-$C_4$)-alkylsulfonyl, ($C_1$-$C_4$)-alkoxy-($C_2$-$C_4$)-alkoxycarbonyl, N,N-di-[($C_1$-$C_4$)-alkyl]carbamoyl-($C_1$-$C_4$)-alkoxycarbonyl, ($C_1$-$C_4$)-alkylamino-($C_2$-$C_4$)-alkoxycarbonyl, di-($C_1$-$C_4$)-alkylamino-($C_2$-$C_4$)-alkoxycarbonyl, ($C_1$-$C_4$)-alkoxy-($C_2$-$C_4$)-alkoxy-($C_2$-$C_4$)-alkoxycarbonyl, ($C_2$-$C_4$)-alkanoyloxy-$C_1$-$C_4$)-alkyl, or N-[amino-($C_2$-$C_8$)-alkyl]-carbamoyl;

$R^{29}$ is hydrogen, hydroxy, amino, cyano, halogen, ($C_1$-$C_4$)-alkyl, carboxy or metabolically labile ester derivative thereof, ($C_1$-$C_4$)-alkylamino, di-($C_1$-$C_4$)-alkylamino, ($C_1$-$C_6$)-alkoxycarbonyl, ($C_2$-$C_4$)-alkanoyl, ($C_1$-$C_4$)-alkoxy, carboxy-($C_1$-$C_4$)-alkoxy, ($C_1$-$C_4$)-alkoxycarbonyl-($C_1$-$C_4$)-alkoxy, carbamoyl, N—($C_1$-$C_8$)-alkylcarbamoyl, N,N-di-($C_1$-$C_8$)-alkylcarbamoyl, N-[amino-($C_2$-$C_8$)-alkyl]-carbamoyl, N-[($C_1$-$C_4$)-alkylamino-($C_1$-$C_8$)-alkyl]-carbamoyl, N-[di-($C_1$-$C_4$)-alkylamino-($C_1$-$C_8$)-alkyl]]-carbamoyl, N-cyclohexylcarbamoyl, N-[cyclopentyl]-carbamoyl, N—($C_1$-$C_4$)-alkylcyclohexylcarbamoyl, N—($C_1$-$C_4$)-alkylcyclopentylcarbamoyl, N-phenylcarbamoyl, N—($C_1$-$C_4$)-alkyl-N-phenylcarbamoyl, N,N-diphenylcarbamoyl, N-[phenyl-($C_1$-$C_4$)-alkyl]-carbamoyl, N—($C_1$-$C_4$)-alkyl-N-[phenyl-($C_1$-$C_4$)-alkyl]-carbamoyl, or N,N-di-[phenyl-($C_1$-$C_4$)-alkyl]-carbamoyl, said phenyl or phenyl groups being optionally substituted with 1 to 4 identical or different halogen, ($C_1$-$C_4$)-alkyoxy, ($C_1$-$C_4$)-alkyl, cyano, hydroxy, trifluoromethyl, N-[($C_2$-$C_4$)-alkanoyl]-carbamoyl, N-[($C_1$-$C_4$)-alkoxycarbonyl]-carbamoyl, N-[fluoro-($C_2$-$C_6$)-alkyl]-carbamoyl, N,N-[fluoro-($C_2$-$C_6$)-alkyl]-N—($C_1$-$C_4$)-alkylcarbamoyl, N,N-[difluoro-($C_2$-$C_6$)-alkyl]carbamoyl, pyrrolidin-1-ylcarbonyl, piperidinocarbonyl, piperazin-1-ylcarbonyl, morpholinocarbonyl, wherein the heterocyclic group, is optionally substituted with 1 to 4, ($C_1$-$C_4$)-alkyl, benzyl, 1,2,3,4-tetrahydro-isoquinolin-2-ylcarbonyl, N,N-[di-($C_1$-$C_4$)-alkyl]-thiocarbamoyl, N—($C_2$-$C_4$)-alkanoylamino, or N-[($C_1$-$C_4$)-alkoxycarbonyl]-amino;

$R^{30}$ is hydrogen, ($C_1$-$C_4$)-alkyl, ($C_2$-$C_4$)-alkoxy, halo, nitro, hydroxy, fluoro-(1-4C)alkyl, or pyridinyl;

$R^{31}$ is hydrogen, ($C_1$-$C_4$)-alkyl, ($C_2$-$C_4$)-alkoxy, halo, nitro, hydroxy, fluoro-($C_1$-$C_4$)-alkyl, pyridinyl, or methoxy;

$R^{32}$ is hydrogen, hydroxy, amino, ($C_1$-$C_4$)-alkylamino, di-($C_1$-$C_4$)-alkylamino, halo, ($C_1$-$C_4$)-alkoxy-($C_2$-$C_4$)-alkoxy, fluoro-($C_1$-$C_6$)-alkoxy, pyrrolidin-1-yl, piperidino, piperazin-1-yl, or morpholino, wherein the heterocyclic group is optionally substituted with 1 to 4 identical or different ($C_1$-$C_4$)-alkyl or benzyl; and $R^{33}$ and $R^{34}$ are individually selected from hydrogen, ($C_1$-$C_4$)-alkyl, and ($C_1$-$C_4$)-alkoxy;

including pharmaceutically-acceptable salts and pro-drugs derived therefrom.

Exemplary compounds of Formula II are described in U.S. Pat. Nos. 5,916,898 and 6,200,974, and International Publication No. WO 99/21860. All compounds listed in the foregoing patents and publication, in particular, those listed in the compound claims and the final products of the working examples, are hereby incorporated into the present application by reference herein. Exemplary compounds of Formula (II) include 4-oxo-1,4-dihydro-[1,10]phenanthroline-3-carboxylic acid (Compound A) (see, e.g., Seki et al. (1974) Chem Abstracts 81:424, No. 21), 3-carboxy-5-hydroxy-4-oxo-3,4-dihydro-1,10-phenanthroline, 3-carboxy-5-methoxy-4-oxo-3,4-dihydro-1,10-phenanthroline, 5-methoxy-4-oxo-1,4-dihydro-[1,10]phenanthroline-3-carboxylic acid ethyl ester, 5-methoxy-4-oxo-1,4-dihydro-[1,10]phenanthroline-3-carboxylic acid (Compound Q), and 3-carboxy-8-hydroxy-4-oxo-3,4-dihydro-1,10-phenanthroline.

In other embodiments, compounds used in the methods of the invention are selected from a compound of the Formula III

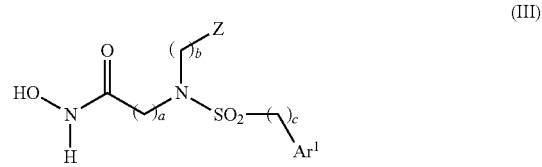

(III)

or pharmaceutically acceptable salts thereof, wherein:

a is an integer from 1 to 4;

b is an integer from 0 to 4;

c is an integer from 0 to 4;

Z is selected from the group consisting of ($C_3$-$C_{10}$) cycloalkyl, ($C_3$-$C_{10}$) cycloalkyl independently substituted with one or more $Y^1$, 3-10 membered heterocycloalkyl and 3-10 membered heterocycloalkyl independently substituted with one or more $Y^1$; ($C_5$-$C_{20}$) aryl, ($C_5$-$C_{20}$) aryl independently substituted with one or more $Y^1$, 5-20 membered heteroaryl and 5-20 membered heteroaryl independently substituted with one or more $Y^1$;

$Ar^1$ is selected from the group consisting of ($C_5$-$C_{20}$) aryl, ($C_5$-$C_{20}$) aryl independently substituted with one or more $Y^2$, 5-20 membered heteroaryl and 5-20 membered heteroaryl independently substituted with one or more $Y^2$;

each $Y^1$ is independently selected from the group consisting of a lipophilic functional group, ($C_5$-$C_{20}$) aryl, ($C_6$-$C_{26}$) alkaryl, 5-20 membered heteroaryl and 6-26 membered alk-heteroaryl;

each $Y^2$ is independently selected from the group consisting of -R', —OR', —OR", —SR', —SR", —NR'R', —$NO_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —$SO_2$R', —$SO_2$R", —NR'—$SO_2$—R', —NR'—C(O)—NR'R', tetrazol-5-yl, —NR'—C(O)—OR', —C(NR'R')=NR', —S(O)—R', —S(O)—R", and —NR'—C(S)—NR'R'; and each R' is independently selected from the group consisting of —H, ($C_1$-$C_8$) alkyl, ($C_2$-$C_8$) alkenyl, and ($C_2$-$C_8$) alkynyl; and each R" is independently selected from the group consisting of ($C_5$-$C_{20}$) aryl and ($C_5$-$C_{20}$) aryl independently substituted with one or more —OR', —SR', —NR'R', —$NO_2$, —CN, halogen or trihalomethyl groups, or wherein c is 0 and $Ar^1$ is an N' substituted urea-aryl, the compound has the structural Formula IIIa:

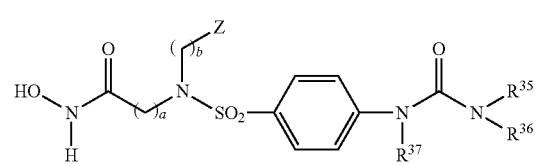

(IIIa)

or pharmaceutically acceptable salts thereof, wherein:

a, b, and Z are as defined above; and $R^{35}$ and $R^{36}$ are each independently selected from the group consisting of hydrogen, $(C_1-C_8)$ alkyl, $(C_2-C_8)$ alkenyl, $(C_2-C_8)$ alkynyl, $(C_3-C_{10})$ cycloalkyl, $(C_5-C_{20})$ aryl, $(C_5-C_{20})$ substituted aryl, $(C_6-C_{26})$ alkaryl, $(C_6-C_{26})$ substituted alkaryl, 5-20 membered heteroaryl, 5-20 membered substituted heteroaryl, 6-26 membered alk-heteroaryl, and 6-26 membered substituted alk-heteroaryl; and $R^{37}$ is independently selected from the group consisting of hydrogen, $(C_1-C_8)$ alkyl, $(C_2-C_8)$ alkenyl, and $(C_2-C_8)$ alkynyl.

Exemplary compounds of Formula (III) are described in International Publication No. WO 00/50390. All compounds listed in WO 00/50390, in particular, those listed in the compound claims and the final products of the working examples, are hereby incorporated into the present application by reference herein. Exemplary compounds of Formula (III) include 3-{[4-(3,3-dibenzyl-ureido)-benzenesulfonyl]-[2-(4-methoxy-phenyl)-ethyl]-amino}-N-hydroxy-propionamide (Compound C), 3-{{4-[3-(4-chloro-phenyl)-ureido]-benzenesulfonyl}-[2-(4-methoxy-phenyl)-ethyl]-amino}-N-hydroxy-propionamide, and 3-{{4-[3-(1,2-diphenyl-ethyl)-ureido]-benzenesulfonyl}-[2-(4-methoxy-phenyl)-ethyl]-amino}-N-hydroxy-propionamide.

In certain embodiments, compounds used in the methods of the invention are selected from a compound of the formula (IV)

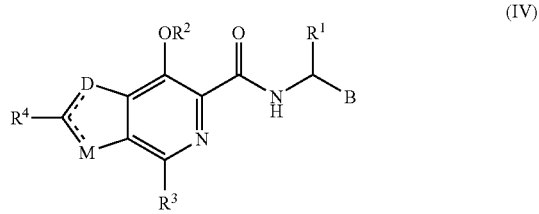

(IV)

wherein $R^1$ are selected from the group consisting of hydrogen, $(C_1-C_6)$-alkyl, $(C_3-C_7)$-cycloalkyl, aryl, or a substituent of the α-carbon atom of an α-amino acid, wherein the amino acid is a natural L-amino acid or its D-isomer;

B is —$CO_2H$ or a $CO_2$-G carboxyl radical, where G is a radical of an alcohol G-OH in which G is selected from the group consisting of $(C_1-C_{20})$-alkyl radical, $(C_3-C_8)$ cycloalkyl radical, $(C_2-C_{20})$-alkenyl radical, $(C_3-C_8)$-cycloalkenyl radical, retinyl radical, $(C_2-C_{20})$-alkynyl radical, $(C_4-C_{20})$-alkenynyl radical;

$R^2$ is selected from the group consisting of hydrogen, $(C_1-C_{10})$-alkyl, $(C_2-C_{10})$-alkenyl, $(C_2-C_{10})$-alkynyl, wherein alkenyl or alkynyl contains one or two C—C multiple bonds;

unsubstituted fluoroalkyl radical of the formula —$[CH_2]_x$—$C_fH_{(2f+1-g)}$—$F_g$, aryl, heteroaryl, and $(C_7-C_{11})$-aralkyl;

one of D or M is —S—, and the other is =C($R^5$)—;

$R^3$, $R^4$, and $R^5$ are identical or different and are selected from the group consisting of hydrogen, hydroxyl, halogen, cyano, trifluoromethyl, nitro, carboxyl; $(C_1-C_{20})$-alkyl, $(C_3-C_8)$-cycloalkyl, $(C_3-C_8)$-cycloalkoxy, $(C_6-C_{12})$-aryl, $(C_7-C_{16})$-aralkyl, $(C_7-C_{16})$-aralkenyl, $(C_7-C_{16})$-aralkynyl, $(C_2-C_{20})$-alkenyl, $(C_2-C_{20})$-alkynyl, $(C_1-C_{20})$-alkoxy, $(C_2-C_{20})$-alkenyloxy, $(C_2-C_{20})$-alkynyloxy, retinyloxy, $(C_6-C_{12})$-aryloxy, $(C_7-C_{16})$-aralkyloxy, $(C_1-C_{16})$-hydroxyalkyl, —O—$[CH_2]_xC_fH_{(2f+1-g)}F_g$, —$OCF_2Cl$, —$OCF_2$—$CHFCl$, $(C_1-C_{20})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_2-C_{20})$-alkenylcarbonyl, $(C_2-C_{20})$-alkynylcarbonyl, $(C_1-C_{20})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{20})$-alkenyloxycarbonyl, retinyloxycarbonyl, $(C_2-C_{20})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy, $(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy, carbamoyl, N—$(C_1-C_{12})$-alkylcarbamoyl, N,N-di-$(C_1-C_{12})$-alkylcarbamoyl, N—$(C_3-C_8)$-cycloalkylcarbamoyl, N,N-dicyclo-$(C_3-C_8)$-alkylcarbamoyl, N—$(C_1-C_{10})$-alkyl-N—$(C_3-C_8)$-cycloalkylcarbamoyl, N-(($C_3-C_8$)-cycloalkyl-($C_1-C_6$)-alkyl)-carbamoyl, N-(+)-dehydroabietylcarbamoyl, N—$(C_1-C_6)$-alkyl-N-(+)-dehydroabietylcarbamoyl, N—$(C_6-C_{12})$-arylcarbamoyl, N—$(C_7-C_{16})$-aralkylcarbamoyl, N—$(C_1-C_{10})$-alkyl-N—$(C_6-C_{16})$-arylcarbamoyl, N—$(C_1-C_{10})$-alkyl-N—$(C_7-C_{16})$-aralkylcarbamoyl, carbamoyloxy, N—$(C_1-C_{12})$-alkylcarbamoyloxy, N,N-di-$(C_1-C_{12})$-alkylcarbamoyloxy, N—$(C_3-C_8)$-cycloalkylcarbamoyloxy, N—$(C_6-C_{12})$-arylcarbamoyloxy, N—$(C_7-C_{16})$-aralkylcarbamoyloxy, N—$(C_1-C_{10})$-alkyl-N—$(C_6-C_{12})$-arylcarbamoyloxy, N—$(C_1-C_{10})$-alkyl-N—$(C_7-C_{16})$-aralkylcarbamoyloxy, N—(($C_1-C_{10}$)-alkyl)-carbamoyloxy, N—$(C_1-C_{10})$-alkyl-N—(($C_7-C_{16}$)-aralkyloxy-($C_1-C_{10}$)-alkyl)-carbamoyloxyamino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N—$(C_6-C_{12})$-arylamino, N—$(C_7-C_{11})$-aralkylamino, N-alkyl-aralkylamino, N-alkyl-arylamino, $(C_1-C_{12})$-alkoxyamino, $(C_1-C_{12})$-alkoxy-N—$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_6)$-aralkanoylamino, $(C_1-C_{12})$-alkanoyl-N—$(C_1-C_{10})$-alkylamino, $(C_3-C_8)$-cycloalkanoyl-N—$(C_1-C_{10})$-alkylamino, $(C_6-C_{12})$-aroyl-N—$(C_1-C_{10})$-alkylamino, $(C_7-C_{11})$-aralkanoyl-N—$(C_1-C_{10})$-alkylamino, amino-$(C_1-C_{10})$-alkyl, $(C_1-C_{20})$-alkylmercapto, $(C_1-C_{20})$-alkylsulfinyl, $(C_1-C_{20})$-alkylsulfonyl, $(C_6-C_{12})$-arylmercapto, $(C_6-C_{12})$-arylsulfinyl, $(C_6-C_{12})$-arylsulfonyl, $(C_7-C_{16})$-aralkylmercapto, $(C_7-C_{16})$-aralkylsulfinyl, $(C_7-C_{16})$-aralkylsulfonyl, sulfamoyl, N—$(C_1-C_{10})$-alkylsulfamoyl, N,N-di-$(C_1-C_{10})$-alkylsulfamoyl, $(C_3-C_8)$-cycloalkylsulfamoyl, N—$(C_6-C_{12})$-arylsulfamoyl, N—$(C_7-C_{16})$-aralkylsulfamoyl, N—$(C_1-C_{10})$-alkyl-N—$(C_6-C_{12})$-arylsulfamoyl, N—$(C_1-C_{10})$-alkyl-N—$(C_7-C_{16})$-aralkylsulfamoyl, $(C_1-C_{10})$-alkylsulfonamido, $(C_7-C_{16})$-aralkylsulfonamido, and N-(($C_1-C_{10}$)-alkyl-($C_7-C_{16}$)-aralkylsulfonamido; where an aryl radical may be substituted by 1 to 5 substituents selected from hydroxyl, halogen, cyano, trifluoromethyl, nitro, carboxyl, $(C_2-C_{16})$-alkyl, $(C_3-C_8)$-cycloalkyl, $(C_3-C_8)$-cycloalkoxy, $(C_6-C_{12})$-aryl, $(C_7-C_{16})$-aralkyl, $(C_2-C_{16})$-alkenyl, $(C_2-C_{12})$-alkynyl, $(C_1-C_{16})$-alkoxy, $(C_1-C_{16})$-alkenyloxy, $(C_6-C_{12})$-aryloxy, $(C_7-C_{16})$-aralkyloxy, $(C_1-C_8)$-hydroxyalkyl, —O—$[CH_2]_xC_fH_{(2f+1-g)}F_g$, —$OCF_2Cl$, and —$OCF_2$—$CHFCl$;

x is 0 to 3;
f is 1 to 8; and
g is 0 or 1 to (2f+1);
including the physiologically active salts and prodrugs derived therefrom.

Compounds of Formula (IV) include, but are not limited to, [(2-bromo-4-hydroxy-thieno[2,3-c]pyridine-5-carbonyl)-amino]-acetic acid, [(2-bromo-7-hydroxy-thieno[3,2-c]pyridine-6-carbonyl)-amino]-acetic acid, {[4-hydroxy-2-(4-methoxy-phenyl)-thieno[2,3-c]pyridine-S-carbonyl]-amino}-acetic acid, {[7-hydroxy-2-(4-methoxy-phenyl)-thieno[3,2-c]pyridine-6-carbonyl]-amino}-acetic acid, [(4-hydroxy-2,7-dimethyl-thieno[2,3-c]pyridine-5-carbonyl)-amino]-acetic acid, [(7-hydroxy-2,4-dimethyl-thieno[3,2-c]pyridine-6-carbonyl)-amino]-acetic acid, {[7-hydroxy-4-methyl-2-(4-phenoxy-phenyl)-thieno[3,2-c]pyridine-6-carbonyl]-amino}-acetic acid, {[4-hydroxy-2-(4-phenoxy-phenyl)-7-methyl-thieno[2,3-c]pyridine-5-carbonyl]-amino}-acetic acid, {[4-hydroxy-2-(4-phenoxy-phenyl)-thieno[2,3-c]pyridine-5-carbonyl]-amino}-acetic acid, {[7-hydroxy-2-(4-phenoxy-phenyl)-thieno[3,2-c]pyridine-6-carbonyl]-amino}-acetic acid, [(2,7-dibromo-4-hydroxy-thieno[2,3-c]pyridine-5-carbonyl)-amino]-acetic acid, [(2-bromo-7-chloro-4-hydroxy-thieno[2,3-c]pyridine-5-carbonyl)-amino]-acetic acid, [(7-hydroxy-thieno[3,2-c]pyridine-6-carbonyl)-amino]-acetic acid, [(4-hydroxy-thieno[2,3-c]pyridine-5-carbonyl)-amino]-acetic acid, [(2-bromo-4-chloro-7-hydroxy-thieno[3,2-c]pyridine-6-carbonyl)-amino]-acetic acid, [(2,4-dibromo-7-hydroxy-thieno[3,2-c]pyridine-6-carbonyl)-amino]-acetic acid, [(7-hydroxy-2-phenylsulfanyl-thieno[3,2-c]pyridine-6-carbonyl)-amino]-acetic acid, [(4-hydroxy-2-phenylsulfanyl-thieno[2,3-c]pyridine-5-carbonyl)-amino]-acetic acid, [(4-hydroxy-2,7-diphenyl-thieno[2,3-c]pyridine-5-carbonyl)-amino]-acetic acid, [(7-hydroxy-2,4-diphenyl-thieno[3,2-c]pyridine-6-carbonyl)-amino]-acetic acid, [(7-hydroxy-2-styryl-thieno[3,2-c]pyridine-6-carbonyl)-amino]-acetic acid, [(7-hydroxy-2-phenoxy-thieno[3,2-c]pyridine-6-carbonyl)-amino]-acetic acid, [(7-hydroxy-2-phenethyl-thieno[3,2-c]pyridine-6-carbonyl)-amino]-acetic acid, [7-hydroxy-2-(3-trifluoromethyl-phenyl)-thieno[3,2-c]pyridine-6-carbonyl]-amino}-acetic acid, {[4-bromo-7-hydroxy-2-(3-trifluoromethyl-phenyl)-thieno[3,2-c]pyridine-6-carbonyl]-amino}-acetic acid, {[4-cyano-7-hydroxy-2-(3-trifluoromethyl-phenyl)-thieno[3,2-c]pyridine-6-carbonyl]-amino}-acetic acid, [(2-cyano-7-hydroxy-thieno[3,2-c]pyridine-6-carbonyl)-amino]-acetic acid, {[7-hydroxy-2-(4-trifluoromethyl-phenyl)-thieno[3,2-c]pyridine-6-carbonyl]-amino}-acetic acid, {[7-hydroxy-2-(2-trifluoromethyl-phenyl)-thieno[3,2-c]pyridine-6-carbonyl]-amino}-acetic acid, {[4-bromo-3-(4-fluoro-phenyl)-7-hydroxy-thieno[3,2-c]pyridine-6-carbonyl]-amino}-acetic acid, {[3-(4-fluoro-phenyl)-7-hydroxy-thieno[3,2-c]pyridine-6-carbonyl]-amino}-acetic acid, {[3-(4-fluoro-phenyl)-7-hydroxy-4-methyl-thieno[3,2-c]pyridine-6-carbonyl]-amino}-acetic acid, {[4-cyano-3-(4-fluoro-phenyl)-7-hydroxy-thieno[3,2-c]pyridine-6-carbonyl]-amino}-acetic acid, {[2-(4-fluoro-phenyl)-7-hydroxy-thieno[3,2-c]pyridine-6-carbonyl]-amino}-acetic acid, {[2-(4-fluoro-phenyl)-7-hydroxy-4-methyl-thieno[3,2-c]pyridine-6-carbonyl]-amino}-acetic acid, {[2,3-bis-(4-fluoro-phenyl)-7-hydroxy-thieno[3,2-c]pyridine-6-carbonyl]-amino}-acetic acid, {[7-bromo-3-(4-fluoro-phenyl)-4-hydroxy-thieno[2,3-c]pyridine-5-carbonyl]-amino}-acetic acid, {[3-(4-fluoro-phenyl)-4-hydroxy-thieno[2,3-c]pyridine-5-carbonyl]-amino}-acetic acid, {[2-(4-fluoro-phenyl)-4-hydroxy-thieno[2,3-c]pyridine-5-carbonyl]-amino}-acetic acid, {[2-(4-fluoro-phenyl)-4-hydroxy-7-methyl-thieno[2,3-c]pyridine-5-carbonyl]-amino}-acetic acid, [(7-chloro-4-hydroxy-thieno[2,3-c]pyridine-5-carbonyl)-amino]-acetic acid, [(4-chloro-7-hydroxy-thieno[3,2-c]pyridine-6-carbonyl)-amino]-acetic acid, [(7-bromo-4-hydroxy-thieno[2,3-c]pyridine-5-carbonyl)-amino]-acetic acid, [(4-bromo-7-hydroxy-thieno[3,2-c]pyridine-6-carbonyl)-amino]-acetic acid, [(4-hydroxy-7-phenyl-thieno[2,3-c]pyridine-5-carbonyl)-amino]-acetic acid, [(7-hydroxy-4-phenyl-thieno[3,2-c]pyridine-6-carbonyl)-amino]-acetic acid, {[7-(4-fluoro-phenyl)-4-hydroxy-thieno[2,3-c]pyridine-5-carbonyl]-amino}-acetic acid, {[4-(4-fluoro-phenyl)-7-hydroxy-thieno[3,2-c]pyridine-6-carbonyl]-amino}-acetic acid, 2-(7-(furan-2-yl)-4-hydroxythieno[2,3-c]pyridine-5-carboxamido)acetic acid, [(4-furan-2-yl-7-hydroxy-thieno[3,2-c]pyridine-6-carbonyl)-amino]-acetic acid, [(7-furan-3-yl-4-hydroxy-thieno[2,3-c]pyridine-5-carbonyl)-amino]-acetic acid, [(4-furan-3-yl-7-hydroxy-thieno[3,2-c]pyridine-6-carbonyl)-amino]-acetic acid, 2-(4-hydroxy-7-(thiophen-2-yl)thieno[2,3-c]pyridine-5-carboxamido)acetic acid, [(7-hydroxy-4-thiophen-2-yl-thieno[3,2-c]pyridine-6-carbonyl)-amino]-acetic acid, [(4-hydroxy-7-thiophen-3-yl-thieno[2,3-c]pyridine-5-carbonyl)-amino]-acetic acid, [(7-hydroxy-4-thiophen-3-yl-thieno[3,2-c]pyridine-6-carbonyl)-amino]-acetic acid, [(4-hydroxy-7-methyl-thieno[2,3-c]pyridine-5-carbonyl)-amino]-acetic acid, [(7-hydroxy-4-methyl-thieno[3,2-c]pyridine-6-carbonyl)-amino]-acetic acid, [(7-ethynyl-4-hydroxy-thieno[2,3-c]pyridine-5-carbonyl)-amino]-acetic acid, [(4-ethynyl-7-hydroxy-thieno[3,2-c]pyridine-6-carbonyl)-amino]-acetic acid, [(7-cyano-4-hydroxy-thieno[2,3-c]pyridine-5-carbonyl)-amino]-acetic acid, and [(4-cyano-7-hydroxy-thieno[3,2-c]pyridine-6-carbonyl)-amino]-acetic acid.

Exemplary compounds for use in the present methods include 4-oxo-1,4-dihydro-[1,10]phenanthroline-3-carboxylic acid, N-((1-chloro-4-hydroxy-isoquinoline-3-carbonyl)-amino)-acetic acid, 3-{[4-(3,3-dibenzyl-ureido)-benzenesulfonyl]-[2-(4-methoxy-phenyl)-ethyl]-amino}-N-hydroxy-propionamide, 7-(4-methyl-piperazin-1-ylmethyl)-5-phenylsulfanylmethyl-quinolin-8-ol, 4-nitro-quinolin-8-ol, 5-butoxymethyl-quinolin-8-ol, [(3-hydroxy-pyridine-2-carbonyl)-amino]-acetic acid, N-((3-hydroxy-6-isopropoxy-quinoline-2-carbonyl)-amino)-acetic acid, [(3-hydroxy-6-trifluoromethoxy-quinoline-2-carbonyl)-amino]-acetic acid, N-((6-benzyloxy-1-chloro-4-hydroxy-isoquinoline-3-carbonyl)-amino)-acetic acid, ((7-benzyloxy-1-chloro-4-hydroxy-isoquinoline-3-carbonyl)-amino)-acetic acid methyl ester, N-((7-benzyloxy-1-chloro-4-hydroxy-isoquinoline-3-carbonyl)-amino)-acetic acid, N-((7-butoxy-4-hydroxy-isoquinoline-3-carbonyl)-amino)-acetic acid, 6-cyclohexyl-1-hydroxy-4-methyl-1H-pyridin-2-one, [(6-chloro-3-hydroxy-quinoline-2-carbonyl)-amino]-acetic acid, [(3-methoxy-pyridine-2-carbonyl)-amino]-acetic acid, 5-methoxy-4-oxo-1,4-dihydro-[1,1]phenanthroline-3-carboxylic acid, [(1,7-dichloro-4-hydroxy-isoquinoline-3-carbonyl)-amino]-acetic acid, [(4-hydroxy-7-phenoxy-isoquinoline-3-carbonyl)-amino]-acetic acid, {[4-hydroxy-7-(4-methoxy-phenoxy)-isoquinoline-3-carbonyl]-amino}-acetic acid, and [(4-hydroxy-1-methyl-7-phenoxy-isoquinoline-3-carbonyl)-amino]-acetic acid.

In a particular embodiment, a compound for use in the present methods is selected from the group consisting of N-((1-chloro-4-hydroxy-isoquinoline-3-carbonyl)-amino)-acetic acid, [(1,7-dichloro-4-hydroxy-isoquinoline-3-carbonyl)-amino]-acetic acid, [(4-hydroxy-7-phenoxy-isoquinoline-3-carbonyl)-amino]-acetic acid, {[4-hydroxy-7-(4- methoxy-phenoxy)-isoquinoline-3-carbonyl]-amino}-acetic acid, [(4-hydroxy-1-methyl-7-phenoxy-isoquinoline-3-carbonyl)-amino]-acetic acid Pharmaceutical Formulations and Routes of Administration An effective dose or amount of an agent of the present invention refers to an amount or dose of the agent that results in amelioration of symptoms, for example, or an improvement in kidney function, or a prolongation of survival in a subject. An improvement in kidney function can be measured by an alteration in any measurable parameter of kidney function, including any of the parameters described herein. An effective amount can readily be determined by routine experimentation using a variety of techniques well-known in the art. The effective amount or therapeutically effective amount is the amount of the agent or pharmaceutical composition that will elicit the desired biological or medical response that is being sought by the researcher, veterinarian, medical doctor, or other clinician.

The compositions of the present invention can be delivered directly or in pharmaceutical compositions containing carriers, excipients, buffers, etc., as is well known in the art. Pharmaceutically acceptable excipients are available in the art, and include those listed in various pharmacopoeias. (See, e.g., USP, JP, EP, and BP, FDA web page (www.fda.gov), Inactive Ingredient Guide 1996, and Handbook of Pharmaceutical Additives, ed. Ash; Synapse Information Resources, Inc. 2002.) Various formulations and drug delivery systems are available in the art. (See, e.g., Gennaro, ed. (2000) Remington's Pharmaceutical Sciences, supra; and Hardman, Limbird, and Gilman, eds. (2001) The Pharmacological Basis of Therapeutics.)

The compositions of the present invention can be delivered directly or in pharmaceutical compositions along with suitable carriers or excipients, as is well known in the art. Present methods of treatment can comprise administration of an effective amount of a compound of the invention to a subject. In a preferred embodiment, the subject is a mammalian subject, and in a most preferred embodiment, the subject is a human subject. Preferred routes of administration include oral and transdermal delivery mechanisms.

An effective amount of such agents can readily be determined by routine experimentation, as can the most effective and convenient route of administration and the most appropriate formulation. Various formulations and drug delivery systems are available and selection of an appropriate formulation is within the level of skill in the art. (See, e.g., Gennaro, ed. (1995) *Remington's Pharmaceutical Sciences*, supra; and Hardman, Limbird, and Gilman, eds. (2001) *The Pharmacological Basis of Therapeutics*, supra.)

Suitable routes of administration may, for example, include oral, rectal, transmucosal, nasal, or intestinal administration and parenteral delivery, including intramuscular, subcutaneous, intramedullary injections, as well as intrathecal, direct intraventricular, intravenous, intraperitoneal, intranasal, or intraocular injections. The agent or composition thereof may be administered in a local rather than a systemic manner. For example, a suitable agent can be delivered via injection or in a targeted drug delivery system, such as a depot or sustained release formulation.

The pharmaceutical compositions of the present invention may be manufactured by any of the methods well-known in the art, such as by conventional mixing, dissolving, granulating, dragee-making, levigating, emulsifying, encapsulating, entrapping, or lyophilizing processes. As noted above, the compositions of the present invention can include one or more physiologically acceptable carriers such as excipients and auxiliaries that facilitate processing of active molecules into preparations for pharmaceutical use.

Proper formulation is dependent upon the route of administration chosen. For injection, for example, the composition may be formulated in aqueous solutions, preferably in physiologically compatible buffers such as Hanks's solution, Ringer's solution, or physiological saline buffer. For transmucosal or nasal administration, penetrants appropriate to the barrier to be permeated are used in the formulation. Such penetrants are generally known in the art. For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject. The compounds may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In one embodiment, the compounds of the present invention can be administered transdermally, such as through a skin patch, or topically. In one aspect, the transdermal or topical formulations of the present invention can additionally comprise one or multiple penetration enhancers or other effectors, including agents that enhance migration of the delivered compound. Transdermal or topical administration could be preferred, for example, in situations in which location specific delivery is desired.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges of, for example, gelatin, for use in an inhaler or insufflator may be formulated. These typically contain a powder mix of the compound and a suitable powder base such as lactose or starch.

Compositions formulated for parenteral administration by injection, e.g., by bolus injection or continuous infusion, can be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Formulations for parenteral administration include aqueous solutions or other compositions in water-soluble form.

Suspensions of the active compounds may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use.

As mentioned above, the compositions of the present invention may also be formulated as a depot preparation. Such long acting formulations may be administered by implantation (for example, subcutaneously or intramuscular) or by intramuscular injection. Thus, for example, the present compounds may be formulated with suitable polymeric or hydrophobic materials (for example as an emulsion in an acceptable oil) or ion exchange resins, or as sparingly soluble derivatives, for example, as a sparingly soluble salt.

Suitable carriers for the hydrophobic molecules of the invention are well-known in the art and include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system is effective in dissolving hydrophobic compounds and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g.,polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Liposomal delivery systems are discussed above in the context of gene-delivery systems. Certain organic solvents such as dimethylsulfoxide also may be employed, although usually at the cost of greater toxicity. Additionally, the compounds may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the compounds for a few weeks up to over 100 days. Depending on the chemical nature and the biological stability of the therapeutic reagent, additional strategies for protein stabilization may be employed.

For any composition used in the present methods of treatment, a therapeutically effective dose can be estimated initially using a variety of techniques well known in the art. For example, based on information obtained from a cell culture assay, a dose can be formulated in animal models to achieve a circulating concentration range that includes the $IC_{50}$. Similarly, dosage ranges appropriate for human subjects can be determined, for example, using data obtained from cell culture assays and other animal studies.

A therapeutically effective dose of an agent refers to that amount of the agent that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}, ED_{50}$. Agents that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

Dosage amount and interval may be adjusted individually to provide plasma levels of the active moiety that are sufficient to modulate HIFα stabilization and HIF-regulated gene induction, as desired, i.e., minimal effective concentration (MEC). The MEC will vary for each compound but can be estimated from, for example, in vitro data. Dosages necessary to achieve the MEC will depend on individual characteristics of the compound and the route of administration. Agents or compositions thereof should be administered using a regimen which maintains plasma levels above the MEC for about 10-90% of the duration of treatment, preferably about 30-90% of the duration of treatment, and most preferably between 50-90%. In cases of local administration or selective uptake, the effective local concentration of the drug may not be related to plasma concentration.

The amount of agent or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

Methods of Using the Compounds of the Invention

In one aspect, a compound of the invention inhibits one or more 2-oxoglutarate dioxygenase enzymes. In one embodiment, the compound inhibits at least two 2-oxoglutarate dioxygenase family members, e.g., HIF prolyl hydroxylase and HIF asparagine-hydroxylase (FIH-1), with either the same specificity or with differential specificity. In another embodiment, the compound is specific for one 2-oxoglutarate dioxygenase, e.g., HIF prolyl hydroxylase, and shows little to no specificity for other family members.

The compounds can be administered in combination with various other therapeutic approaches. In one embodiment, the compound is administered with another 2-oxoglutarate dioxygenase inhibitor, wherein the two compounds have differential specificity for individual 2-oxoglutarate dioxygenase family members. The two compounds may be administered at the same time as a ratio of one relative to the other. Determination of a ratio appropriate to a given course of treatment or a particular subject is within the level of skill in the art. Alternatively, the two compounds may be administered consecutively during a treatment time course. In a particular embodiment, one compound specifically inhibits HIF prolyl hydroxylase enzyme activity, and a second compound specifically inhibits procollagen prolyl 4-hydroxylase enzyme activity. In another specific embodiment, one compound specifically inhibits HIF prolyl hydroxylase enzyme activity, and a second compound specifically inhibits HIF asparaginyl-hydroxylase enzyme activity. In another embodiment, the compound is administered with another therapeutic agent having a different mode of action, e.g., an ACE inhibitor (ACEI), angiotensin-II receptor blocker (ARB), statin, diuretic, digoxin, carnitine, etc.

Compound Screening and Identification

Various assays and screening techniques, including those described below, can be used to identify small molecules that modulate (e.g., increase or decrease) the level or activity of HIFα. Assays will typically provide for detectable signals associated with the consumption of a reaction substrate or production of a reaction product. Detection can involve, for example, fluorophores, radioactive isotopes, enzyme conjugates, and other detectable labels well known in the art. The results may be qualitative or quantitative. Isolation of the reaction product may be facilitated by a label, such as biotin or a histidine tag that allows purification from other reaction components via precipitation or affinity chromatography.

Assays for HIFα hydroxylation may involve measuring hydroxylated proline or lysine residues in HIFα or a fragment thereof (see, e.g., Palmerini et al. (1985) J Chromatogr 339: 285-292), or measuring formation of succinate from 2-oxoglutarate in the presence of enzyme and HIFα or a fragment thereof (see, e.g., Cunliffe et al. (1986) Biochem J 240:617-619). Exemplary procedures that measure HIFα hydroxylation are described in Ivan et al. (supra) and Example 8. An exemplary procedure that measures production of succinate from 2-oxoglutarate is described by Kaule and Gunzler. (1990; Anal Biochem 184:291-297.) Substrate molecules may include HIFα or a fragment thereof, e.g., HIF(556-575); for example, an exemplary substrate for use in the assay described in Example 8 is [methoxycoumarin]-DLDLEAL-APYIPADDDFQL-amide. Enzyme may include, e.g., HIFα prolyl hydroxylase (see, e.g., GenBank Accession No. AAG33965, etc.), obtained from any source. Enzyme may also be present in a crude cell lysate or in a partially purified form. Compounds that stabilize HIFα or that inhibit hydroxylation of HIFα may be identified by measuring and comparing enzyme activity in the absence and presence of the compound.

Additionally and in combination with the above methods, compounds can be identified by any of a variety of screening techniques known in the art. Such screening methods may allow for target polypeptides or the compounds to be free in solution, affixed to a solid support, borne on a cell surface, or located within a cell. For example, test compounds may be arrayed on a surface and analyzed for activity in a manner analogous to array methods currently available in the art. (See, e.g., Shalon et al. (1995) International Publication No. WO 95/35505; Baldeschweiler et al. (1995) International Publication No. WO 95/251116; Brennan et al. (1995) U.S. Pat. No. 5,474,796; and Heller et al. (1997) U.S. Pat. No. 5,605,662.)These and other embodiments of the present invention will readily occur to those of ordinary skill in the art in view of the disclosure herein, and are specifically contemplated.

EXAMPLES

The invention is understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Example 1

Increased GFR and Decreased Serum Creatinine Levels in Human Subjects

Patients with chronic kidney disease (CKD), and with anemia associated with CKD, not yet receiving dialysis and not receiving recombinant EPO therapy, were randomized to either a treatment group or a placebo group. The treatment group was administered compound B (6 mg/kg) orally three times a week (Monday, Wednesday, and Friday) for four weeks (i.e., day 0 to day 28). Compound B has been previously shown to both stabilize HIFα and to inhibit HIF hydroxylase activity. Both groups were observed for an additional two weeks (i.e., to day 42). Glomerular filtration rate was estimated as standard in the art from serum creatinine measurements using the Cockcroft-Gault formula. (See Cockcroft and Gault (1976) Nephron 16:31-41.)

Figure 1B:
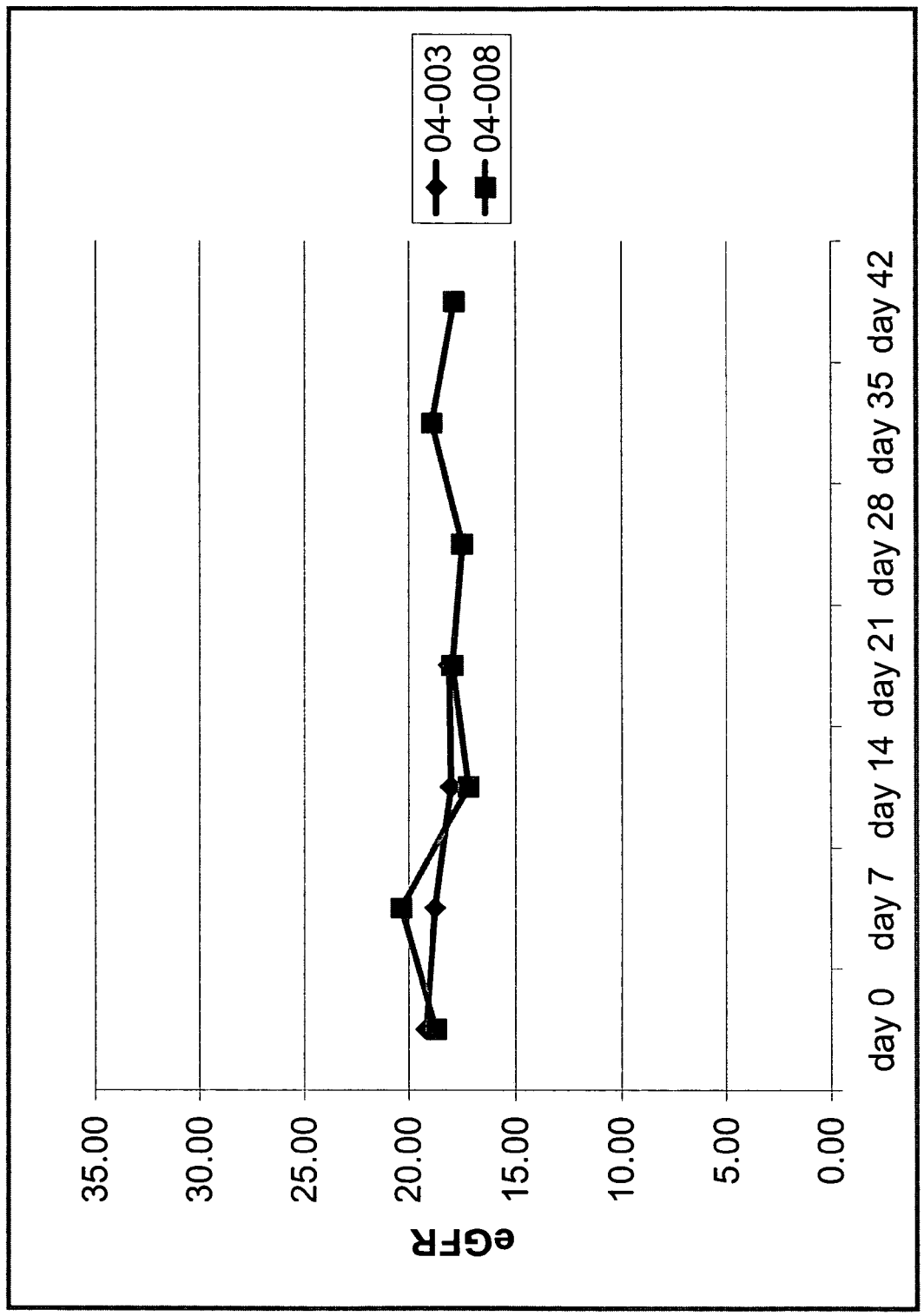

Mean estimated GFR for all patients on day 0 was 20.0 ml/min/1.73 m2 (range=12.4 to 31.7 ml/min/1.73 m$^2$), indicating severe renal impairment and reduced renal function associated with chronic kidney disease. As shown in FIG. 1A, administration of a compound of the present invention increased eGFR in patients (e.g., patient 04-004 and patient 04-009). No change in eGFR was observed in the placebo group (FIG. 1B, patient 04-003 and patient 04-008). Table 1 below shows serum creatinine levels (µmol/l) in patients treated with compound B or with placebo. The values for serum creatinine levels (µmol/l) shown in Table 1 can be expressed as mg/dl. For example, a serum creatinine level of 231 mmol/l (patient 04-004, day 42) can be expressed as 2.625 mg/dl. As shown in Table 1 below, patients treated with compound B (e.g., patient 04-004 and patient 04-009) showed decreased serum creatinine levels.

TABLE 1

|  | Day 0 | Day 7 | Day 14 | Day 21 | Day 28 | Day 35 | Day 42 |
|---|---|---|---|---|---|---|---|
| Patient 04-001 | 647 | 637 | 706 | 761 | 711 | 703 | 716 |
| Patient 04-002 | 316 | 373 | 295 | 314 | 331 | 340 | 411 |
| Patient 04-003 (placebo) | 404 | 413 | 430 | 428 |  |  |  |
| Patient 04-004 | 376 | 305 | 284 | 257 | 275 |  | 231 |
| Patient 04-008 (placebo) | 397 | 365 | 432 | 414 | 425 | 393 | 416 |
| Patient 0-009 | 424 | 432 | 360 | 489 | 455 |  | 365 |
| Patient 04-106 | 417 | 570 | 449 | 441 | 425 |  |  |

These results demonstrated that methods and compounds of the present invention increased GFR, and decreased serum creatinine, in patients having severe renal impairment and chronic kidney disease. Therefore, the present methods and compounds are effective in improving kidney function in human subjects.

Example 2

Improved Renal Function in a Rat Model of Impaired Kidney Function

To examine the effects of compounds and methods of the present invention on kidney function, the following studies were performed. For these studies, male Sprague-Dawley rats (Winkelmann, Borchen, Germany) were used at weights of 180-230 grams. Animals were fed a standard diet and had free access to water. In these studies, animals were administered (by intraperitoneal injection) a dose of 25 mg/kg compound R, dissolved in 100 μl DMSO and 900 μl NaCl (0.9%), 6 hours prior to initiation of the ischemic insult, as described below. In some experiments, animals were exposed to 0.1% carbon monoxide (CO) as previously described. (See Rosenberger et al (2002) J Am Soc Nephrol 13:1721-1732.)

Kidney dysfunction (impaired kidney function) was induced by renal ischemia-reperfusion injury (IRI) as follows. Animals were anaesthetized with ketamine (100 mg/kg) and pentobarbital sodium (50 mg/kg, Nembutal®, Abbott, Wiesbaden, Germany). A constant body temperature of 37° C. was maintained using a heated table with temperature feedback by a rectal probe (Heating Conroller Type 861, Hugo Sachs Elektronik-Harvard Apparatus GmbH, March, Germany). A blood sample of 300 μl was taken via tail vein puncture (time point 0 hr). The abdomen was shaved and a midline incision was made. After removal of the right kidney, the left renal artery was clamped with an arterial clamp (B-2, S&T, Neuhausen, Switzerland) to induce ischemia in the kidney, which was verified by the change of the renal color. After an ischemic period of 40 minutes, the arterial clamp was removed and reperfusion of the kidney was initiated. The abdomen was closed and animals were kept on the heating table until awakening after anaesthesia. Twenty-four hours later, the animals were briefly anaesthetized with isoflourane (Forene®, Abbott, Wiesbaden, Germany) and a second blood sample (24 hr) of 300 μl was drawn. After 72 hr the animals were anaesthetised and a third blood sample (72 hr) was drawn.

For these experiments, animals were divided into five treatment groups (n=10 for each group) as follows: Group A (Sham), sham operated animals without impaired kidney function; Group B (CO), animals treated with 0.1% carbon monoxide prior to induction of impaired kidney function; Group C (UnT), untreated animals with IRI; Group D (Compound R), animals treated with compound R 6 hours prior to induction of impaired kidney function; and Group E (Veh), vehicle-treated animals injected with 100 μl DMSO+900 μl NaCl (0.9%) 6 hours prior to induction of impaired kidney function.

Serum Urea

As shown in Table 2 below, both untreated control animals (UnT) and vehicle-treated control animals (Veh) had increased serum urea levels 24 hours and 72 hours following the induction of impaired renal function compared to that seen in sham control animals. This data indicated that renal injury resulted in reduced kidney function, as evidenced by increased serum urea levels. Animals exposed to 0.1% CO for 10 hours or treated with compound B 6 hours prior to induction of impaired renal function had reduced levels of serum urea compared to untreated (UnT) or vehicle-treated (Veh) control animals. Specifically, 24 hours and 72 hours after induction of impaired renal function, serum urea levels were significantly lower in animals administered compound B compared to untreated control animals. (See Table 2; data represents mean serum urea levels+/− standard deviation; #=p<0.05 vs. sham; *=p<0.05 vs. UnT or Veh; n=10.) This data indicated that administration of compound B improved renal function compared to untreated and vehicle-treated control animals.

TABLE 2

|  | Serum urea [mg/dl] 0 hr | Serum urea [mg/dl] 24 hr | Serum urea [mg/dl] 72 hr |
|---|---|---|---|
| Sham (Group A) | 37 +/− 7 | 46 +/− 6 | 46 +/− 5 |
| UnT (Group B) | 39 +/− 10 | 257 +/− 40 # | 202 +/− 70 # |
| CO (Group C) | 52 +/− 8 | 158 ( 78 # * | 120 ( 78 # * |
| Veh (Group D) | 35 +/− 10 | 319 +/− 135 # | 265 +/− 113 # |
| Cmpd R (Group E) | 41 +/− 10 | 179 +/− 61 # * | 91 +/− 36 # * |

Serum Creatinine

Figure 2:
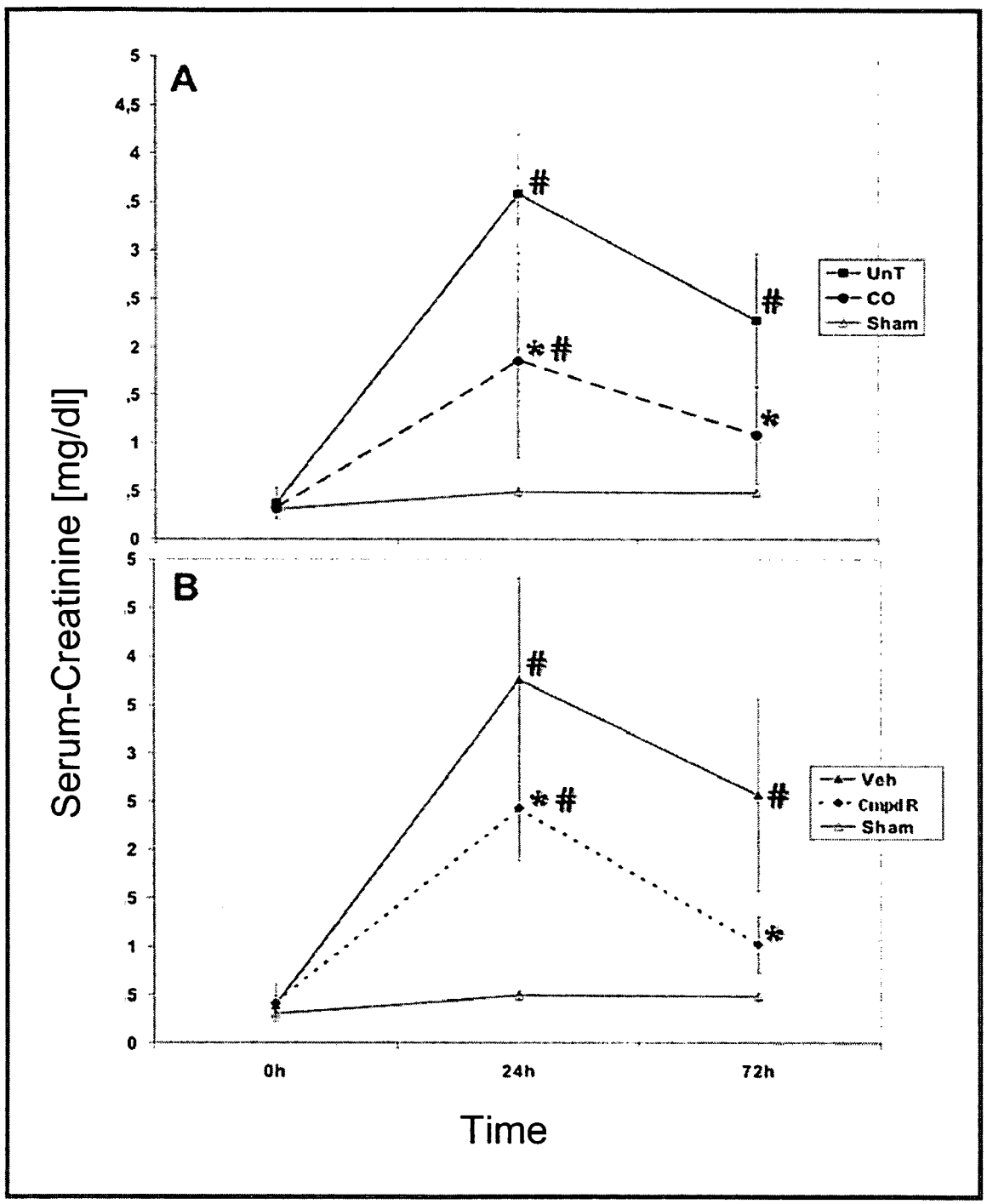
FIGS. 2A and 2B set forth data showing the methods and compounds of the present invention decreased serum creatinine levels in an animal model of impaired renal or kidney function.

As shown in FIGS. 2A and 2B, both untreated control animals (UnT) and vehicle-treated control animals (Veh) had increased serum creatinine levels 24 hours and 72 hours following the renal ischemic injury compared to that seen in sham control animals. This data indicated that induction of impaired renal function resulted in reduced kidney function, as evidenced by increased serum creatinine levels. Animals exposed to 0.1% CO for 10 hours prior to induction of impaired renal function or treated with compound R 6 hours prior to induction of impaired renal function had reduced levels of serum creatinine compared to untreated (UnT) or vehicle-treated (Veh) control animals. Specifically, 24 hours and 72 hours after onset of kidney dysfunction, serum creatinine levels were significantly lower in animals administered compound R compared to untreated control animals. (See FIGS. 2A and 2B; data represents mean serum creatinine levels+/− standard deviation; #=p<0.05 vs. sham; *=p<0.05 vs. UnT or Veh; n=10.) This data showed that administration of compound R improved renal function compared to untreated and vehicle-treated control animals. These results indicated that methods and compounds of the present invention were effective at improving kidney function.

Example 3

Improved Renal Function in a Rat Model of Impaired Kidney Function

To examine the effects of compounds and methods of the present invention on kidney function, the following studies were performed. For these studies, Sprague Dawley rats (Charles River Labs) were used. Animals were housed in an animal facility according to IACUC protocols with free access to water and food, and all experiments conducted according to the National Institutes of Health guidelines for animal experimentation.

Renal ischemia-reperfusion injury (IRI) and renal dysfunction were induced in male Sprague-Dawley rats (280-300 g) as previously described. (See Nemoto et al (2001) Kidney Int 59:246-251.) Briefly, rats were anesthetized under isoflurane and a midline abdominal incision was made under sterile conditions followed by bluntly dissecting the renal pedicles. A vascular clip was placed on the right renal pedicle while the left kidney underwent simultaneous nephrectomy. After 45 minutes of occlusion (ischemia), the clip was released and reperfusion was observed by changing color of the kidney. Animal body temperature was maintained constant, and warm 0.9% saline (0.5% of body weight) was administered directly into abdomen before the incision was completely sutured. Six hours before ischemia-reperfusion injury was performed, rats were administered either equal volumes of 0.5% CMC or 135 mg/kg compound S in suspension by oral gavage in a volume of 6 ml/kg.

Blood was collected on days 3, 7 and 10 after IRI for measurement of blood urea nitrogen (BUN) and serum creatinine levels. After warming under a heating lamp, rats were anesthetized with isoflurane and blood collected from the tail vein. For serum analysis, ~0.7 ml of blood was transferred to a Microtainer Serum Separator tube followed by incubation at room temperature for ~30 minutes, with centrifugation at 10,000 rpm in a Eppendorf 5415C Micro Centrifuge (Hayward, Calif.) for 10 min at 4° C.

BUN and serum creatinine concentrations were measured using an automated analyzer (Roche/Hitachi 911). BUN concentration was determined by an enzymatic procedure according to the method of Talke and Shubert. (See Talke and Schubert (1965) Klin Wochenschr 43:174-175.) Serum creatinine concentration was determined by the Jaffe reaction as modified by Bartels. (See Bartels and Bohmer (1973) Med Lab (Stuttg.) 26:209-215.) For BUN measurements, the inter-assay coefficient of variance (CV) and the intra-assay CV were determined to be <3.6% and <2.1%, respectively. For serum creatinine measurements, the inter-assay CV and the intra-assay CV were determined to be <2.1% and <1.7%, respectively.

Figure 3:
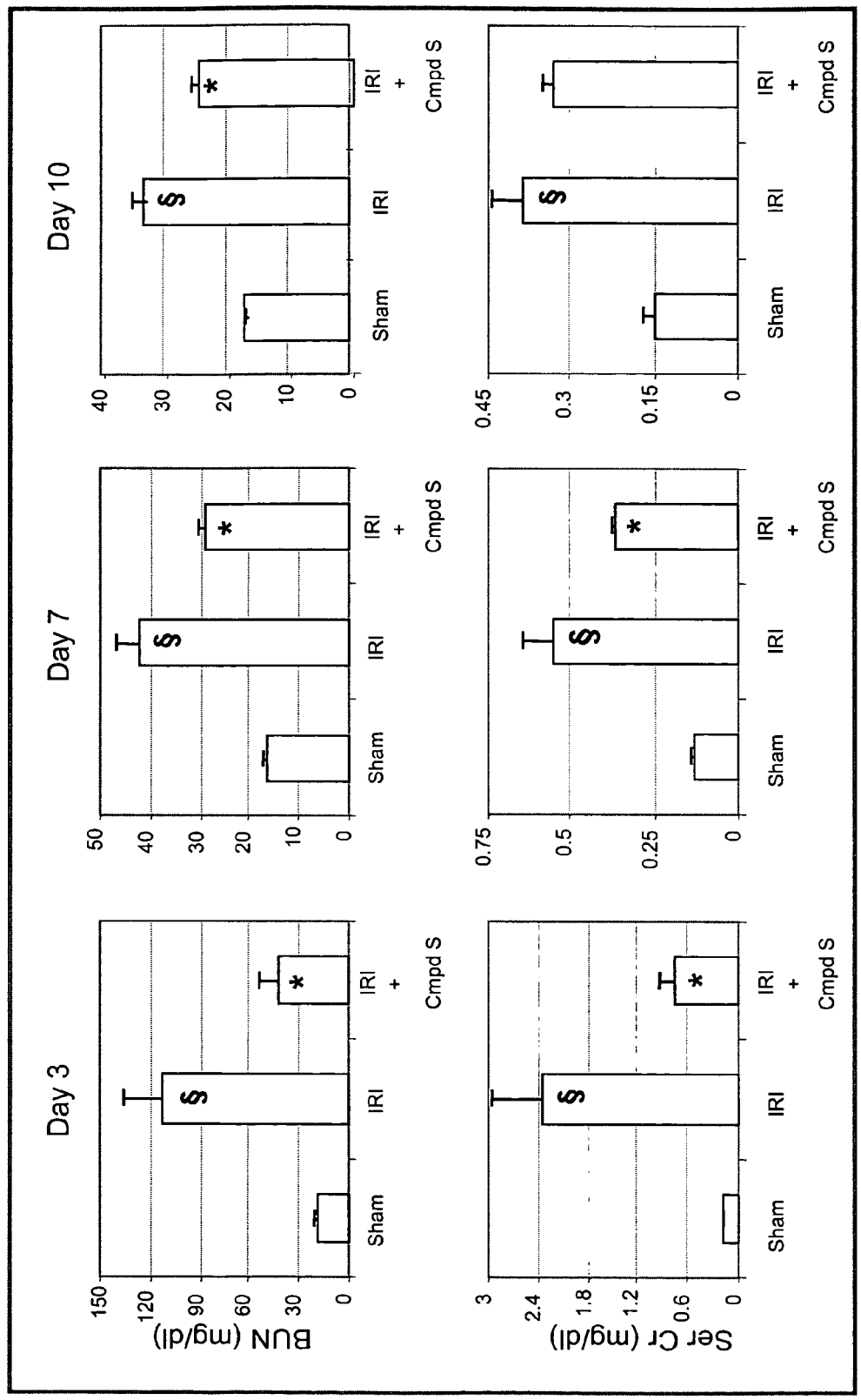
FIG. 3 sets forth data showing the methods and compounds of the present invention decreased BUN levels and serum creatinine levels in an animal model of impaired renal function.

As shown in FIG. 3, animals administered vehicle control prior to renal IRI had statistically significant increases in BUN and serum creatinine levels on day 3 compared to sham operated animals without IRI (BUN, sham vs IRI, $p<0.05$; serum creatinine, sham vs. IR, $p<0.05$). Elevated levels of both BUN and serum creatinine peaked at day 3 following induction of impaired renal function and gradually diminished over time, but remained above that of sham control animals at day 7 and day 10 post-IRI. In contrast to animals administered vehicle and undergoing IRI, animals administered compound S 6 hours prior to induction of renal dysfunction showed a statistically significant reduction in peak BUN and serum creatinine levels at day 3, a significant reduction in BUN at day 7 and day 10, and significant reduction in serum creatinine levels at day 7 ($p<0.05$ for each comparison). Specifically, these results showed that a single dose of compound S administered six hours prior to induction of impaired renal function improved kidney function as evidenced by sustained reductions in both serum creatinine levels (day 3 post MRI, 2.37±0.59 mg/dl vs. IRI+Cmpd S, 0.73±0.21 mg/dl, $p<0.004$) and blood urea nitrogen (BUN) (day 3 post IRI, 112.8±23 mg/dl vs. IRI+Cmpd S, 43±12 mg/dl, $p<0.004$). These results showed that compound S administered to animals 6 hours prior to induction of impaired renal function was effective at improving kidney function. These results indicated that methods and compounds of the present invention were effective at improving kidney function.

Example 4

Improved Kidney Function in a Mouse Model of Impaired Kidney Function

To examine the effects of compounds and methods of the present invention on kidney function, the following studies were performed. In this study, the effects of oral administration of compound T on renal function in a mouse model of renal IRI were examined. Male C57BL/6 mice (Charles River Laboratories, Hollister, Calif.) of approximately 22-25 grams were used in these studies.

Renal ischemia-reperfusion injury (IRI) and renal dysfunction were induced in mice using techniques previously described. (See Patel et al (2004) Kidney Int 66(3):983-989 and Lee et al (2004) J Am Soc Nephrol 15:102-111.) Briefly, mice were anesthetized by intraperitoneal (i.p.) injection of chloral hydrate at 300-400 mg/kg (8-10 mL/kg of 4%) or to effect. Kidneys were exposed through an abdominal section, and the right kidney was removed after its vascular pedicle and ureter were ligated. The vascular pedicle of the left kidney was clamped by a micro-aneurysm clip for 40 minutes after right nephrectomy. After the renal clamp was removed, the kidney was observed for reflow (reperfusion) after which 0.6 mL saline at 37° C. was injected into the abdomen and the incision was sutured. Mice were kept on a heating blanket and allowed to recover from anesthesia. All experimental techniques were in accordance to National Institutes of Health guidelines for animal experimentation.

For these studies, animals were divided into 5 treatment groups as follows. Group A, oral vehicle administered at 10 mL/kg without induction of impaired renal function; Group B, oral vehicle administered at 10 mL/kg 6 hours prior to induction of impaired renal function; Group C, oral administration of compound T (15 mg/kg) 6 hours prior to induction of impaired renal function; Group D, oral administration of compound T (30 mg/kg) 6 hours prior to induction of impaired renal function; and Group E, oral administration of compound T (60 mg/kg) 6 hours prior to induction of impaired renal function. All treatment groups administered compound T were treated with a single oral administration of compound T 6 hours prior to induction of renal dysfunction.

Twenty-four hours after induction of impaired renal function, blood was collected from the animals from the abdominal vein (animals under isoflurane anesthesia) into a heparinized tube for plasma preparation. The plasma tubes were centrifuged for 10 min at 4° C. and the plasma was transferred to a 1.5 ml tube. The plasma was transferred on wet ice to Quality Clinical Labs, Inc. (Mountain View, Calif.) for analysis of BUN levels and serum creatinine levels.

Figure 4:
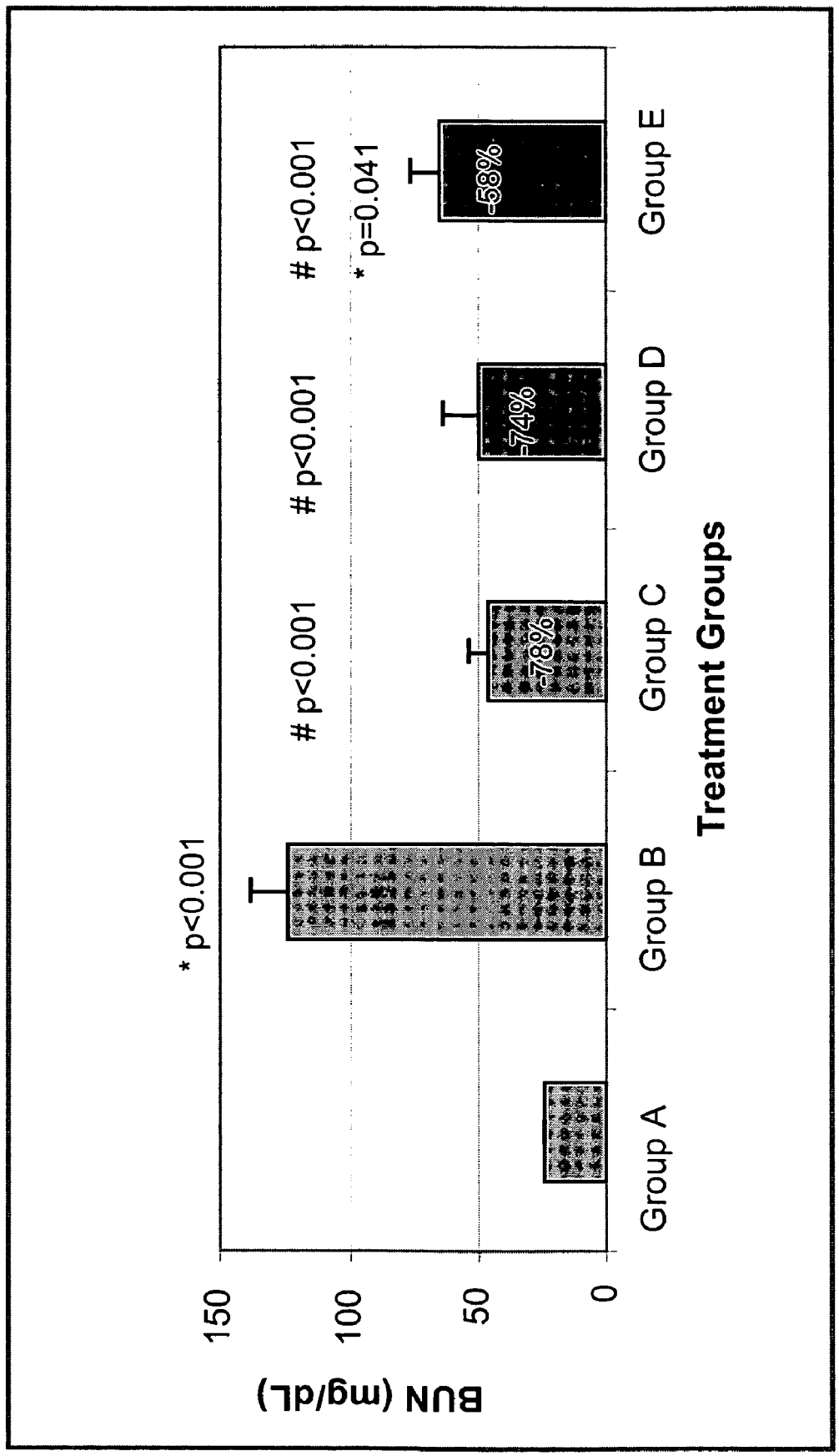
FIG. 4 sets forth data showing the methods and compounds of the present invention decreased BUN levels in an animal model of impaired renal function.

As shown in FIG. 4, animals administered vehicle control prior to induction of impaired renal function (Group B) had elevated BUN levels one day after induction of impaired renal function compared to that of sham control animals (Group A).

Animals administered compound T prior to induction of impaired renal function showed significantly reduced BUN levels compared to vehicle-treated animals with renal dysfunction. Specifically, administration of various concentrations of compound T (Group C, 15 mg/kg; Group D, 30 mg/kg; or Group E, 60 mg/kg) improved renal function as demonstrated by reducing the elevated BUN levels 24 hours after induction of impaired renal function. (Values in FIG. 4 are presented as mean values for BUN levels±SEM.) (* significantly higher than Group A; # significantly lower than Group B.)

Figure 5:
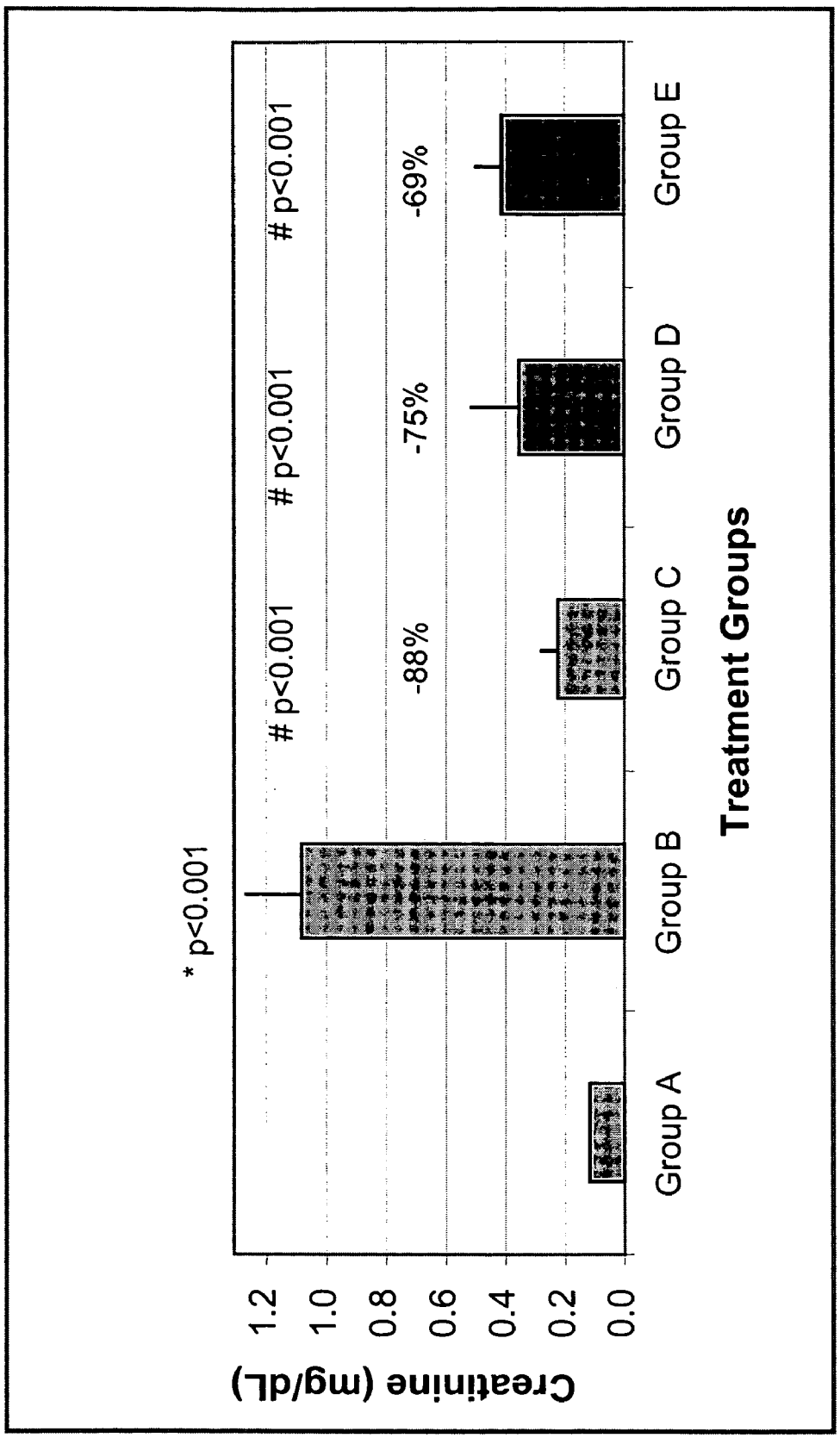
FIG. 5 sets forth data showing the methods and compounds of the present invention decreased serum creatinine levels in an animal model of impaired renal function.

As shown in FIG. 5, animals administered vehicle control prior to induction of impaired renal function (Group B) had elevated serum creatinine levels one day after induction of impaired renal function compared to that of sham control animals (Group A). Animals administered compound T prior to induction of impaired renal function showed significantly reduced serum creatinine levels compared to vehicle-treated animals with renal dysfunction. Specifically, administration of various concentrations of compound T (Group C, 15 mg/kg; Group D, 30 mg/kg; or Group E, 60 mg/kg) improved renal function as demonstrated by reducing the elevated serum creatinine levels 24 hours after induction of impaired renal function. (Values in FIG. 5 are presented as mean values for serum creatinine levels±SEM.) (* significantly higher than Group A; # significantly lower than Group B.)

These results demonstrated that methods and compounds of the present invention were effective at improving renal function.

Example 5

Improved Kidney Function in an Animal Model of Impaired Kidney Function

To examine the effects of compounds and methods of the present invention on kidney function, the following studies were performed. In this study, the effects of intravenous (i.v.) administration of compound T on renal function in a rat model of renal IRI were examined. Additionally, the effects of compound T administered at various times prior to and following induction of impaired renal function were also examined. For these studies, male Sprague Dawley rats (Charles River Labs) of approximately 280-300 grams were used. Animals were housed in an animal facility according to IACUC protocols with free access to water and food, and all experiments conducted according to the National Institutes of Health guidelines for animal experimentation.

Renal ischemia-reperfusion injury (IRI) and renal dysfunction were induced in rats using techniques previously described. (See Nemoto et al (2001) Kidney Int 59:246-251.) Briefly, rats were anesthetized under isoflurane and a midline abdominal incision was made under sterile conditions followed by bluntly dissecting the renal pedicles. A microvascular clamp was placed on the left renal pedicle for 45 minutes while the night kidney underwent simultaneous nephrectomy. After each occlusion, the clip was released at 45 minutes, and reperfusion was confirmed by observing a change in color of the kidney. Temperature was maintained constant, and warm (~37° C.) saline (1.0 mL) was administered directly into the abdomen. After the renal clamp was removed, the incision was sutured and the animal was allowed to recover and had free access to food and water. All experimental techniques were in accordance to National Institutes of Health guidelines for animal experimentation.

For these studies, animals were divided into 5 treatment groups and were treated with a single intravenous administration of vehicle or compound T as follows. Group A, i.v. administration of vehicle (6 mL/kg) 4 hours pre-sham operation without kidney dysfunction; Group B, i.v. administration of vehicle 4 hours prior to induction of impaired kidney function; Group C, i.v. administration of Cmpd T (20 mg/kg) 4 hours prior to induction of impaired kidney function; Group D, i.v. administration of Cmpd T (20 mg/kg) 45 minutes following induction of impaired kidney function; and Group E, i.v. administration of Cmpd T (20 mg/kg) 2 hours following induction of impaired kidney function.

Blood was collected on day 3, day 7, and day 10 for analysis of BUN levels and serum creatinine levels. After warm up under a heating lamp, rats were placed under isoflurane anesthesia and blood was collected from the tail vein at day 3 and day 7 and from the abdominal main vein at day 10. For serum, about 0.6 ml of blood was transferred to a Microtainer Serum Separator tube (Becton-Dickinson#365960). After being left at room temperature for about 30 minutes, the tubes were centrifuged at 4° C. and the serum (upper layer) was transferred to a 1.5 ml tube. The serum was transferred on wet ice to Quality Clinical Labs, Inc. (Mountain View, Calif.) for clinical chemistry analysis within 12 hours.

Figure 6:
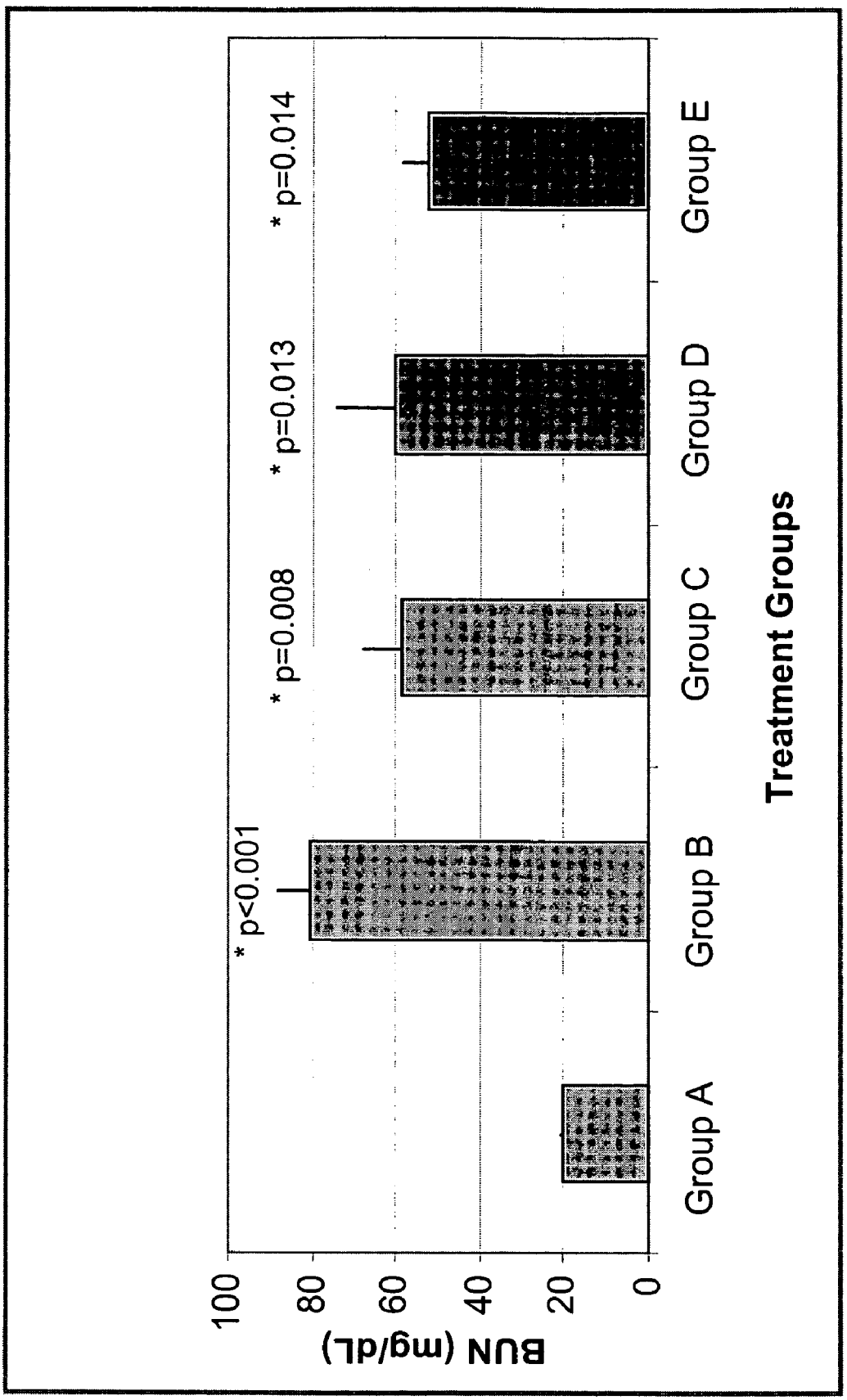
FIG. 6 sets forth data showing the methods and compounds of the present invention decreased BUN levels at day three following impaired renal function.
Figure 7:
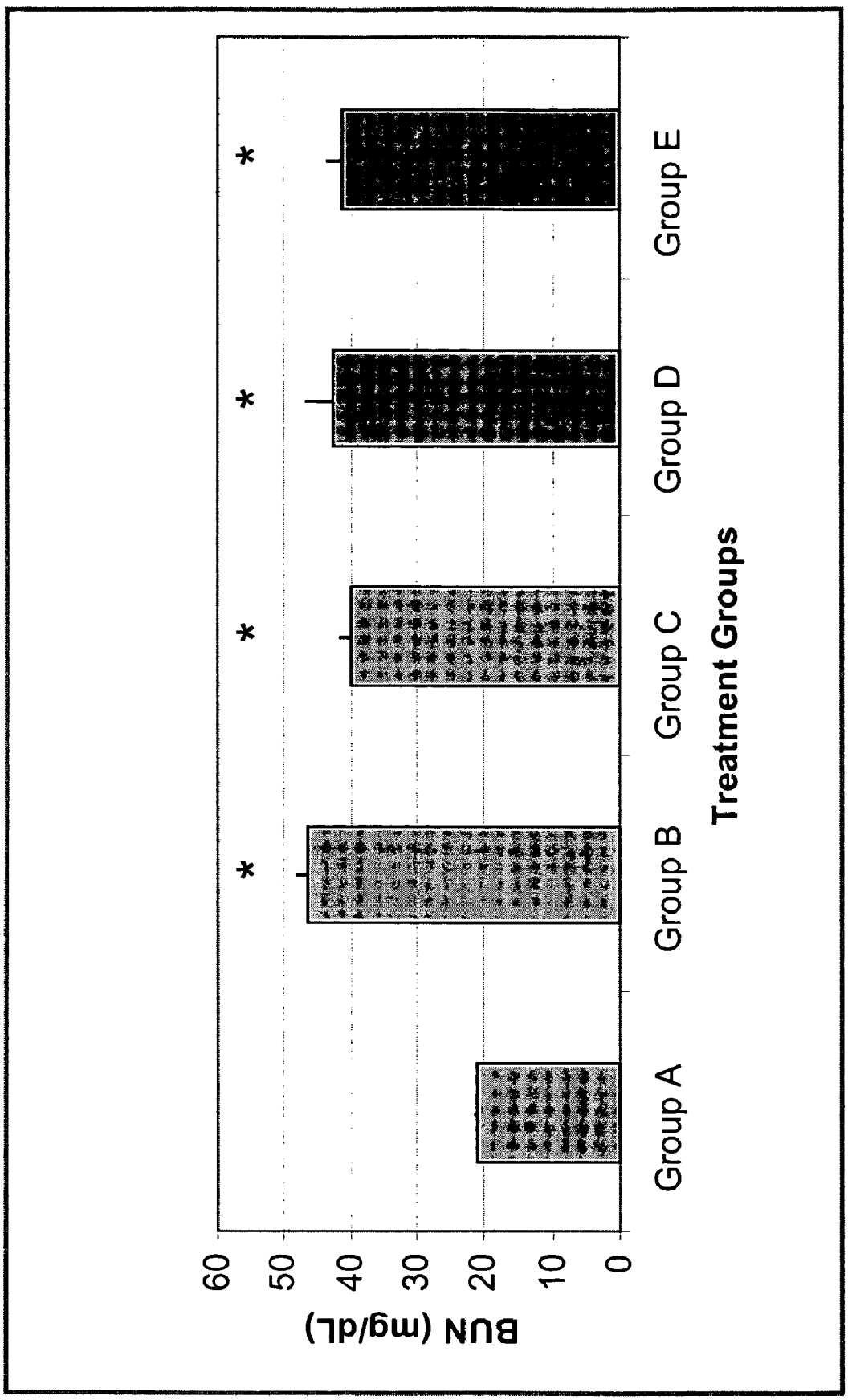
FIG. 7 sets forth data showing the methods and compounds of the present invention decreased BUN levels at day seven following impaired renal function.
Figure 8:
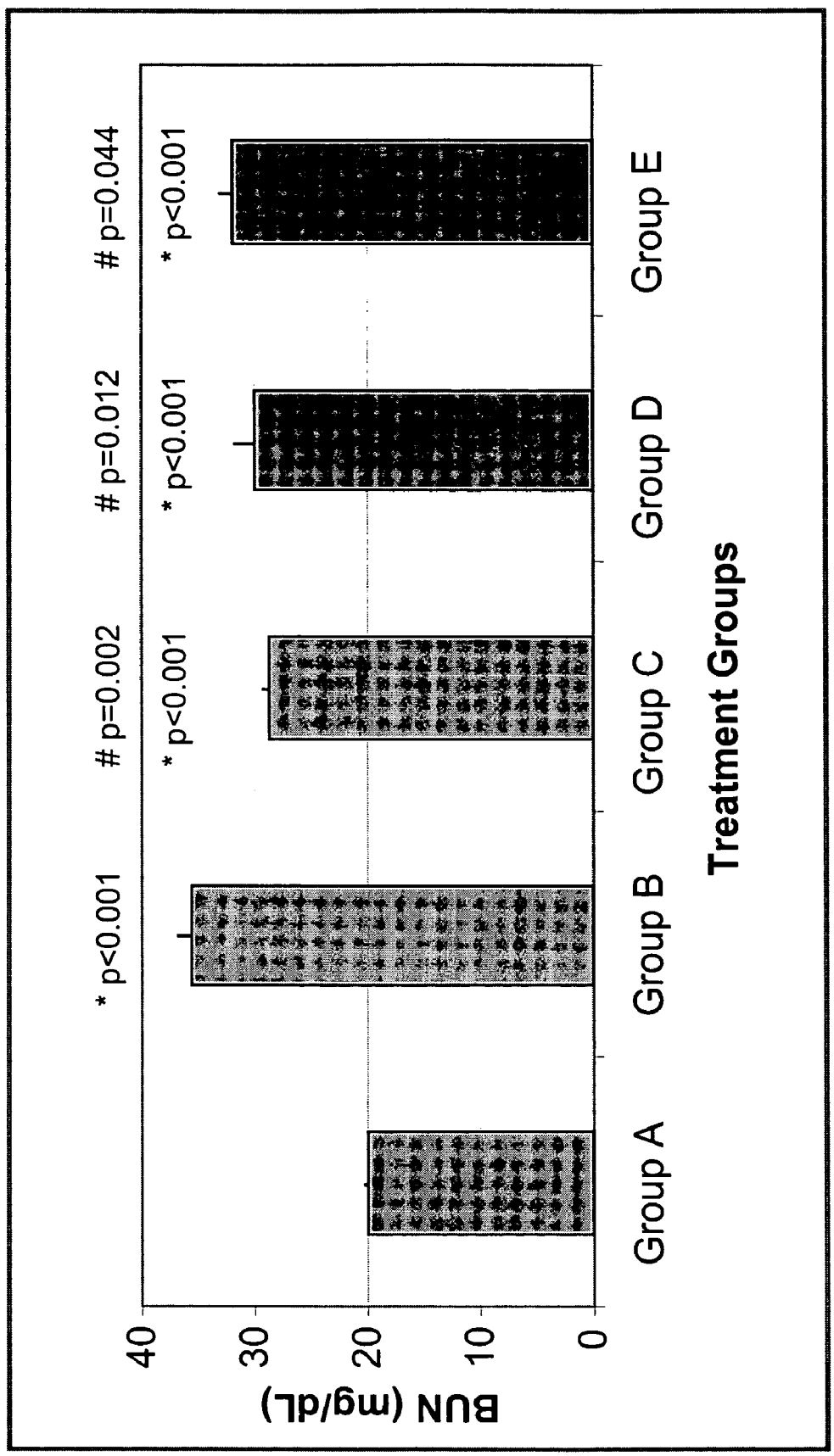
FIG. 8 sets forth data showing the methods and compounds of the present invention decreased BUN levels at day ten following impaired kidney renal function.

As shown in FIG. 6 (day 3), FIG. 7 (day 7), and FIG. 8 (day 10), animals administered vehicle control prior to induction of impaired renal function (Group B) had elevated BUN levels compared to that of sham control animals (Group A). Values in FIG. 6, FIG. 7, and FIG. 8 are presented as mean values for BUN levels±SEM. At day 3 (FIG. 6), day 7 (FIG. 7), and day 10 (FIG. 8), animals administered compound T 4 hours prior to IRI (Group C), 45 minutes following impairment of renal function (Group D), or 2 hours following impairment of renal function (Group E) had decreased BUN levels compared to vehicle-treated control animals with kidney dysfunction (Group B). These results showed that administration of compound T before or after induction of renal dysfunction improved renal dysfunction as demonstrated by a reduction in the elevated BUN levels. These results indicated that methods and compounds of the present invention are effective at reducing BUN levels and improving kidney function. (FIG. 6, * significantly higher than Group A; FIG. 7, * significantly higher than Group A ($p<0.001$); FIG. 8, * significantly higher than Group A; FIG. 8, # significantly lower than Group B.)

Figure 9:
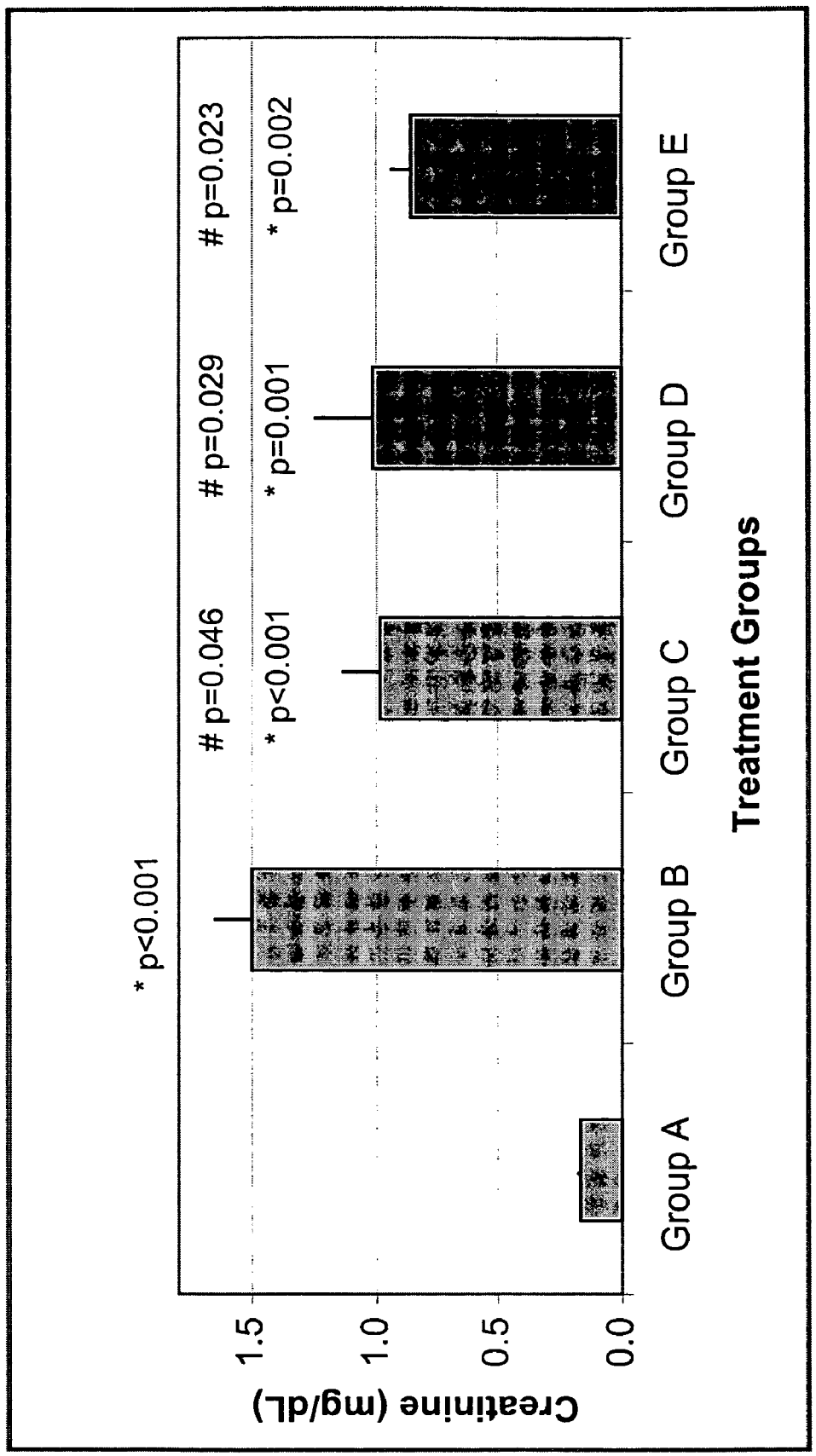
FIG. 9 sets forth data showing the methods and compounds of the present invention decreased serum creatinine levels at day three following impaired renal function.
Figure 10:
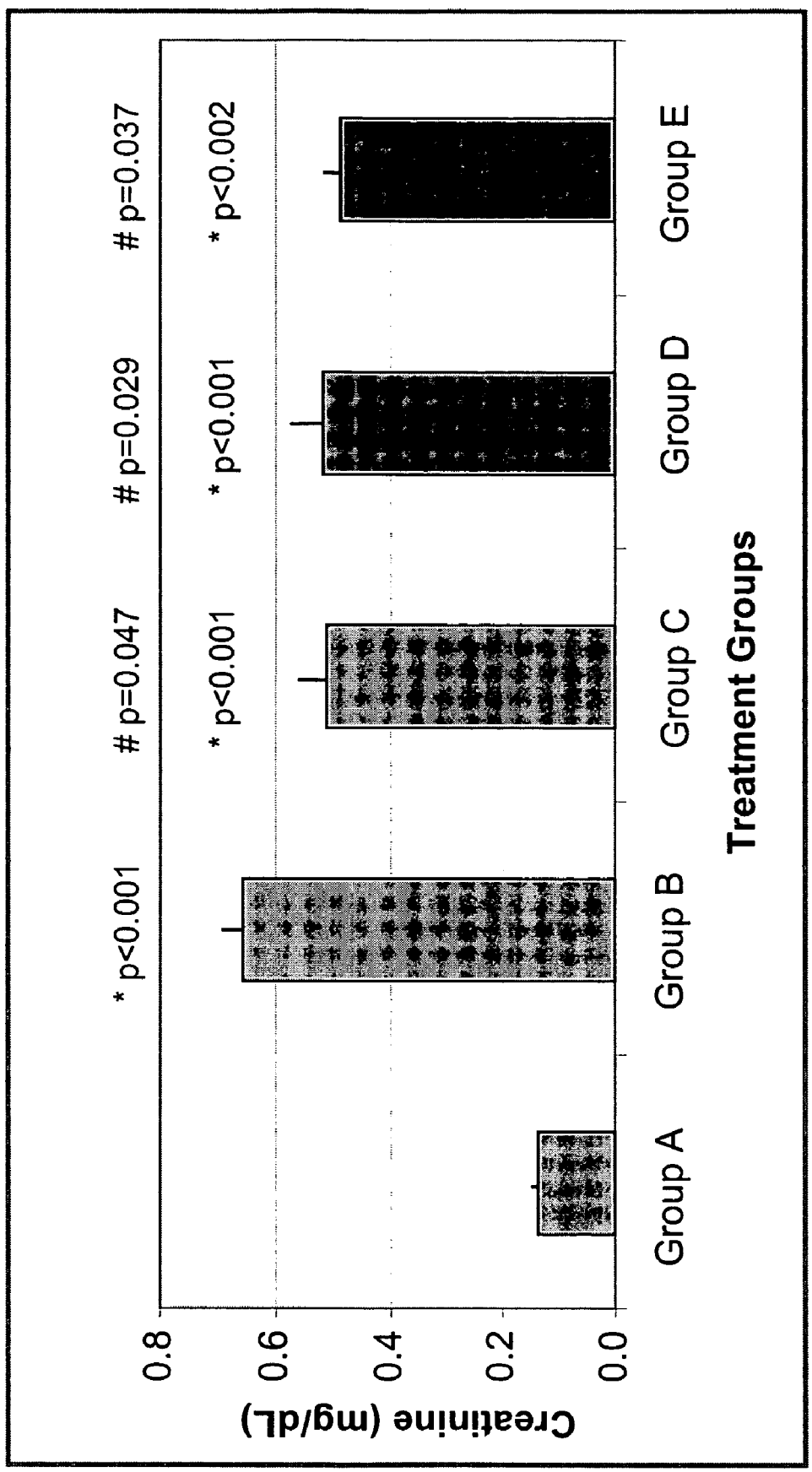
FIG. 10 sets forth data showing the methods and compounds of the present invention decreased serum creatinine levels at day seven following impaired renal function.
Figure 11:
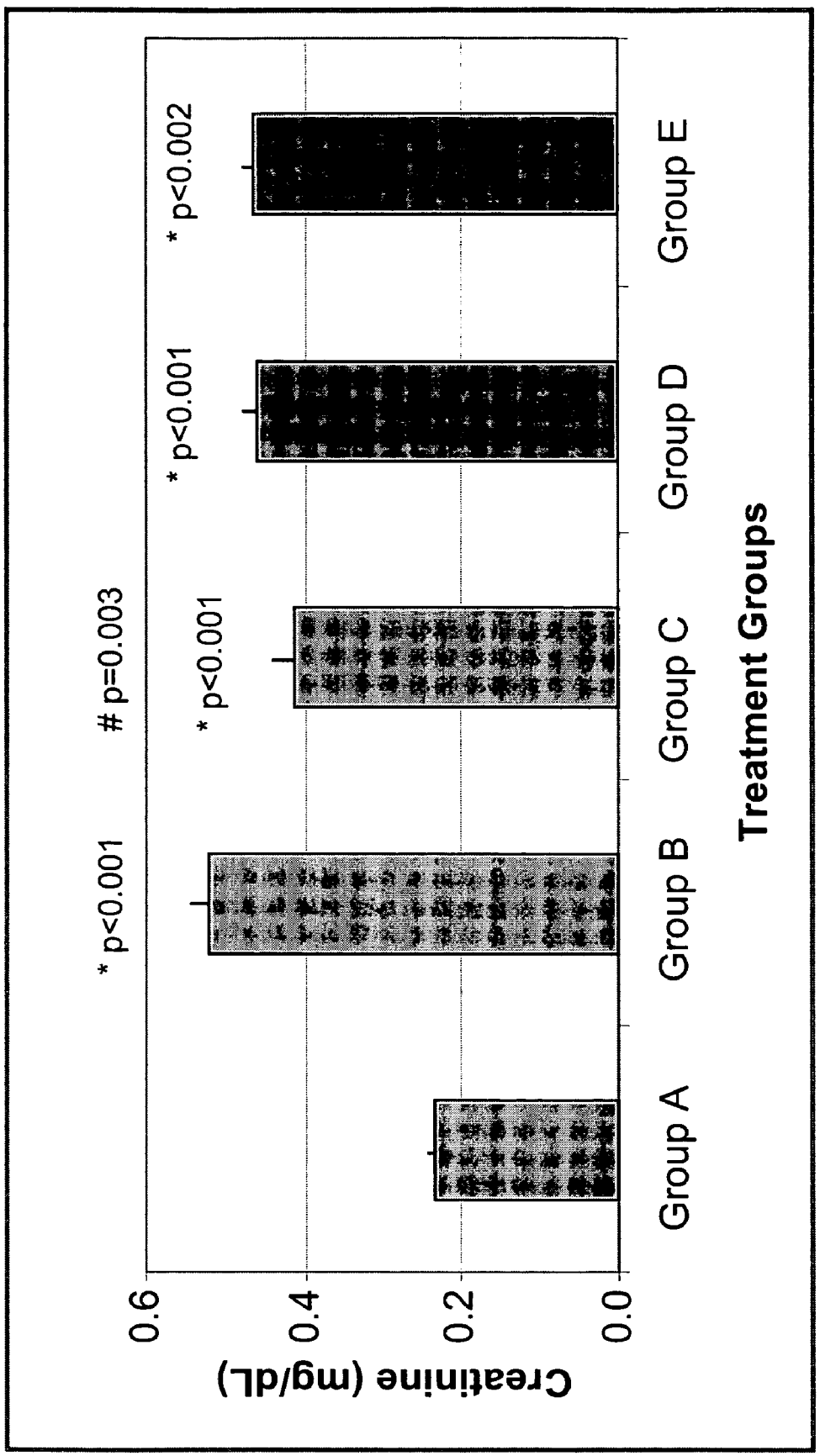
FIG. 11 sets forth data showing the methods and compounds of the present invention decreased serum creatinine levels at day ten following impaired renal function.

As shown in FIG. 9 (day 3), FIG. 1 (day 7), and FIG. 11 (day 10), animals administered vehicle control prior to induction of impaired renal function (Group B) had elevated serum creatinine levels compared to that of sham control animals (Group A). Values in FIG. 9, FIG. 10, and FIG. 11 are presented as mean values for serum creatinine levels±SEM. At day 3 (FIG. 9), day 7 (FIG. 10), and day 10 (FIG. 11), animals administered compound T 4 hours prior to induction of impaired renal function (Group C), 45 minutes following induction of impaired renal function (Group D), or 2 hours following induction of impaired renal function (Group E) had decreased serum creatinine levels compared to vehicle-treated control animals with kidney dysfunction (Group B). These results showed that administration of compound T before or after induction of renal dysfunction improved renal dysfunction as demonstrated by a reduction in the elevated serum creatinine levels. These results indicated that methods and compounds of the present invention are effective at reducing serum creatinine levels and improving kidney function. (FIG. 9, * significantly higher than Group A; FIG. 9, # significantly lower than Group B; FIG. 10, * significantly higher than Group A; FIG. 10, # significantly lower than Group B; FIG. 11, * significantly higher than Group A; FIG. 1, # significantly lower than Group B.)

Example 6

Improved Kidney Function in an Animal Model of Chemotherapy-Induced Kidney Dysfunction To examine the effects of compounds and methods of the present invention on kidney function following chemotherapy-induced renal injury, the following studies were performed. For the studies described below, male Sprague Dawley rats (Charles River Labs) of approximately 280-300 grams were used. Animals were housed in an animal facility according to IACUC protocols with free access to water and food, and all experiments conducted according to the National Institutes of Health guidelines for animal experimentation.

Cisplatin (CP) is an effective chemotherapeutic agent used in the treatment of a variety of solid tumors. Administration of CP is often associated with kidney injury and nephrotoxicity, resulting in impaired kidney function. For these experiments, CP-induced kidney dysfunction was performed as previously described (See Bagnis et al (2001) Nephrol Dial Transplant 16:932-938), with the following modifications. A single dose of CP (Cisplatin Injection, obtained from Bedford Laboratories, Bedford, Ohio) at 1.0 mg/mL was administered i.v. on day 0. Animals were administered compound B or compound U by oral gavage on day 0, day 2, day 4, day 7, day 9, and day 11. The initial dose of compound B or compound U was given ~2 h before the i.v. injection of CP.

For these studies, animals were divided into 8 treatment groups follows. Group A, i.v. administration of saline (5 mL/kg) and oral gavage administration of vehicle (5 mL/kg) 3×/wk; Group B, i.v. administration of saline (5 mL/kg) and oral gavage administration of Cmpd B (60 mg/kg) 3×/wk; Group C, i.v. administration of saline (5 mL/kg) and oral gavage administration of Cmpd U (40 mg/kg) 3×/wk; Group D, i.v. administration of CP (5 mg/kg) and oral gavage administration of vehicle (5 mL/kg) 3×/wk; Group E, i.v. administration of CP (5 mg/kg) and oral gavage administration of Cmpd B (30 mg/kg) 3×/wk; Group F, i.v. administration of CP (5 mg/kg) and oral gavage administration of Cmpd B (60 mg/kg) 3×/wk; Group G, i.v. administration of CP (5 mg/kg) and oral gavage administration of Cmpd U (20 mg/kg) 3×/wk; and Group H, i.v. administration of CP (5 mg/kg) and oral gavage administration of Cmpd U (40 mg/kg) 3×/wk.

On day 4, day 7, and day 14, blood was obtained from the animals for analysis of BUN levels and serum creatinine levels. Blood samples were obtained as follows. After being warmed under a heating lamp, animals were placed under isoflurane anesthesia and blood was collected from the tail vein. About 0.5 ml of blood was transferred to a Microtainer Serum Separator tube (Becton-Dickinson #365960). After being left at room temperature for about 30 min, the tubes were centrifuged at 4° C. and the serum (upper layer) was transferred to a 1.5 ml tube. The serum was transferred on wet ice to Quality Clinical Labs, Inc. (Mountain View, Calif.) for clinical chemistry analysis within 12 hours.

Figure 13:
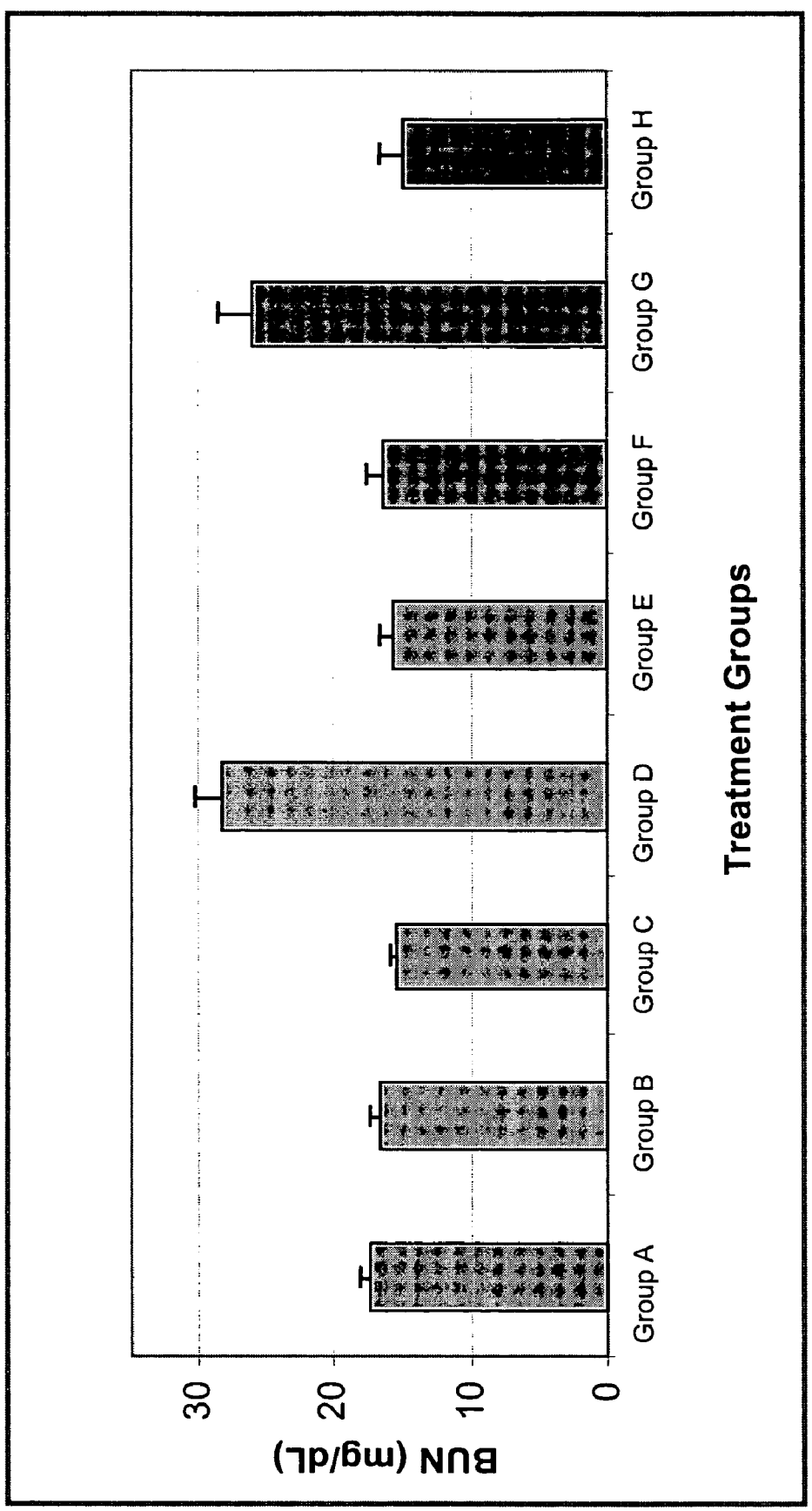
FIG. 13 sets forth data showing the methods and compounds of the present invention decreased BUN levels at day seven following cisplatin-induced kidney injury.
Figure 14:
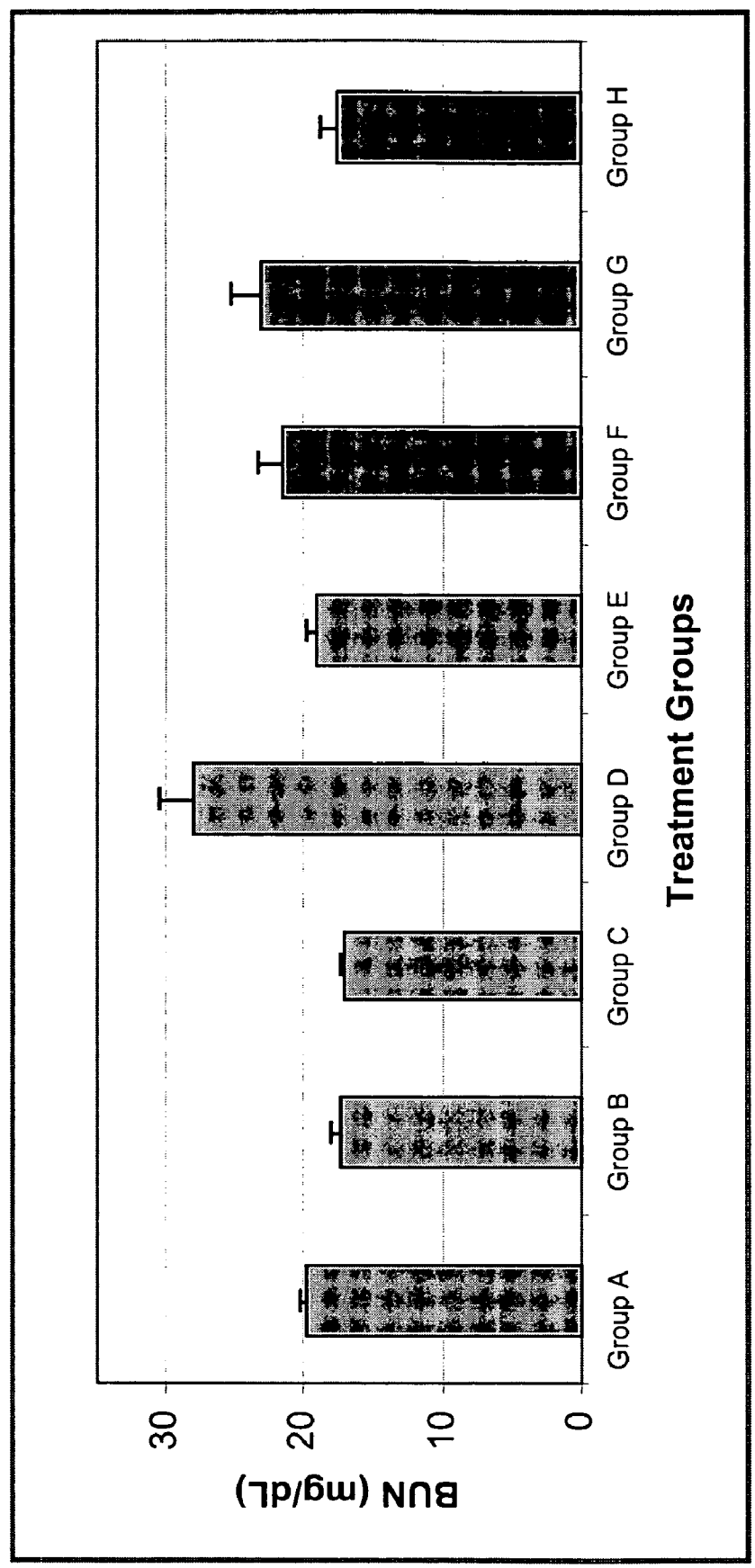
FIG. 14 sets forth data showing the methods and compounds of the present invention decreased BUN levels at day fourteen following cisplatin-induced kidney injury.

As shown in FIG. 13 (day 7) and FIG. 14 (day 14), animals administered CP and vehicle control (Group D) had elevated BUN levels compared to that of control animals (Group A). Values in FIG. 13 and FIG. 14 are presented as mean values for BUN levels ±SEM. At day 7 (FIG. 13) and day 14 (FIG. 14), animals injected with CP and administered compound B (Group E and Group F) or compound U (Group G and Group H) had decreased BUN levels compared to vehicle-treated animals injected with CP (Group D). These results showed that administration of compound B or compound U improved renal dysfunction following CP administration, as demonstrated by a reduction in the CP-induced elevation of BUN levels. These results indicated that methods and compounds of the present invention are effective at reducing BUN levels and improving kidney function.

Figure 15:
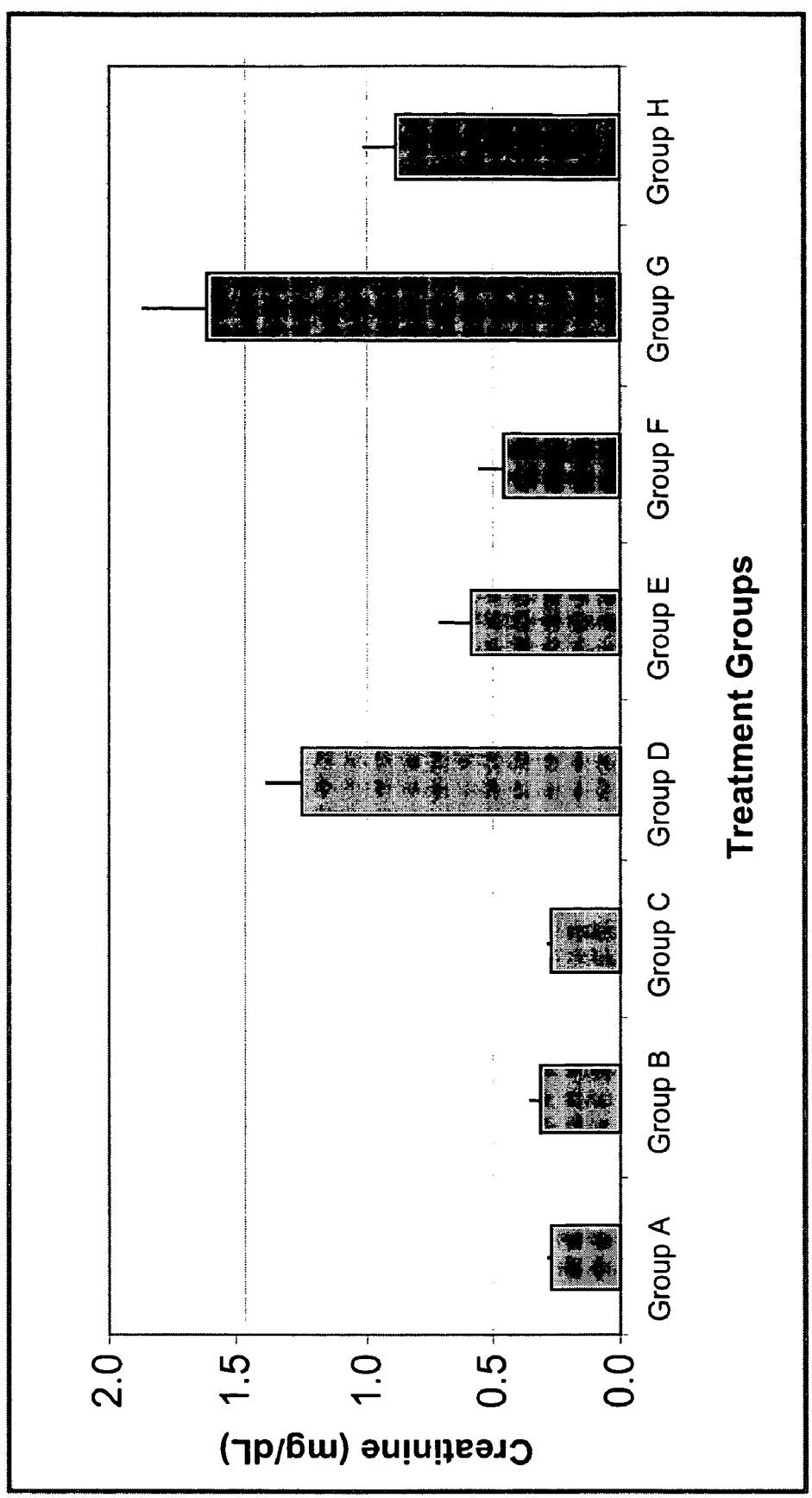
FIG. 15 sets forth data showing the methods and compounds of the present invention decreased serum creatinine levels at day three following cisplatin-induced renal injury.
Figure 16:
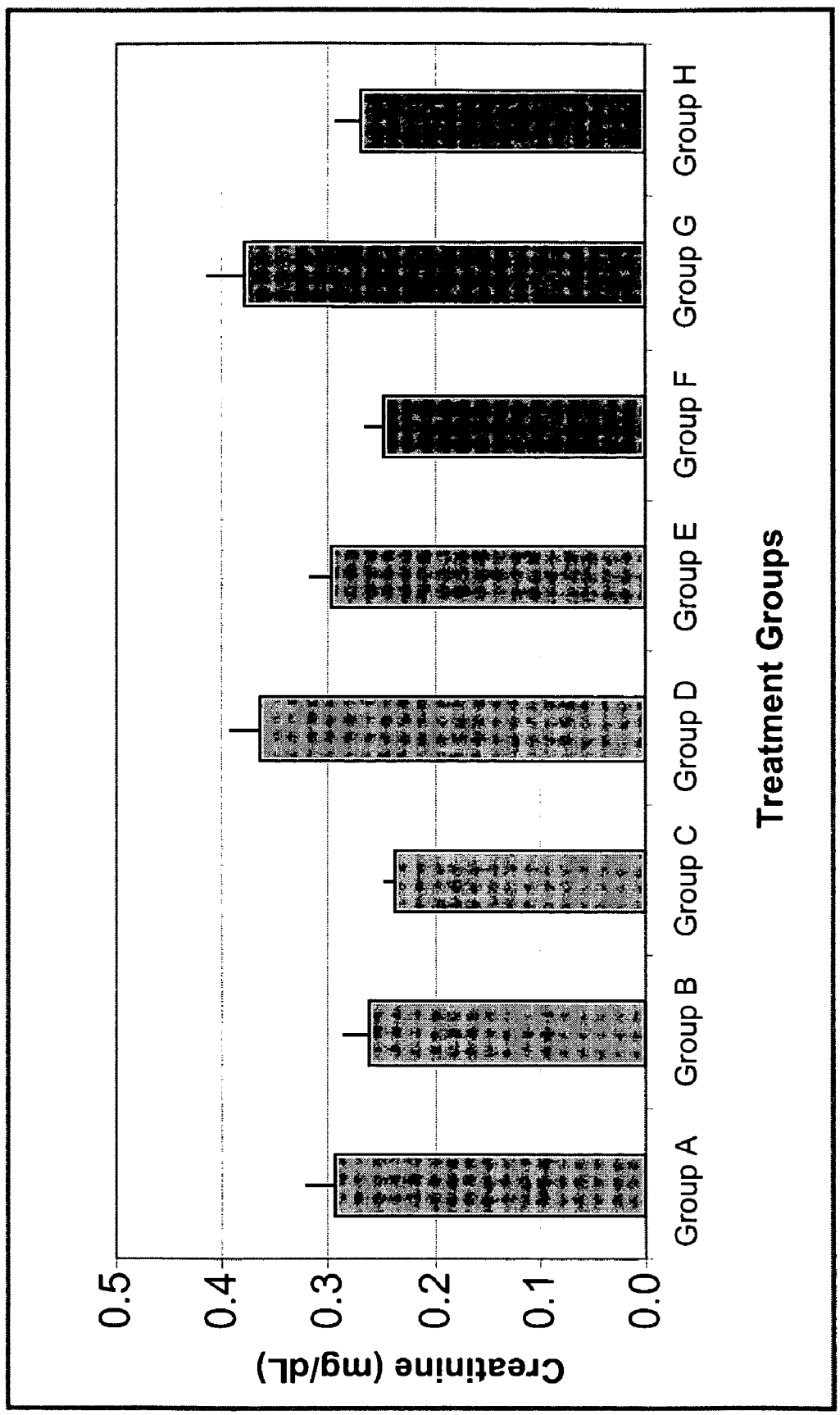
FIG. 16 sets forth data showing the methods and compounds of the present invention decreased serum creatinine levels at day seven following cisplatin-induced kidney injury.
Figure 17:
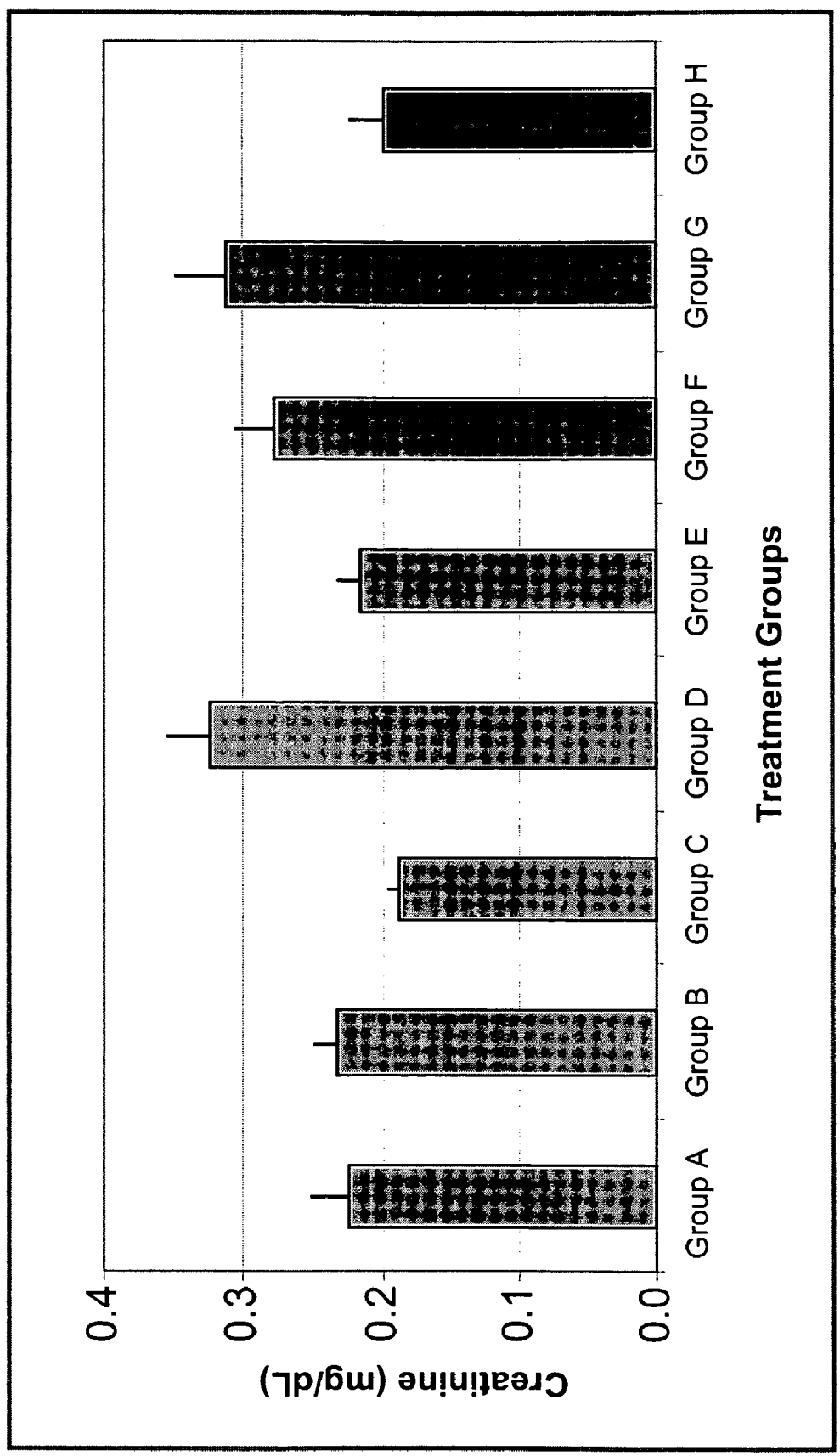
FIG. 17 sets forth data showing the methods and compounds of the present invention decreased serum creatinine levels at day fourteen following cisplatin-induced kidney injury.

As shown in FIG. 15 (day 4), FIG. 16, (day 7), and FIG. 17 (day 14), animals administered CP and vehicle control (Group D) had elevated serum creatinine levels compared to that of control animals (Group A). Values in FIG. 15, FIG. 16, and FIG. 17 are presented as mean values for serum creatinine levels ±SEM. At day 4 (FIG. 15), day 7 (FIG. 16), and day 14 (FIG. 17), animals injected with CP and administered compound B (Group E and Group F) or compound U (Group G and Group H) had decreased serum creatinine levels compared to vehicle-treated animals injected with CP (Group D). These results showed that administration of compound B or compound U improved renal dysfunction following CP administration, as demonstrated by a reduction in the CP-induced elevation of serum creatinine levels. These results indicated that methods and compounds of the present invention are effective at reducing serum creatinine levels and improving kidney function.

Example 7

Renal Ischemia-Reperfusion Injury

The model of ischemic acute renal failure was described in Nemoto et al. (2001, Kidney Int 59:246-251.) Briefly, male Sprague-Dawley rats (200-250 g) were treated with either 0.5% carboxymethyl cellulose (CMC; Sigma-Aldrich) or 1.5% compound B suspended in CMC by oral gavage in a volume of 4 ml/kg/day. Rats were pretreated daily for 4 consecutive days (days −3 to 0). A few hours after the fourth and last oral dose on day 0, renal ischemia-reperfusion injury (IRI) was performed.

Animals were divided into four groups: (1) Vehicle pretreatment and sham surgery; (2) compound B pretreatment and sham surgery; (3) vehicle pretreatment and EM surgery; and (4) compound B pretreatment and IRI surgery. Animals were anesthetized under isoflurane, an incision was made in the abdominal midline, and the renal pedicles were bluntly dissected. A vascular clip was placed on the right renal pedicle for 45 minutes while the left kidney underwent simultaneous nephrectomy. After each occlusion, the clip was released at 45 minutes, and reperfusion was observed by the changing color of the kidney. Temperature was maintained constant, and warm saline (0.5% of body weight) containing Buprenex analgesic was administered directly into abdomen before the incision was completely sutured.

The animal body weight and mortality were monitored. Blood samples were obtained from the tail vein, and serum chemistry and CBC were measured by IDEXX veterinary service (West Sacramento Calif.). Data are presented as mean ±SE with number of animals in parenthesis. The data were compared within the four groups at each time point using one-way analysis of variance (ANOVA, SIGMASTAT) and Student-Newman-Keuls method. A value of P<0.05 was considered significant.

Figure 18:
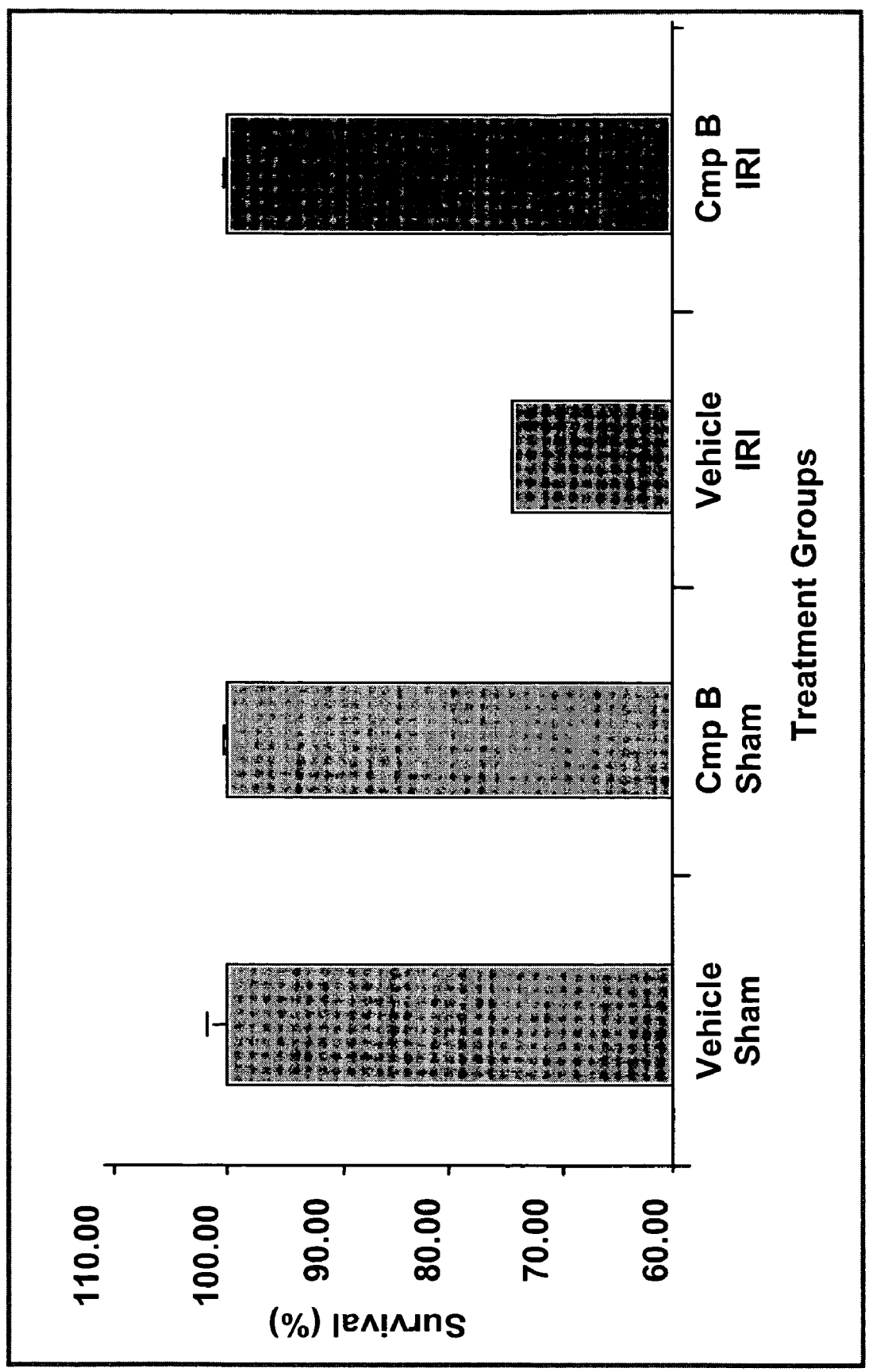
FIG. 18 shows increased survivability in animals subjected to renal ischemic-reperfusion injury that have been pretreated and consequently treated with compounds of the invention relative to untreated and sham-operated controls.
Figure 19:
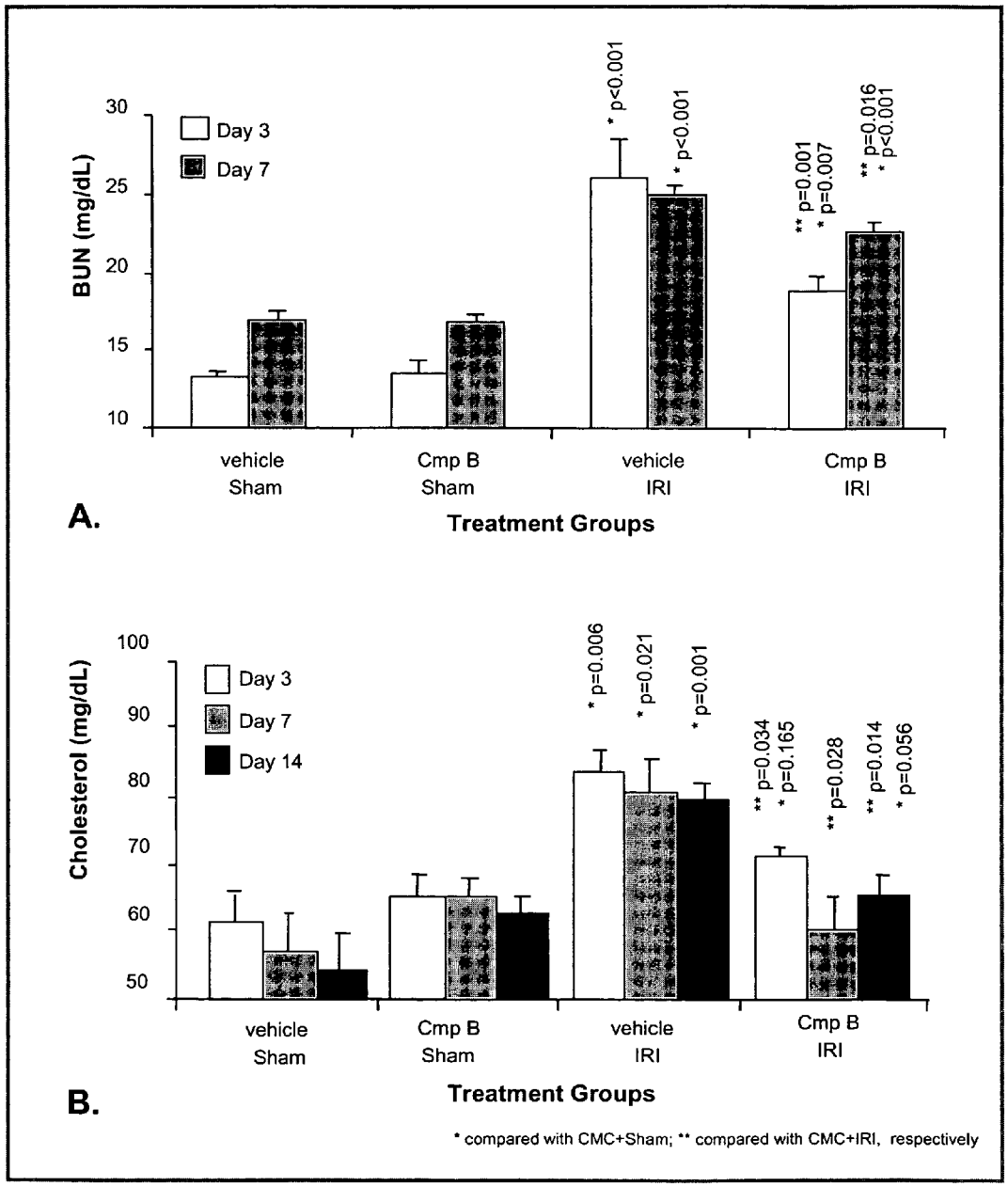
FIGS. 19A and 19B show improvement in kidney function following ischemic-reperfusion injury in animals pretreated with a compound of the invention relative to untreated controls.

As can be seen in FIG. 18, treatment with the compound prevented early mortality associated with ischemic-reperfusion injury. Further, serum blood urea nitrogen (BUN), a gauge of renal function, was significantly elevated by renal IRI at both 3 and 7 days, whereas treatment with compound produced significantly less IRI-induced increase in BUN. (FIG. 19A.) Additionally, serum cholesterol was significantly elevated by renal IRI at days 3, 7 and 14, whereas treatment with compound completely blocked IRI-induced increase in serum cholesterol. (FIG. 19B.) Athough the reasons are still under investigation, elevated kidney cholesterol is a natural reflection of renal ischemic-reperfusion injury. (Zager et al. (2001) Am J Pathol 159:743-752; Appel (1991) Kidney Int 39:169-183; and Abdel-Gayoum et al. (1999) Hum Exp Toxicol 18:454459.)

Example 8

Screening Assay

Compounds that inhibit HIF-specific prolyl hydroxylase activity and thereby stabilize HIFα can be identified and characterized using the following assay. A 50 μt aliquot of a reaction mix containing 4 mg/ml BSA, 0.1 M Tris HCl (pH 7.2), 2 mM ascorbate, 80 μM ferrous sulfate, 0.2 mM 2-oxoglutarate, 600 units/ml catalase, with or without 100 μM HIFα peptide is mixed with 50 μl HeLa cell extract or purified HIF prolyl hydroxylase and incubated 1.5 hours at 37° C. Following incubation, 50 μl of streptavidin beads are added and the mixture is incubated for 1 hour with agitation at 4° C. The mixture is transferred to tubes and centrifuged at low speed to pellet the beads. The beads are washed three times with 0.5 to 1 ml 20 mM Tris HCl (pH 7.2). The peptide is then eluted from the beads with 5 μl 2 mM biotin in 20 mM Tris HCl (pH 7.2) for 1 hour. The tubes are centrifuged to pellet the resin and 40-50 μl of supernatant is removed and an equal volume of acetonitrile is added. Alternatively, the peptide is attached to methoxycoumarin, a pH insensitive fluorophore. The fluorophore may provide sensitivity and specificity to enhance detection in assays run with crude cell lysate. An exemplary HIF peptide for use in the screening assay may comprise [methoxycoumarin]-DLDLEALAPYIPAD-DDFQL-amide. The non-hydroxylated and hydroxylated peptides are then separated by reverse-phase HPLC on a C18 column with UV detection at 214 nm.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method for improving kidney function in a subject having impaired kidney function, the method comprising administering to the subject an effective amount of an agent that inhibits hypoxia inducible factor (HIP) hydroxylase activity.

2. The method of claim 1, wherein the subject is a mammalian subject.

3. The method of claim 1, wherein the subject is a human subject.

4. The method of claim 1, wherein the subject has or is at risk for having an acute or chronic kidney disease.

5. The method of claim 1, wherein the acute or chronic kidney disease is acute kidney failure or chronic kidney failure.

6. The method of claim 1, wherein the subject has diabetes.

7. The method of claim 1, wherein the subject has hypertension.

8. A method for increasing glomerular filtration rate (GFR) in a subject having a decreased GFR, the method comprising administering to the subject an effective amount of an agent that inhibits RIF hydroxylase activity.

9. The method of claim 8, wherein the decreased GFR is selected from the group consisting of: below about 116 ml/min/1.73 m$^2$; below about 107 ml/min/1.73 m$^2$; below about 99 ml/min/1.73 m$^2$; below about 93 ml/min/1.73 m$^2$; below about 85 ml/min/1.73 m$^2$; and below about 75 ml/min/1.73 m$^2$.

10. The method of claim 8, wherein the increasing GFR comprises increasing GFR to a level selected from the group consisting of: above about 15 ml/min/1.73 m$^2$; above about 30 ml/min/1.73 m$^2$; above about 60 ml/min/1.73 m$^2$; and above about 90 ml/min/1.73 m$^2$.

* * * * *

UNITED STATES PATENT AND TRADEMARK OFFICE
CERTIFICATE OF CORRECTION

| | | |
|---|---|---|
| PATENT NO. | : 8,318,703 B2 | Page 1 of 1 |
| APPLICATION NO. | : 11/446417 | |
| DATED | : November 27, 2012 | |
| INVENTOR(S) | : Stephen J. Klaus et al. | |

It is certified that error appears in the above-identified patent and that said Letters Patent is hereby corrected as shown below:

In col. 54, claim 1, line 10, the abbreviation "HIP" should read --HIF--.

In col. 54, claim 5, line 18, reference to "claim 1" should read --claim 4--.

In col. 54, claim 8, line 27, recitation of "RIF" should read --HIF--.

Signed and Sealed this
Twenty-ninth Day of January, 2013

David J. Kappos
*Director of the United States Patent and Trademark Office*